US010294278B2

(12) United States Patent
Weiner et al.

(10) Patent No.: US 10,294,278 B2
(45) Date of Patent: May 21, 2019

(54) FOOT AND MOUTH DISEASE VIRUS (FMDV) CONSENSUS PROTEINS, CODING SEQUENCES THEREFOR AND VACCINES MADE THEREFROM

(71) Applicants: The Trustees of the University of Pennsylvania, Philadelphia, PA (US); Inovio Pharmaceuticals, Inc., Plymouth Meeting, PA (US)

(72) Inventors: David B. Weiner, Merion, PA (US); Bernadette Ferraro, La Jolla, CA (US); Jian Yan, Wallingford, PA (US); Patricia A. Brown, Magnolia, TX (US); Rodney A. Bowling, Austin, TX (US); Douglas R. Kern, The Woodlands, TX (US); Mathura P. Ramanathan, Ardmore, PA (US); Niranjan Y. Sardesai, Blue Bell, PA (US); Karuppiah Muthumani, Cherry Hill, NJ (US)

(73) Assignees: VGX PHARMACEUTICALS, LLC; THE TRUSTEES OF THE UNIVERSITY OF PENNSYLVANIA ( * ) Notice: Subject to any disclaimer, the term of this patent is extended or adjusted under 35 U.S.C. 154(b) by 0 days.

(21) Appl. No.: 14/816,120

(22) Filed: Aug. 3, 2015

(65) Prior Publication Data
US 2016/0039886 A1 Feb. 11, 2016

Related U.S. Application Data

(62) Division of application No. 13/503,828, filed as application No. PCT/US2010/055187 on Nov. 2, 2010, now Pat. No. 9,109,014.

(60) Provisional application No. 61/257,450, filed on Nov. 2, 2009, provisional application No. 61/257,461, filed on Nov. 2, 2009.

(51) Int. Cl.
C12N 7/00 (2006.01)
C07K 14/005 (2006.01)
A61K 39/12 (2006.01)
A61K 39/00 (2006.01)
A61K 39/135 (2006.01)
A61K 39/39 (2006.01)
A61M 37/00 (2006.01)
A61N 1/32 (2006.01)
G01N 33/569 (2006.01)

(52) U.S. Cl.
CPC ............ *C07K 14/005* (2013.01); *A61K 39/12* (2013.01); *A61K 39/135* (2013.01); *A61K 39/39* (2013.01); *A61M 37/00* (2013.01); *A61N 1/327* (2013.01); *C12N 7/00* (2013.01); *G01N 33/56983* (2013.01); *A61K 2039/523* (2013.01); *A61K 2039/53* (2013.01); *A61K 2039/552* (2013.01); *C12N 2770/32122* (2013.01); *C12N 2770/32134* (2013.01); *G01N 2333/09* (2013.01); *G01N 2469/20* (2013.01)

(58) Field of Classification Search
CPC A61K 2039/53; A61K 39/12; A61K 39/0011; A61K 2039/545; C07K 14/005
See application file for complete search history.

(56) References Cited

U.S. PATENT DOCUMENTS

| 4,510,245 | A | 4/1985 | Cousens et al. |
| 4,722,848 | A | 2/1988 | Paoletti et al. |
| 4,790,987 | A | 12/1988 | Compans et al. |
| 4,920,209 | A | 4/1990 | Davis et al. |
| 5,017,487 | A | 5/1991 | Stunnenberg et al. |
| 5,077,044 | A | 12/1991 | Stocker |
| 5,110,587 | A | 5/1992 | Paoletti et al. |
| 5,112,749 | A | 5/1992 | Brey, III et al. |
| 5,174,993 | A | 12/1992 | Paoletti |
| 5,223,424 | A | 6/1993 | Cochran et al. |
| 5,225,336 | A | 7/1993 | Paoletti |
| 5,240,703 | A | 8/1993 | Cochran |
| 5,242,829 | A | 9/1993 | Panicali |
| 5,273,525 | A | 12/1993 | Hofmann |
| 5,294,441 | A | 3/1994 | Curtiss, III et al. |
| 5,294,548 | A | 3/1994 | McLinden et al. |
| 5,310,668 | A | 5/1994 | Ellis et al. |
| 5,387,744 | A | 2/1995 | Curtiss, III et al. |
| 5,389,368 | A | 2/1995 | Gurtiss, III |

(Continued)

FOREIGN PATENT DOCUMENTS

| CN | 1737144 A | 2/2006 |
| CN | 10121938 | 2/2008 |

(Continued)

OTHER PUBLICATIONS

Carrillo et al., "Comparative genomics of foot-and-mouth disease virus", Journal of Virology, 2005, 79(10):6487-6504.
Cooke, J. et al., "Serotype-specific differences in antigenic regions of foot-and-mouth disease virus (FMDV): a comprehensive statistical analysis", Infect Genet Evol. 2008, 8(6): 855-63.
Wang, C. et al., "Effective synthetic peptide vaccine for foot-and-mouth disease in swine", Vaccine. 2002, 20 (19-20):2603-10.
Mohapatra, J.K. et al., "Comparative genomics of serotype Asia 1 foot-and-mouth disease virus isolates from India sampled over the last decades", Virus Research, 2008, 136:16-29.
Cottam, E.M. et al., "Molecular Epidemiology of the Foot-and-Mouth Diease Viurs Outbreak in the United Kingdom in 2001", Journal of Virology, 2006, 80:11274-11282.

(Continued)

Primary Examiner — Barry A Chestnut
(74) Attorney, Agent, or Firm — Riverside Law LLP

(57) ABSTRACT

Provided herein is a nucleic acid comprising consensus amino acid sequence of foot-and-mouth disease FMDV VP1-4 coat proteins of FMDV subtypes A, Asia 1, C, O, SAT1, SAT2, and SAT3 as well as plasmids and vaccines expressing the sequences. Also provided herein is methods for generating an immune response against one or more FMDV subtypes using the vaccine as described above as well as methods for deciphering between vaccinated mammals with the vaccine and those that are infected with FMDV.

20 Claims, No Drawings

Specification includes a Sequence Listing.

(56) References Cited

U.S. PATENT DOCUMENTS

| | | |
|---|---|---|
| 5,424,065 A | 6/1995 | Curtiss, III et al. |
| 5,451,499 A | 9/1995 | Cochran |
| 5,453,364 A | 9/1995 | Paoletti |
| 5,462,734 A | 10/1995 | Letchworth, III et al. |
| 5,470,734 A | 11/1995 | Sondermeijer et al. |
| 5,474,935 A | 12/1995 | Chatterjee et al. |
| 5,482,713 A | 1/1996 | Paoletti |
| 5,580,859 A | 12/1996 | Felgner et al. |
| 5,591,439 A | 1/1997 | Plotkin et al. |
| 5,593,972 A | 1/1997 | Weiner et al. |
| 5,643,579 A | 7/1997 | Hung et al. |
| 5,650,309 A | 7/1997 | Wong-Staal et al. |
| 5,676,594 A | 10/1997 | Joosten |
| 5,698,202 A | 12/1997 | Ertl et al. |
| 5,703,055 A | 12/1997 | Felgner et al. |
| 5,739,118 A | 4/1998 | Carrano et al. |
| 5,817,637 A | 10/1998 | Weiner et al. |
| 5,830,876 A | 11/1998 | Weiner et al. |
| 4,797,368 A | 1/1999 | Carter et al. |
| 5,955,088 A | 9/1999 | Ghiasi et al. |
| 5,962,428 A | 10/1999 | Carrano et al. |
| 5,981,505 A | 11/1999 | Weiner et al. |
| 6,034,298 A | 3/2000 | Lam et al. |
| 6,042,836 A | 3/2000 | Berman et al. |
| 6,110,161 A | 8/2000 | Mathiesen et al. |
| 6,156,319 A | 12/2000 | Cohen et al. |
| 6,261,281 B1 | 7/2001 | Mathiesen et al. |
| 6,589,529 B1 | 7/2003 | Choi et al. |
| 6,697,669 B2 | 2/2004 | Dev et al. |
| 6,939,862 B2 | 9/2005 | Bureau et al. |
| 6,958,060 B2 | 10/2005 | Mathiesen et al. |
| 7,238,522 B2 | 7/2007 | Hebel et al. |
| 7,245,963 B2 | 7/2007 | Draghia-Akli et al. |
| 7,328,064 B2 | 2/2008 | Mathiesen et al. |
| 2004/0265955 A1 | 12/2004 | Fang et al. |
| 2005/0052630 A1 | 3/2005 | Smith et al. |
| 2005/0182005 A1 | 8/2005 | Tuschl et al. |
| 2005/0287672 A1* | 12/2005 | Nordgren ............ A61K 39/135 435/456 |
| 2006/0251677 A1 | 11/2006 | Bachmann et al. |

FOREIGN PATENT DOCUMENTS

| | | |
|---|---|---|
| CN | 101270155 A | 9/2008 |
| WO | WO 94/016737 | 8/1994 |
| WO | WO 1999/66954 | 12/1999 |
| WO | 2006/063445 A1 | 6/2006 |
| WO | WO 08/116368 | 10/2008 |
| WO | WO 09/73330 | 6/2009 |

OTHER PUBLICATIONS

Martinez, M. et al., "Two mechanisms of antigenic diversification of foot-and-mouth disease virus", Virology.1991, 184(2):695-706.

Tosh et al., Phylogenetic analysis of serotype A foot-and-mouth disease virus isolated in India between 1977 and 2000, 2002, Archives of Virology, 147:493-513.

Kumar et al., Immunogenicity testing of novel engineered HIV-1 envelope Gp140 DNA vaccine construct, 2006, DNA and Cell Biology, 25(7):383-392.

"Polyprotein, partial (Foot-and-Mouth disease virus—type A)", GenBank Accession No. CAB62583, 2005 [retrieved Aug. 14, 2015—URL: http://www.ncbi.nlm.nih.gov/protein/CAB62583.1].

Du et al., "Immune responses of two recombinant adenoviruses expressing VP1 antigens of FMDV fused with porcine granulocyte macrophage colony-stimulating factor", Vaccine, 25(49): 8209-8219, 2007.

Cheung et al., "Comparison of the major antigen determinants of different serotypes of foot-and-mouth disease virus", J Virol, 48(2): 451-459, 1983.

Nagendrakumar et al., "Genetic analysis of foot-and-mouth disease virus serotype A of Indian origin and detection of positive selection and recombination in leader protease-and capsid-coding regions", Journal of Biosciences, 34(1): 85-101, 2009.

GenBank Accession No. EF185303, dated Jan. 15, 2007; https://www.ncbi.nlm.nih.gov/nuccore/EF185303.

GenBank Accession No. EF120387, dated Dec. 12, 2006; https://www.ncbi.nlm.nih.gov/nuccore/EF120387.

GenBank Accession No. EF120388, dated Dec. 12, 2006; https://www.ncbi.nlm.nih.gov/nuccore/EF120388.

GenBank Accession No. EF120389, dated Dec. 12, 2006; https://www.ncbi.nlm.nih.gov/nuccore/EF120389.

GenBank Accession No. EF120395, date Dec. 12, 2006; https://www.ncbi.nlm.nih.gov/nuccore/EF120395.

GenBank Accession No. EF120396, dated Dec. 12, 2006; https://www.ncbi.nlm.nih.gov/nuccore/EF120396.

GenBank Accession No. EF120397, dated Dec. 12, 2006; https://www.ncbi.nlm.nih.gov/nuccore/EF120397.

* cited by examiner

FOOT AND MOUTH DISEASE VIRUS (FMDV) CONSENSUS PROTEINS, CODING SEQUENCES THEREFOR AND VACCINES MADE THEREFROM

CROSS-REFERENCE TO RELATED APPLICATIONS

This application is a divisional of U.S. patent application Ser. No. 13/503,828, filed Jul. 9, 2012, which is the U.S. national phase application filed under 35 U.S.C. § 371 claiming benefit to International Patent Application No. PCT/US2010/55187, filed Nov. 2, 2010, which is entitled to priority under 35 U.S.C. §119(e) to U.S. Provisional Patent Application Nos. 61/257,450 and 61/257,461, both filed Nov. 2, 2009, each of which applications are incorporated by reference herein in their entireties.

FIELD OF THE INVENTION

The present invention relates to synthetic, consensus foot-and-mouth disease virus (FMDV) immunogenic proteins and nucleic acid molecule encoding such proteins, to vaccines against FMDV, to methods for inducing immune responses against FMVD, to methods for distinguishing between individuals infected with FMDV versus those vaccinated against FMDV, and methods of prophylactically and/or therapeutically immunizing individuals against FMDV.

BACKGROUND OF THE INVENTION

Foot-and-mouth disease is a highly contagious disease of domestic and wild cloven-hoofed animals including cattle, swine, goats and deer which rapidly replicates in the host and spreads to in-contact susceptible animals. The disease is characterized by fever, lameness, and vesicular lesions of the tongue, feet, snout, and teats resulting in high morbidity, but low mortality in adult animals. The causative agent is the foot-and-mouth disease virus (FMDV), the type of species of the *Aphthovirus* genus, of the Picornaviridae family. FMDV is a single-stranded, positive-sense RNA genome of approximately 8500 bases surrounded by an icosahedral capsid with 60 copies each of four structural proteins VP1-4 and is antigenically highly variable with several subtypes including A, Asia 1, O, C, SAT1, SAT2, and SAT3. Recent outbreaks of foot-and-mouth disease in a number of previously disease free countries including Taiwan in 1997, United Kingdom and Netherlands in 2001, and the emergence in several South American countries has risen the awareness of the economically destructive virus. Furthermore, there is world-wide concern that a possible terrorist attack may target countries such as the US $100 billion/year livestock industry by employing FMDV.

Previous measures to control FMDV include slaughter of the infected or in-contact animals and decontamination. Countries that slaughter their livestock due to a FMDV outbreak can only resume livestock activities if the countries have FMDV free status for 3 months after the last outbreak. Countries usually use vaccination of the animals to treat an FMDV outbreak as a last resort because countries that have vaccinated and do not slaughter the animals must wait an entire year to regain FMD free status. Countries however are looking to vaccinate their animals before any FMDV outbreak and would be able to retain their FMD free status.

In the past, FMDV vaccines included chemically inactivated whole virus antigen in conjunction with an adjuvant; however, there are disadvantages to this because it requires expensive high-containment manufacturing facilities to produce the vaccine. Over the past 25-30 years investigators have been trying to develop a vaccine that provides protection after a single inoculation. These efforts include the use of VP1 purified from virus particles, bioengineered VP1, VP1 peptides, chemically synthesized VP1 peptides, live vectors expressing VP1 epitopes, inoculation with DNA encoding VP1 epitopes, and using the full capsid protein VP1-4 produced from FMDV-infected cultures or delivery of the VP1-4 capsid via replication defective human adenovirus type 5 (Ad5) vector. All of these approaches present only a limited number of epitopes across all the subtypes of the FMDV viruses to the inoculated animal.

Accordingly, there is a need in the art for a vaccine and methods of diagnosing FMDV infected mammals that is suitable to provide protection against a plurality of epitopes of FMDV across the various subtypes of FDMV.

SUMMARY OF THE INVENTION

Provided herein is an isolated nucleic acid comprising a sequence encoding the consensus amino acid sequence of VP1-4 of foot-and-mouth disease virus subtypes A, Asia 1, C, O, SAT1, SAT2, SAT3, SAT4, or a complement thereof. The nucleic acid may comprise a sequence selected from the group consisting of (a) SEQ ID NOS: 17-23; (b) a nucleotide sequence encoding the amino acid sequence of 24-30; (c) a 80% variant of (a); and a complement of (a) or (b). Also provides is a vector comprising a heterologous sequence wherein the heterologous sequence consists of the sequence described above.

Also provided herein is a vaccine capable of generating in a mammal an immune response against a plurality of foot-and-mouth disease virus (FMDV) subtypes where the vaccine comprises a DNA plasmid comprising a promoter operably linked to a coding sequence that encodes a consensus FMDV antigen comprising capsid proteins VP1-4 from one or more FMDV subtypes and a pharmaceutically acceptable excipient wherein the DNA plasmid is capable of expressing the consensus FMDV antigen in a cell of the mammal in a quantity effective to elicit an immune response in the mammal. The vaccine may generate an immune response against FMDV subtypes A, Asia 1, C, O, SAT1, SAT2, SAT3 or combinations thereof. The coding sequences of the plasmid of the vaccine may be of the FMDV antigen selected from the group consisting of SEQ ID NOS: 1-7 or combinations thereof. The coding sequences of the plasmid of the vaccine may further comprise a N terminal leader sequence wherein the leader sequence is IgG or IgE. The plasmid of the vaccine may further comprise a polyadenylation sequence following the 3' end of the coding sequence. The plasmid of the vaccine may further comprise a nucleotide sequence encoding a consensus FMDV 3C protease from subtypes A, Asia 1, C, O, SAT1, SAT2, or SAT3. The nucleotide sequence of FMDV 3C protease may be SEQ ID NO: 15 and may encoded by the amino acid sequence as set forth in SEQ ID NO: 16. The plasmid of the vaccine may be codon optimized. The coding sequence of the FMDV antigen may also comprise VP1-4 and 3C protease including SEQ ID NOS: 7-14. The pharmaceutically acceptable excipient of the vaccine may be adjuvant and the adjuvant may be IL-2 or IL-15. The pharmaceutically acceptable excipient of the vaccine may be a transfection facilitating agent. The transfection facilitating agent may be a polyanion, polycation or lipid such as poly-L-glutamate at a concentration of less than 6 mg/ml. The vaccine may be administered to a swine, ruminant, human or a primate. The vaccine may elicit a humoral or cellular or both a humoral and cellular response.

Also provided herein is a vaccine capable of generating in a mammal an immune response against a plurality of foot-and-mouth disease virus (FMDV) subtypes where the vaccine comprises one or more DNA plasmids comprising a promoter operatively linked to a coding sequence that encodes a consensus FMDV antigen comprising capsid proteins VP1-4 from one or more FMDV subtypes selected from the group consisting of subtypes A, Asia 1, C, O, SAT1, SAT2, SAT3, or a combination thereof and a pharmaceutically acceptable excipient thereof wherein the DNA plasmids are capable of expressing a consensus FMDV antigen in a cell of the mammal in a quantity effective to elicit an immune response in the mammal. The coding sequence of the FMDV antigen may be selected from the group consisting of SEQ ID NOS: 1-7 or a combination thereof. The plasmid of the vaccine may also further comprise a nucleotide sequence encoding a consensus 3C protease of FMDV for subtypes A, Asia1, C, O. SAT1, SAT2, or SAT3 and may comprise the nucleotide sequences set forth in SEQ ID NO: 15. The vaccine may be administered to a mammal such as swine, ruminant, human or a primate. The vaccine may elicit an immune response in a mammal such as a humoral, cellular, or both a humoral and cellular response.

Also provided herein is a vaccine capable of generating in a mammal an immune response against a plurality of FDMV subtypes where the vaccine comprises an antigen comprising one or more consensus amino acid sequences encoding capsid proteins VP1-4 of foot-and-mouth-disease virus (FMDV) subtypes A, Asia 1, C, O, SAT1, SAT2, or SAT3 and a pharmaceutically acceptable excipient thereof. The coding amino acid sequence of the FMDV antigen may be SEQ ID NOS: 24-30. The pharmaceutically acceptable excipient may be an adjuvant selected from the group consisting of IL-2 and IL-15. The pharmaceutically acceptable excipient of the vaccine may be transfection facilitating agent. The transfection facilitating agent may be a polyanion, polycation or a lipid such as poly-L-glutamate at a concentration of less than 6 mg/ml. The vaccine may be administered to a mammal such as a swine, ruminant, human or primate. The vaccine may elicit an immune response in a mammal such as a humoral, cellular, or both a humoral and cellular response.

Also provided herein is a method for eliciting an immune response against a plurality of FMDV virus subtypes in a mammal comprising delivering the DNA plasmid vaccine of claim 1 or 21 to the tissue of the mammal and electroporating cells of the tissue with a pulse of energy at a constant current effective to permit entry of the DNA plasmid into the cells. The delivery of the DNA plasmid of claim 1 in the method may comprise injecting the DNA plasmid vaccine into the intradermic, subcutaneous, or muscle tissue. The DNA plasmid of the method may be delivered by presetting the current and the pulse of energy is at a constant current that equals the present current. The electroporation step of the method may further comprise measuring the impedance in the electroporated cells, adjusting the energy level of the pulse of energy relative to the measured impedance to maintain a constant current in the electroporated cells wherein the measuring and adjusting step occurs within a lifetime of the pulse of energy. The electroporating step may further comprise delivering the pulse of energy to a plurality of electrodes according to a pulse sequence pattern that delivers the pulse of energy in a decentralized pattern.

Also provided is a method of diagnosing a mammals infected with FMDV wherein the method comprises isolating a fluid sample from the mammal, isolating antibodies from the fluid sample of the mammal, and comparing the antibodies isolated from step b with a control mammal that has been inoculated with the vaccine of claim 3 wherein the control mammal only has antibodies to FMDV VP1-4 proteins and the infected FMDV mammal has antibodies to FMDV VP1-4 proteins and FMDV nonstructural proteins. The nonstructural proteins may be FMDV 2C, 3A, and 3D polymerase.

Isolated nucleic acid molecules comprising a sequence encoding a protein having one or more sequences selected from the group consisting of: one or more of SEQ ID NOs: 2, 4, 6, 8, 10, 12, 14, 16, 18, 20, 22, 24, 26, 28, 30, 32, 34, 36, 38, 40 and 42 with or without a leader sequence, complements thereof, immunogenic fragments thereof comprising at least 20 amino acids, variants with 80% or more homology to SEQ ID NOs: 2, 4, 6, 8, 10, 12, 14, 16, 18, 20, 22, 24, 26, 28, 30, 32, 34, 36, 38, 40 and 42, complements thereof, immunogenic fragments thereof comprising at least 20 amino acids, and complements thereof are provided In some embodiments, the nucleic acid sequences is selected from the group consisting of: SEQ ID NOS: 1, 3, 5, 7, 9, 11, 13, 15, 17, 19, 21, 23, 25, 27, 29, 31, 33, 35, 37, 39 and 41 with or without coding sequence for a leader sequence, complements thereof, fragments thereof encoding at least 20 amino acids, complements thereof, nucleic acid molecules 80% homologous to SEQ ID NOs: 1, 3, 5, 7, 9, 11, 13, 15, 17, 19, 21, 23, 25, 27, 29, 31, 33, 35, 37, 39 and 41, complements thereof, fragments thereof encoding at least 20 amino acids, and complements thereof Vaccine comprising such nucleic acid molecules and/or one or more proteins selected from the group consisting of SEQ ID NOs: 2, 4, 6, 8, 10, 12, 14, 16, 18, 20, 22, 24, 26, 28, 30, 32, 34, 36, 38, 40 and 42 with or without a leader sequence, immunogenic fragments thereof comprising at least 20 amino acids, variants with 80% or more homology to SEQ ID NOs: 2, 4, 6, 8, 10, 12, 14, 16, 18, 20, 22, 24, 26, 28, 30, 32, 34, 36, 38, 40 and 42, and immunogenic fragments thereof comprising at least 20 amino acids are provided.

Also provided are compositions comprising one or more proteins selected from the group consisting of SEQ ID NOs: 2, 4, 6, 8, 10, 12, 14, 16, 18, 20, 22, 24, 26, 28, 30, 32, 34, 36, 38, 40 and 42 with or without a leader sequence, immunogenic fragments thereof comprising at least 20 amino acids, variants with 80% or more homology to SEQ ID NOs: 2, 4, 6, 8, 10, 12, 14, 16, 18, 20, 22, 24, 26, 28, 30, 32, 34, 36, 38, 40 and 42, and immunogenic fragments thereof comprising at least 20 amino acids Methods of eliciting an immune response against one or more FMDV virus subtypes in a mammal are provided. The methods comprising using a vaccine disclosed here and, in some embodiments, may include the steps of administering a nucleic acid molecule encoding a protein having FMDV immunogenic sequence to the tissue of the mammal; and electroporating cells of the tissue with a pulse of energy at a constant current effective to permit entry of the DNA plasmid into the cells.

A method of diagnosing a mammals infected with FMDV in mammal vaccinated according to processes disclosed herein are also provided. The methods comprise isolating a fluid sample from the vaccinated mammal and detecting the presence of FMDV proteins not included in said vaccine and/or antibodies against FMDV proteins not included in said vaccine. The presence of such FMDV proteins and/or antibodies against such FMDV proteins indicates the vaccinated mammal has been infected with FMDV.

DETAILED DESCRIPTION

Consensus amino acid sequences have been generated for fusion proteins comprising multiple FMDV proteins and individual FMDV proteins from various serotypes. Nucleic acid molecules encoding the proteins have also been generated In one aspect of the present invention, there are fusion proteins comprising consensus FMDV proteins VP1, VP2, VP3, VP4 and/or 3C and nucleic acid sequences encoding these proteins, which can be generated and used in a vaccine to provide protection of mammals against foot-and-mouth disease across one or more subtypes of FMDV, including A, Asia 1, O, C, SAT1, SAT2, and SAT3.

In another aspect of the present invention, there are fusion proteins comprising consensus FMDV proteins VP1 and nucleic acid sequences encoding these proteins, from two different subtypes which can be generated and used in a vaccine to provide protection of mammals against foot-and-mouth disease across one or more subtypes of FMDV, including A, Asia 1, O, C, SAT1, SAT2, and SAT3.

In another aspect of the present invention, there are consensus FMDV proteins VP1 and nucleic acid sequences encoding them which can be generated and used in a vaccine to provide protection of mammals against foot-and-mouth disease across one or more subtypes of FMDV, including A, Asia 1, O, C, SAT1, SAT2, and SAT3.

While not being bound by scientific theory, a vaccine directed against the consensus amino acid sequences of VP1, VP2, VP3, and/or VP4 for one or more subtypes of FMDV will present a large repertoire of epitopes that are effective in eliciting an effective immune response (either humoral, cellular or both) against a majority of the species within each subtype of FMDV. This invention relates to using these consensus amino acid VP1, VP2, VP3, and/or VP4 sequences of the FMDV subtypes to generate suitable plasmids and proteins to be used in vaccines for administering to mammals to provide a preventive protection against FMDV. Also, this invention relates to a diagnostic method using these consensus sequences of FMDV VP1, VP2, VP3, and/or VP4 antigens to identify and distinguish mammals that have been properly vaccinated and are uninfected vs. mammals that have been infected with FMDV via the detection of antibodies directed to nonstructural proteins of FMDV such as the 3D polymerase.

While not being bound by scientific theory, VP1 is an excellent immunogenic target for a vaccine directed against the consensus amino acid sequences of VP1. VP1 is a predominant immunogen.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein may mean any molecule added to the DNA plasmid vaccines described herein to enhance antigenicity of the foot-and-mouth disease virus (FMDV) antigen encoded by the DNA plasmids and encoding nucleic acid sequences described hereinafter.

b. Antibody

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to whom the nucleic acid is administered.

d. Complement

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein may mean a synthetic nucleic acid sequence, or corresponding polypeptide sequence, constructed based on analysis of an alignment of multiple subtypes of a particular influenza antigen, that can be used to induce broad immunity against multiple subtypes or serotypes of a particular influenza antigen. Consensus FMDV antigens may include VP1, VP2, VP3, VP4, and C2 protease nucleotide and amino acid sequences. Also, synthetic antigens such as fusion proteins may be manipulated to consensus sequences (or consensus antigens).

f. Constant Current

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

h. Decentralized Current

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

i. Electroporation

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

j. Feedback Mechanism

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

k. Fragment

"Fragment" as used herein may mean a portion or a nucleic acid that encodes a polypeptide capable of eliciting an immune response in a mammal substantially similar to that of the non-fragment for at least one FMDV subtype such as A, Asia 1, C, O, SAT1, SAT2, or SAT3. The fragments may be DNA fragments selected from at least one of the various encoding nucleotide sequences of the present invention, including SEQ ID NOS: 1-7, and 15-21. The fragments may comprise at least 10%, at least 20%, at least 30%, at least 40%, at least 50%, at least 60%, at least 70%, at least 80%, at least 90% or at least 95% of the nucleic acid sequence of SEQ ID NOs: 1, 3, 5, 7, 9, 11, 13, 15, 17, 19, 21, 23, 25, 27, 29, 31, 33, 35, 37, 39 and 41. Fragments of may comprise at least 10%, at least 20%, at least 30%, at least 40%, at least 50%, at least 60%, at least 70%, at least 80%, at least 90% or at least 95% of SEQ ID NOS: 1, 3, 5, 7, 9, 11, 13, 15, 17, 19, 21, 23, 25, 27, 29, 31, 33, 35, 37, 39 and 41 provided the fragments include one or more of amino acids 21, 86, 127, 129, 154, 156, 182, 195, 206, 218, 220, 237, 249, 255, 265, 271 or 275. All such fragments may also optionally exclude amino acids. The DNA fragments may be 30 or more nucleotides in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, 720 or more, 780 or more, 840 or more, 900 or more, 960 or more, 1020 or more, 1080 or more, 1140 or more, 1200 or more, 1260 or more, 1320 or more, 1380 or more, 1440 or more, 1500 or more, 1560 or more, 1620 or more, 1680 or more, 1740 or more, 1800 or more, 1860 or more, 1820 or more, 1880 or more, 1940 or more, 2000 or more, 2600 or more, 2700 or more, 2800 or more, 2900 or more, 2910 or more, 2920 or more, 2930 or more, 2931 or more, 2932 or more, 2933 or more, 2934 or more, 2935 or more, 2936 or more, 2937 or more, or 2938 or more in length DNA fragments may comprise coding sequences for the immunoglobulin leader such as IgE or IgG sequences.

DNA fragments may be fewer than 10 nucleotides, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 720, fewer than 780, fewer than 840, fewer than 900, fewer than 960, fewer than 1020, fewer than 1080, fewer than 1140, fewer than 1200, fewer than 1260, fewer than 1320, fewer than 1380, fewer than 1440, fewer than 1500, fewer than 1560, fewer than 1620, fewer than 1680, or fewer than 1740 nucleotides, fewer than 1800, fewer than 1860, fewer than 1820, fewer than 1880, fewer than 1940, fewer than 2000, fewer than 2600, fewer than 2700, fewer than 2800, fewer than 2900, fewer than 2910, fewer than 2920, fewer than 2930, fewer than 2931, fewer than 2932, fewer than 2933, fewer than 2934, fewer than 2935, fewer than 2936, fewer than 2937, or fewer than 2938.

"Fragment" may also mean a polypeptide fragment that is capable of eliciting an immune response in a mammal substantially similar to that of the non-fragment for at least one FMDV subtype such as A, Asia 1, C, O, SAT1, SAT2, or SAT3. The fragment may be polypeptide fragment selected from at least one of the various encoding polypeptide sequences of the present invention, including SEQ ID NOs: 2, 4, 6, 8, 10, 12, 14, 16, 18, 20, 22, 24, 26, 28, 30, 32, 34, 36, 38, 40 and 42. Polypeptide fragment may be analyzed to contact at least one antigenic epitope as provided by a publicly available database such as the Los Alamos National Laboratory's FMDV Sequence Database. Fragments of proteins may comprise at least 10%, at least 20%, at least 30%, at least 40%, at least 50%, at least 60%, at least 70%, at least 80%, at least 90% or at least 95% of SEQ ID NOs: 2, 4, 6, 8, 10, 12, 14, 16, 18, 20, 22, 24, 26, 28, 30, 32, 34, 36, 38, 40 and 42. Polypeptides may comprise amino acid sequences for the immunoglobulin leader such as IgE or IgG. The polypeptide fragments may be 30 or more amino acids in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, or 710 amino acids or more in length Polypeptide fragments may be fewer than 10 amino acids, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 700, fewer than 701, fewer than 702, fewer than 703, fewer than 704, fewer than 705, fewer than 706, fewer than 707, fewer than 708, fewer than 709, or fewer than 710 amino acids in length.

l. Homology

Homology of multiple sequence alignments may generated using ClustalW (http://www.ebi.ac.uk/Tools/clustalw2/index.html).

m. Identical

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

n. Impedance

"Impedance" as used herein may be used when discussing the feedback mechanism and can be converted to a current value according to Ohm's law, thus enabling comparisons with the preset current.

o. Immune Response

"Immune response" as used herein may mean the activation of a host's immune system, e.g., that of a mammal, in response to the introduction of FMDV consensus antigen via the provided DNA plasmid vaccines. The immune response can be in the form of a cellular or humoral response, or both.

p. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O— and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature (Oct. 30, 2005), Soutschek et al., Nature 432:173-178 (2004), and U.S. Patent Publication No. 20050107325, which are incorporated herein by reference. Modified nucleotides and nucleic acids may also include locked nucleic acids (LNA), as described in U.S. Patent No. 20020115080, which is incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

q. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

r. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

s. Stringent Hybridization Conditions "Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

t. Substantially Complementary

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

u. Substantially Identical

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

v. Subtype or Serotype

"Subtype" or "serotype" as used herein interchangeably and in reference to FMDV viruses, and means genetic variants of a FMDV virus antigen such that one subtype is recognized by an immune system apart from a different subtype.

w. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

x. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. FMDV Proteins

Provided herein is an antigen capable of eliciting an immune response in a mammal against one or more foot-and-mouth disease virus (FMDV) subtypes. The antigen may be a FMDV antigen comprising capsid protein VP1, VP2, VP3, VP4, a consensus thereof, a variant thereof, a fragment thereof or a combination thereof. The FMDV antigen may be from FMDV subtype A, Asia 1, C, O, SAT1, SAT2, or SAT3. The FMDV antigen may contain at least one antigenic epitope that may be effective against particular FMDV immunogens against which an immune response can be induced. The empty viral capsid proteins VP1-4 of the FMDV antigen provides an entire repertoire of immunogenic sites and epitopes present in an intact FMDV virus. The consensus FMDV antigen sequence may be derived from FMDV antigen sequences from a plurality of FMDV viruses of one FMDV subtype. The consensus FMDV antigen may comprise VP1, VP2, VP3, and VP4 FMDV subtype consensus protein sequences, which may be a consensus VP1-4 protein. The consensus VP1-4 protein may comprise at least one FMDV protein 3C cleavage site. The protein 3C cleavage site may be present in between each of consensus VP1, VP2, VP3, and VP4 sequences of the consensus VP1-4 protein. Cleavage of the consensus VP1-4 protein by protein 3C may cleave the consensus VP1-4 protein to produce a consensus VP1-, a consensus VP2-, a consensus VP3-, and a consensus VP4 protein. Alternatively, a native proteolytic cleavage site can be present in between each of the consensus antigen sequences, such as the amino acid sequence: SEQ ID NO:45: RGRKRRS.

Fusion proteins comprising consensus VP1, VP2, VP3 and VP4, and a consensus of protease 3C are provided. The are SEQ ID NOs: 2, 4, 6, 8, 10, 12 and 14 which are consensus sequences of subtypes A, Asia 1, C, O, SAT1, SAT2 and SAT3 respectively.

SEQ ID NO:16 is a consensus 3C protease sequence.

Fusion proteins comprising consensus VP1, VP2, VP3 and VP4 are provided. The are SEQ ID NOs: 18, 20, 22, 24, 26, 28 and 30, which are consensus sequences of subtypes A, Asia 1, C, O, SAT1, SAT2 and SAT3 respectively.

SEQ ID NOs:32, 34, 36, and 38 are consensus sequences for VP1 subtypes Asia, O, A and C, respectively. These sequences include the IgE leader sequence SEQ ID NO:44 which may in each case be substituted with a different leader or deleted and substituted with methionine.

SEQ ID NOs:40 and 42 are fusion proteins of two consensus sequences for VP1. SEQ ID NO:40 is consensus VP1 subtypes A and VP1 subtype C. SEQ ID NO:42 is consensus VP1 subtypes Asia and VP1 subtype O. These sequences include the IgE leader sequence SEQ ID NO:44 which may in each case be substituted with a different leader or deleted and substituted with methionine.

Additionally, proteins may be fragments of SEQ ID NOs: 2, 4, 6, 8, 10, 12, 14, 16, 18, 20, 22, 24, 26, 28, 30, 32, 34, 36, 38, 40 and 42. In some embodiments, proteins are 20% of the consensus protein. In some embodiments, proteins are 20% of the consensus protein. In some embodiments, proteins are 30% of the consensus protein. In some embodiments, proteins are 40% of the consensus protein. In some embodiments, proteins are 50% of the consensus protein. In some embodiments, proteins are 60% of the consensus protein. In some embodiments, proteins arc 70% of the consensus protein. In some embodiments, proteins arc 80% of the consensus protein. In some embodiments, proteins are 90% of the consensus protein. In some embodiments, proteins are 95% of the consensus protein. In some embodiments, proteins are 96% of the consensus protein. In some embodiments, proteins are 97% of the consensus protein. In some embodiments, proteins are 98% of the consensus protein. In some embodiments, proteins are 99% of the consensus protein.

Additionally, proteins may be homologous to SEQ ID NOs: 2, 4, 6, 8, 10, 12, 14, 16, 18, 20, 22, 24, 26, 28, 30, 32, 34, 36, 38, 40 and 42. In some embodiments, proteins are 80% homologous. In some embodiments, proteins arc 90% homologous. In some embodiments, proteins are 95% homologous. In some embodiments, proteins are 96% homologous. In some embodiments, proteins are 97% homologous. In some embodiments, proteins are 98% homologous. In some embodiments, proteins are 99% homologous.

Additionally, proteins may be fragments of proteins homologous to SEQ ID NOs: 2, 4, 6, 8, 10, 12, 14, 16, 18, 20, 22, 24, 26, 28, 30, 32, 34, 36, 38, 40 and 42. In some embodiments, proteins are 20% of the homologous protein. In some embodiments, proteins are 20% of the homologous protein. In some embodiments, proteins are 30% of the homologous protein. In some embodiments, proteins are 40% of the homologous protein. In some embodiments, proteins are 50% of the homologous protein. In some embodiments, proteins are 60% of the homologous protein. In some embodiments, proteins are 70% of the homologous protein. In some embodiments, proteins are 80% of the homologous protein. In some embodiments, proteins are 90% of the homologous protein. In some embodiments, proteins are 95% of the homologous protein. In some embodiments, proteins are 96% of the homologous protein. In some embodiments, proteins are 97% of the homologous protein. In some embodiments, proteins are 98% of the homologous protein. In some embodiments, proteins are 99% of the homologous protein.

3. Coding Sequences

Provided herein are coding sequences of antigens capable of eliciting an immune response in a mammal against one or more foot-and-mouth disease virus (FMDV) subtypes. The antigen may be a FMDV antigen comprising capsid protein VP1, VP2, VP3, VP4, a consensus thereof, a variant thereof, a fragment thereof or a combination thereof. The FMDV antigen may be from FMDV subtype A, Asia 1, C, O, SAT1, SAT2, or SAT3. The FMDV antigen may contain at least one antigenic epitope that may be effective against particular FMDV immunogens against which an immune response can be induced. The empty viral capsid proteins VP1-4 of the FMDV antigen provides an entire repertoire of immunogenic sites and epitopes present in an intact FMDV virus. The consensus FMDV antigen sequence may be derived from FMDV antigen sequences from a plurality of FMDV viruses of one FMDV subtype. The consensus FMDV antigen may comprise VP1, VP2, VP3, and VP4 FMDV subtype consensus protein sequences, which may be a consensus VP1-4 protein. The consensus VP1-4 protein may comprise at least one FMDV protein 3C cleavage site. The protein 3C cleavage site may be present in between each of consensus VP1, VP2, VP3, and VP4 sequences of the consensus VP1-4 protein. Cleavage of the consensus VP1-4 protein by protein 3C may cleave the consensus VP1-4 protein to produce a consensus VP1-, a consensus VP2-, a consensus VP3-, and a consensus VP4 protein. Alternatively, a native proteolytic cleavage site can be present in between each of the consensus antigen sequences, such as the amino acid sequence: SEQ ID NO:45: RGRKRRS.

Coding sequences for fusion proteins comprising consensus VP1, VP2, VP3 and VP4, and a consensus of protease 3C are provided. The are SEQ ID NOs: 1, 3, 5, 7, 9, 11 and 13 which encode consensus sequences of subtypes A, Asia 1, C, O, SAT1, SAT2 and SAT3 respectively.

SEQ ID NO:15 encodes a consensus 3C protease sequence.

Coding sequences for fusion proteins comprising consensus VP1, VP2, VP3 and VP4 are provided. The are SEQ ID NOs: 17, 19, 21, 23, 25, 27 and 29, which are consensus sequences of subtypes A, Asia 1, C, O, SAT1, SAT2 and SAT3 respectively.

SEQ ID NOs:31, 33, 35, and 37 encode consensus sequences for VPI subtypes Asia, O, A and C, respectively. These sequences include coding sequences for the IgE leader sequence SEQ ID NO:44 which may in each case be substituted with coding sequence for a different leader or deleted and substituted an initiation codon only.

SEQ ID NOs:40 and 42 are fusion proteins of two consensus sequences for VP1. SEQ ID NO:40 is consensus VP1 subtypes A and VP1 subtype C. SEQ ID NO:42 is consensus VP1 subtypes Asia and VP1 subtype O. These sequences include the IgE leader sequence SEQ ID NO:44 which may in each case can be substituted with coding sequence for a different leader or deleted and substituted an initiation codon only.

Additionally, coding sequences may encode proteins may be fragments of SEQ ID NOs: 2, 4, 6, 8, 10, 12, 14, 16, 18, 20, 22, 24, 26, 28, 30, 32, 34, 36, 38, 40 and 42. In some embodiments, coding sequences encode proteins that are 20% of the consensus protein. In some embodiments, coding sequences encode proteins that are 30% of the consensus protein. In some embodiments, coding sequences encode proteins that are 40% of the consensus protein. In some embodiments, coding sequences encode proteins that are 50% of the consensus protein. In some embodiments, coding sequences encode proteins that are 60% of the consensus protein. In some embodiments, coding sequences encode proteins that are 70% of the consensus protein. In some embodiments, coding sequences encode proteins that arc 850% of the consensus protein. In some embodiments, coding sequences encode proteins that are 90% of the consensus protein. In some embodiments, coding sequences encode proteins that are 95% of the consensus protein. In some embodiments, coding sequences encode proteins that are 96% of the consensus protein. In some embodiments, coding sequences encode proteins that are 97% of the consensus protein. I Additionally, coding sequences may encode proteins that are homologous to SEQ ID NOs: 2, 4, 6, 8, 10, 12, 14, 16, 18, 20, 22, 24, 26, 28, 30, 32, 34, 36, 38, 40 and 42. In some embodiments, coding sequences encode proteins that are 80% homologous. In some embodiments, coding sequences encode proteins that are 90% homologous. In some embodiments, coding sequences encode proteins that are 95% homologous. In some embodiments, coding sequences encode proteins that are 96% homologous. In some embodiments, coding sequences encode proteins that are 97% homologous. In some embodiments, coding sequences encode proteins that are 98% homologous. In some embodiments, coding sequences encode proteins that are 99% homologous.

Additionally, coding sequences encode proteins that are fragments of proteins homologous to SEQ ID NOs: 2, 4, 6, 8, 10, 12, 14, 16, 18, 20, 22, 24, 26, 28, 30, 32, 34, 36, 38, 40 and 42. In some embodiments, coding sequences encode proteins that are 20% of the homologous protein. In some embodiments, coding sequences encode proteins that are 30% of the homologous protein. In some embodiments, coding sequences encode proteins that are 40% of the homologous protein. In some embodiments, coding sequences encode proteins that are 50% of the homologous protein. In some embodiments, coding sequences encode proteins that are 60% of the homologous protein. In some embodiments, coding sequences encode proteins that are 70% of the homologous protein. In some embodiments, coding sequences encode proteins that arc 80% of the homologous protein. In some embodiments, coding sequences encode proteins that are 90% of the homologous protein. In some embodiments, coding sequences encode proteins that are 95% of the homologous protein. In some embodiments, coding sequences encode proteins that are 96% of the homologous protein. In some embodiments, coding sequences encode proteins that are 97% of the homologous protein. In some embodiments, coding sequences encode proteins that are 98% of the homologous protein. In some embodiments, coding sequences encode proteins that are 99% of the homologous protein.

Additionally, coding sequences may be fragments of SEQ ID NOs: 1, 3, 5, 7, 9, 11, 13, 15, 17, 19, 21, 23, 25, 27, 29, 31, 33, 35, 37, 39 and 41. In some embodiments, fragments are 20%, 30%, 40%, 50%, 60%, 70%, 80%, 90%, 95%, 96%, 97%, 98% or 99% of SEQ ID NOs: 1, 3, 5, 7, 9, 11, 13, 15, 17, 19, 21, 23, 25, 27, 29, 31, 33, 35, 37, 39 and 41.

Additionally, coding sequences may be homologous to SEQ ID NOs: 1, 3, 5, 7, 9, 11, 13, 15, 17, 19, 21, 23, 25, 27, 29, 31, 33, 35, 37, 39 and 41. In some embodiments, coding sequences are 80%, 90%, 95%, 96%, 97%, 98% or 99% homologous to SEQ ID NOs: 1, 3, 5, 7, 9, 11, 13, 15, 17, 19, 21, 23, 25, 27, 29, 31, 33, 35, 37, 39 and 41.

Additionally, coding sequences may be homologous to fragments of SEQ ID NOs: 1, 3, 5, 7, 9, 11, 13, 15, 17, 19, 21, 23, 25, 27, 29, 31, 33, 35, 37, 39 and 41. In some embodiments, fragments are 20%, 30%, 40%, 50%, 60%, 70%, 80%, 90%, 95%, 96%, 97%, 98% or 99% of SEQ ID NOs: 1, 3, 5, 7, 9, 11, 13, 15, 17, 19, 21, 23, 25, 27, 29, 31, 33, 35, 37, 39 and 41. and the coding sequences are 80%, 90%, 95%, 96%, 97%, 98% or 99% homologous to the fragments of SEQ ID NOs: 1, 3, 5, 7, 9, 11, 13, 15, 17, 19, 21, 23, 25, 27, 29, 31, 33, 35, 37, 39 and 41.

4. Plasmid

Provided herein is a vector that is capable of expressing one or more FMDV antigens in the cell of a mammal in a quantity effective to elicit an immune response in the mammal. The vector may comprise heterologous nucleic acid encoding the FMDV antigen. The vector may be a plasmid. The plasmid may be useful for transfecting cells with nucleic acid encoding a FMDV antigen, which the transformed host cell is cultured and maintained under conditions wherein expression of the FMDV antigen takes place.

The plasmid may comprise a nucleic acid encoding a FMDV antigen selected from the group consisting of: SEQ ID NOs: 2, 4, 6, 8, 10, 12, 14, 16, 18, 20, 22, 24, 26, 28, 30, 32, 34, 36, 38, 40 and 42, fragments thereof, homologous sequences thereof and fragments of homologous. The plasmid may further comprise an initiation codon or leader sequence, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence a may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon, which may allow more efficient transcription of the coding sequence in the host cell.

The coding sequence may comprise an Ig leader sequence. The leader sequence may be 5' of the coding sequence. The consensus protein encoded by this sequence may comprise an N-terminal Ig leader followed by a consensus protein. The N-terminal Ig leader may be IgE or IgG.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA T or pcDNA3 (Invitrogen, San Diego, Calif.), which maybe used for protein production in mammalian cells such as Chinese hamster ovary (CHO) cells.

Plasmids may comprise one or more coding sequences encoding one or more of VP1, VP2, VP3, VP4, and 3C from one or more subtypes such as Asia, A, O, C, SAT1, SAT2 and SAT3.

In some embodiments, a plasmid comprises coding sequences for multiple distinct consensus FMDV antigens VP1, VP2, VP3, VP4 and 3C from subtype Asia, A, O, C, SAT1, SAT2 or SAT3.

In some embodiments, a plasmid comprises coding sequences for multiple distinct consensus FMDV antigens VP1, VP2, VP3 and VP4 from subtype Asia, A, O, C, SAT1, SAT2 or SAT3.

In some embodiments, a plasmid comprises coding sequences for two distinct consensus FMDV antigen VP1 from two of subtypes Asia, A, O, and C such as VP1 from subtype Asia VP1 from subtype O, or a VP1 from t subtype A and VP1 from subtype C.

In some embodiments, a plasmid comprises coding sequences for a consensus FMDV antigen VP1 such as VP1 subtype Asia, VP1 subtype A, VP1 subtype 0 or VP1 subtype C.

The coding sequence can be encoded by a distinct DNA plasmid, all regulated by an operably linked promoter, e.g., a DNA plasmid having an encoding sequence regulated by one or mote promoters the encoding sequence comprising multiple consensus FMDV antigens.

5. Vaccine

While not being bound by scientific theory, a vaccine that can be used to elicit an immune response (humoral, cellular, or both) broadly against FMDV may comprise one or more coding sequences set forth above, i.e. nucleic acid sequences that encodes one or more proteins VP1, VP2, VP3, CVP4 and 3C from subtypes selected from the group consisting of: FMDV subtypes such as A, Asia 1, C, O, SAT1, SAT2, SAT3, or combinations thereof. Coding sequences may also include those that comprise homologous sequences, fragments, and homologous sequences of fragments. Alternatively or in addition, compositions which induce anti-FMDV immune response may comprise one or more proteins selected from the group consisting of: FMDV subtypes such as A, Asia 1, C, O, SAT1, SAT2, SAT3, or combinations thereof.

Provided herein is a vaccine capable of generating in a mammal an immune response against one or more FMDV subtypes. The vaccine may comprise the plasmid as discussed above. The vaccine may comprise a plurality of the plasmids each directed to one or more FMDV subtypes such as A, Asia 1, C, O, SAT1, SAT2, SAT3, or combinations thereof. The vaccine may also comprise the FMDV antigens themselves directed against one or more FMDV subtypes such as A, Asia 1, C, O, SAT1, SAT2, SAT3, or combinations thereof. The vaccine may also comprise plasmids directed to FMDV subtypes from particular regions in the world, for example, Asia, Europe and sub-Africa. Alternatively or in addition, the vaccine may comprise proteins of one or more FMDV subtypes such as A, Asia 1, C, O, SAT1, SAT2, SAT3, or combinations thereof. The vaccine may also comprise the FMDV antigens themselves directed against one or more FMDV subtypes such as A, Asia 1, C, O, SAT1, SAT2, SAT3, or combinations thereof. The vaccine may also comprise plasmids and/or proteins directed to FMDV subtypes from particular regions in the world, for example, Asia, Europe and sub-Africa. The vaccine may be provided to induce a therapeutic or prophylactic immune response.

The vaccine may also comprise a nucleic acid encoding a FMDV C3 protease, which may be a consensus C3 protease nucleic acid. The consensus protein 3C nucleic acid may be a protein 3C coding sequence. Alternatively or in addition, the vaccine may also comprise FMDV C3 protease, such as a consensus C3 protease for example a protein 3C. The vaccine may also comprise a chimeric gene encoding full or partial VP1-4 coding sequence and full or partial C3 coding sequence. Alternatively or in addition, the vaccine may also comprise a fusion protein comprising full or partial VP1-4 and full or partial C3.

Provided herein are pharmaceutical compositions according to the present invention which comprise about 1 nanogram to about 10 mg of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg. In some embodiments, pharmaceutical compositions according to the present invention comprise about 5 nanogram to about 10 mg of DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. Tn some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

Preferably the pharmaceutical composition is a vaccine, and more preferably a DNA vaccine.

The vaccine may be a DNA vaccine. The DNA vaccine may comprise a plurality of the same or different plasmids comprising nucleic acid coding sequences for one or more of consensus prostate antigens. The DNA vaccine may comprise one or more nucleic acid sequences that encode one or more of consensus prostate antigens. When the DNA vaccine comprises coding sequences of more than one consensus prostate antigens all such sequences may be present on a single plasmid, or each such sequences may be present on a different plasmids.

In some embodiments, vaccines may comprise nucleic acid sequences that encode one or more of consensus prostate antigens in combination with one or more of consensus prostate antigens.

DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome. The vaccine can be an RNA of the prostate antigen. The RNA vaccine can be introduced into the cell.

The vaccine can be a recombinant vaccine comprising the genetic construct or antigen described above. The vaccine can also comprise one or more consensus prostate antigens in the form of one or more protein subunits, or one or more attenuated viral particles comprising one or more consensus antigens. The attenuated vaccine can be attenuated live vaccines, killed vaccines and vaccines that use recombinant vectors to deliver foreign genes that encode one or more consensus prostate antigens, and well as subunit and protein vaccines. Examples of attenuated live vaccines, those using recombinant vectors to deliver prostate antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference. Vaccines may comprise plasmids in combination with other vaccine components such as FMDV proteins or expression vectors encoding proteins.

The vaccine provided may be used to induce immune responses including therapeutic or prophylactic immune responses. Antibodies and/or killer T cells may be generated which are directed to the consensus prostate antigen. Such antibodies and cells may be isolated.

The vaccine may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/nal, less than 0.100 mg/ml, less than 0.050 mg/ml, or less than 0.010 mg/ml.

The pharmaceutically acceptable excipient may be an adjuvant. The adjuvant may be other genes that are expressed in alternative plasmid or are delivered as proteins in combination with the plasmid above in the vaccine. The adjuvant may be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant may be IL-12, IL-15, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which may be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, TCAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. Vaccine may further comprise stabilizers including gelatin and albumin. The stabilizing may allow the formulation to be stable at room or ambient temperature for extended periods of time such as LGS or polycations or polyanions to the vaccine formulation.

6. Methods Of Delivery The Vaccine

Provided herein is a method for delivering the vaccine for providing genetic constructs and proteins of the FMDV antigen which comprise epitopes that make them particular effective against immunogens of FMDV against which an immune response can be induced. The method of delivering the vaccine or vaccination may be provided to induce a therapeutic and prophylactic immune response. The vaccination process may generate in the mammal an immune response against a plurality of FMDV subtypes. The vaccine may be delivered to an individual to modulate the activity of the mammal's immune system and enhance the immune response. The delivery of the vaccine may be the transfection of the FMDV antigen as a nucleic acid molecule that is expressed in the cell and delivered to the surface of the cell upon which the immune system recognized and induces a cellular, humoral, or cellular and humoral response. The delivery of the vaccine may be use to induce or elicit and immune response in mammals against a plurality of FMDV viruses by administering to the mammals the vaccine as discussed above.

Upon delivery of the vaccine and plasmid into the cells of the mammal, the transfected cells will express and secrete consensus capsids for each of the plasmids injected from the vaccine. These secreted capsid proteins will be recognized as foreign by the immune system and antibodies will be made against them. These antibodies will be maintained by the immune system and allow for rapid clearing of subsequent FMDV challenge.

The vaccine may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Combination Treatments

The vaccine may be administered in combination with other proteins or genes encoding α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80,CD86 including IL-15 having the signal sequence deleted and optionally including the signal peptide from IgE, IL-12, IL-15, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, INK, interferon response genes, NFkB, Bax, TRAIL, TRAILrec, TRAILrecDRCS, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. The vaccine may also be administered in combination with CTACK protein, TECK protein, MEC protein or functional fragments thereof.

The vaccine may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

The plasmid of the vaccine may be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The FMDV antigen may be delivered via DNA injection and along with in vivo electroporation.

b. Electroporation

Administration of the vaccine via electroporation of the plasmids of the vaccine may be accomplished using electroporation devices that can be configured to deliver to a desired tissue of a mammal a pulse of energy producing a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electronporation may be accomplished using the VGXP Cellectra™ system to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Method of Preparing Vaccine

Provided herein are methods for preparing the vaccine. In some embodiments, the methods are methods of preparing the vaccines comprising DNA plasmids. The DNA plasmids, after the final subcloning step into the mammalian expression plasmid, can be used to inoculate a cell culture in a large scale fermentation tank, using known methods in the art. The plasmid is transformed into a compatible host cell and cultured and maintained under conditions wherein expression of the FMDV antigen takes place. The FMDV antigen may be recovered from the culture either by lysing cells or from the culture medium and isolated. The isolated VP1-4 consensus proteins may be used in the vaccine as a natural source of antibodies. The FMDV antigen may be produce by recombinant techniques using automated synthesizers may also be employed to produce isolated essential pure FMDV antigen. These techniques may be useful for introducing variants of the FMDV antigen for particular subtypes of FMDV.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

d. Method for Preparing VP1-4 Expression Constructs

A multi-targeting FMDV DNA vaccine is constructed by first optimizing VP1, VP2, VP3, and VP4 amino acid sequences for one the FMDV subtypes Asia, O, A, C, SAT1, SAT2, and SAT3 using at least 10 different sequences from the subtype. Nucleic acids each encoding the subtype-optimized VP1-4 proteins are produced. The subtype-optimized VP1-4 nucleic acid sequences are cloned as a contiguous coding sequence, with the VPs separated by intervening FMDV protein 3C protease cleavage sites. The optimized VP1-4 coding sequence is inserted into an expression vector, either pVAX or pAV0242, under the control of an operator. An IgE leader sequence is placed upstream of the optimized VP1-4 coding sequence so that the encoded protein includes an N-terminal IgE leader. Two stop codons are placed at the 3' end of the VP1-4 coding sequence.

In addition, a nucleic acid encoding the FMDV protein 3C is constructed by optimizing the 3C nucleic acid sequence for one of the FMDV subtypes Asia 1, 0, A, C, SAT1, SAT2, and SAT3 using at least 10 different sequences from the subtype. A nucleic acid encoding the subtype-optimized 3C protein is produced, and cloned into a pVAX or pAV0242 plasmid.

e. Method of Using Vaccine as a Marker

Provided herein is also a method of differentiating between a vaccinated mammal with the vaccine and an infected mammal with FMDV. The method may comprise sample from a mammal and isolating the mammals antibodies from the sample. A mammal that has been vaccinated by the vaccine may have antibodies that are specific only for the empty capsid proteins of the FMDV antigen, i.c, viral coat proteins VP1-4 against FMDV subtypes A, Asia I, O, C, SAT1, SAT2, SAT3, or a combination thereof. A mammal that has been infected by FMDV will have antibodies against FMDV viral coat proteins VP1-4 of a particular FMDV subtype such as A, Asia 1, O, C, SAT1, SAT2, or SAT3 and in addition, against antibodies against the non-structural (NS) proteins of FMDV. The NS proteins of FMDV may include the protease 3C protease as well as FMDV protein 2C, 3A, 3B, and 3D (polymerase). The method may comprise identifying an antibody against a NS protein of FMDV such as the highly antigenic 3D protein. The method further comprises comparing to the sera sample of the vaccinated mammals to determine the presence or non-presence of FMDV NS proteins. The infected mammal has antibodies against the NS proteins of FMDV, while the vaccinated mammal does not have antibodies against the NS proteins as this mammal have a sufficient immunity against FMDV infection. The method may comprise differentiating mammals have antibodies to VP1-4 vs. mammals have antibodies to VP1-4 and the 3D polymerase of FMDV.

Generally, an agent may be used. The agent may be VP1-4 or a NS protein such as 3D polymerase. A sample from the mammal is isolated with FMDV antibodies and are reacted against the agent to identify the specificity of the FDMV antibody.

The sample of the method can be isolated from the mammal and may include a serum sample from blood, saliva, tears, cerebrospinal fluid, aqueous humor, pleural fluid, pericardial fluid, lymph node fluid, chime, chyle, bile, urine, synovial fluid, vomit, peritoneal fluid, stool water, semen, amniotic fluid, milk, scrum, interstitial fluid, and pancreatic juice.

Methods for performing the diagnostic test include performing a immunoprecipitation with [35S] methionine-labeled cell lysates from the mammal, western blots, and immunoblots to particular FMDV proteins such as VP1-4 and 3D polymerase.

The method of detecting described herein may be implemented in a variety of well-known detection systems to determine the presence of antibodies to FMDV VP1-4 or 3D polymerase in a test or control sample. The detection system may comprise a fluorescent or other means comparison between a signal generated from a detection label that is bound to a particular FMDV protein such as VP1-4 and 3D polymerase and a pre-determined value to determine the presence or absence of antibodies to FMDV VP1-4 or 3D polymerase in the test sample. The pre-determined value may be a ratio of the signal measured from the test sample to the signal measured from the control sample. In general, a test sample generating a signal that is three standard deviations above the mean signal measured from a control sample that contains no FMDV 3D polymerase antibodies that may be considered positive for FMDV 3D polymerase and therefore an infected mammal.

Alternatively, an apparatus such as a densitometer may be employed for measuring a numerical value of the detectable label. The pre-determined value may be determined using a Receive Operator Curve ("ROC") using the method of Sackett et al., *Clinical Epidemiology: A Basic Science for Clinical Medicine*, p. 106-107 (Little Brown and Co., 1985). The pre-determined value may be based upon relative light units by a fluorescent imager or other means as describe above. Briefly, the pre-determined value may be determined from a plot of pairs of true positive rates (namely, sensitivity) and false positive rates (namely, 100% specificity) that correspond to each possible value for the diagnostic test result. The pre-determined value on the plot that is the closest to the upper left-hand corner (namely, the value that encloses the largest area) is the most accurate pre-determined value, and a sample generating a signal that is higher than the pre-determined value determined by this method may be considered positive. Alternatively, the pre-determined value may be shifted to the left along the plot, to minimize the false positive rate.

(a) Immunoblot

The method of detecting may be used in an immunoblot detection system to detect antibodies to FMDV VP1-4 or 3D polymerase in a test or control sample. The immunoblot may use a solid support to immobilize the agent.

The immunoblot may use two separate control samples (namely, a first control and a second control), which may be immobilized on a solid support. The immunoblot may use three separate, discrete control samples (namely, a first control, a second control and a third control). If more than one control sample is present, then the controls may be identical to one another or different from one another. Two of the control samples may be identical (such as, for example, the first control and the second control). If two of the control samples are identical, the concentration of one of the control samples (either the first control or the second control or if three controls are present, the level of the first control or the third control or the second control or third control) may be higher (or greater) than the other control. The control sample may be in a higher concentration than the other control and may be referred to as the "high control". The control immobilized on the strip, disc or sheet in a lower concentration than the high control may be referred to as the "low control". The ratio of the concentration of low control to high control may be from about 1:2 to about 1:10, preferably, about 1:5 to about 1:6. For example, the first control may be the low control and the second control may be the high control. Alternatively, the first control may be the high control and the second control may be the low control. By way of another example, a three control detection system may comprise a low control and a high control as well a third control (which can be used, for example, to verify sample addition). The low control and high control may be human plasma (wherein the ratio of low control to high control is from about 1:2 to about 1:10) and the third control may be SDB Chagas or human plasma. In the flow-through format, an immobilized agent on the solid support may be immersed in a solution containing the test sample. Alternatively, the solid support may be placed in a reaction tray along with a diluent and then the test sample added to the reaction tray. The test sample and agent are allowed to incubate for a sufficient period of time using the same times and techniques described previously herein. Unbound test sample may be removed using the techniques described previously herein. In this format, anti-FDMV antibodies to VP1-4 or a NS structure protein such as 3D polymerase within the test sample may bind to the immobilized agent (and the at least one control) as the test sample passes through the membrane. At least one detection reagent (such as a detection reagent described previously herein containing a detectable label) may be added. At least one detection reagent may bind to each of the agent-antibody complexes formed as the solution containing the detection reagent flows through the strip. To determine the presence or absence of anti-FDMV antibodies to VP1-4 or a NS structure protein such as 3D polymerase in the test sample, the detection of the bound detection reagents may be performed as described above using the a cut-off or by comparing the intensity of one or more signals generated by one or more controls as discussed in more detail below.

When a low control and high control as described above may be used in the flow-through format, the presence or absence of the anti-FDMV antibodies to VP1-4 or a NS structure protein such as 3D polymerase in the test sample may be determined by identifying the presence of a signal from the detectable label at each of the test bands (or spots or dots) for the agents. If a signal is identified at a test band for a agent, then the intensity of this detected signal is compared with the intensity of the signal from the low control band (or spot or dot) and the high control band (or spot or dot), using a scale of 0 to 4+. The reading is 0 when no band is visible. The intensities of the low control band and high control band may be defined as 1+(for the low control) and 3+(for the high control), respectively. A test band with an intensity comparable to that of the low control would be rated 1+. A band with intensity between that of the low control and the high control band would be rated 2+. A band with an intensity comparable to that of the high control would be rated 3+. A band intensity higher than that of the high control would be rated 4+.

(b) Competitive Assay

The method of detecting may be used in a competitive detection system to identify test samples with anti-FDMV antibodies to VP1-4 or a NS structure protein such as 3D polymerase. The agent may be immobilized on a solid support as described above. The immobilized agent may then be contacted with a competitive antibody that is detectable labeled, known to bind the agent, and competes with anti-FDMV antibodies to VP1-4 or a NS structure protein such as 3D polymerase in the test sample. The immobilized agent is also contacted with the test sample. The signal from the detectably labeled antibody may be lower in test samples containing anti-FDMV antibodies to VP1-4 or a NS structure protein such as 3D polymerase because both sets of antibodies are competing for the immobilized agent.

f. Diagnostic Kit

Provided herein is a kit for performing the diagnostic method of identifying mammals that have been vaccinated with the vaccine vs. mammals infected with FMDV. The kit provides materials for allowing one to identify mammals that have been infected with FMDV to identify antibodies against the FS proteins including the 3D polymerase protein of FMDV vs. antibodies only to the empty capsid proteins VP1-4 of a vaccinated mammal. Test kits may include one or more reagents such as the agent useful for practicing one or more immunoassays according to the invention. A test kit generally includes a package with one or more containers holding the reagents, as one or more separate compositions or, optionally, as admixture where the compatibility of the reagents will allow. The test kit may also include other material(s), which may be desirable from a user standpoint, such as a buffer(s), a diluent(s), a standard(s), and/or any other material useful in sample processing, washing, or conducting any other step of the assay.

Kits according to the invention may include a solid phase and an agent affixed to a solid support. Kits may be employed for conducting sandwich immunoassays, and include a labeled detection antibody. The labeled detection antibody may be an anti-human IgG labeled antibody. The kit may further include a detectable label.

The test kit may include at least one direct label, such as acridinium-9-carboxamide. Test kits according to the invention may also include at least one indirect label. If the label employed generally requires an indicator reagent to produce a detectable signal, the test kit may include one or more suitable indicator reagents.

The test kit may include instructions for carrying out one or more of the immunoassays of the invention. Instructions included in kits of the invention may be affixed to packaging material or may be included as a package insert. While the instructions are typically written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

EXAMPLES

Example 1

Expression of Recombinant VP1-4

The subtype-optimized VP1-4 protein and optimized 3C protein are expressed by performing an in vitro translation assay using the optimized VP1-4 and 3C expression plasmids above. Translation of these proteins yields the expected bands on a SDS-PAGE gel.

To confirm expression of the VP1-4 proteins, a nucleic acid encoding a subtype-optimized VP1-4 protein and an N-terminal IgE leader is cloned into a HIS-tag bacterial expression vector. A nucleic acid encoding a subtype-optimized 3C protein is also cloned into a HIS-tag bacterial expression vector. The optimized VP1-4 and 3C proteins are expressed using a bacterial expression system, and affinity-purified using Ni-column separation. The purified proteins are analyzed using a SDS-PAGE gel. SDS-PAGE reveals the expected bands.

Example 2

Method of vaccination

To test the efficacy of the DNA plasmids, Balb/C mice are immunized with the optimized VP1-4- and 3C-encoding pVAX plasmids. Empty pVAX and human IL-15-encoding pVAX vectors are used as controls. The mice are immunized three times daily on Days 0, 14, and 28. Immunized mice are sacrificed 3 days after the final immunization. Sera from the mice are collected and analyzed for anti-VP1, -VP2, -VP3, and -VP4 ELISA. The HIS-tagged recombinant proteins from Example 1 are used as the capture antigen. Sera from pVAX control mice fail to recognize any of subtype-optimized VP1-4. In contrast, mice immunized with the subtype-optimized VP1-4 DNA vaccine developed antibodies toward subtype-optimized VP1, -2, -3, and -4, indicating that the optimized VP1-4 fusion vaccine is causing mice to mount an immune response against all four VPs.

Example 3

Preparing Expression Constructs

A multi-targeting FMD DNA vaccine was constructed. VP1 sequences from the subtypes Asia1, O, A, C, SAT1, SAT2, and SAT3 were first consensus optimized with at least 10 different sequences from each subtype. Thereafter, two VP1 sequences were inserted under one promoter and were separated by two consecutive cleavage sites.

An IgE leader sequence was inserted in front of the first ORF and two stop codons were inserted after the second ORF. The first plasmid encodes the Asia and O VP1, is 1362 bp.

The second plasmid, which encodes the A and C VP1, is 1356 bp. The third and fourth plasmids target the sub-African subtypes with the first encoding SAT1 and SAT2 VP1 and the second encoding SAT3 VP1.

Example 4

Expression of Recombinant VP1-4

The cloned plasmids were then expressed with an in vitro translation assay. Translation of all of the single VP1 constructs—A, Asia, C, and O—yielded the expected bands, [about 24.5 kDa] and the A+C VP1 and Asia+O VP1 constructs yielded a higher dimeric band. They constructs have FLAG-epitopes which were used in immunoprecipitation.

Example 5

Method of Vaccination

In order to confirm immune responses against FMD, we generated recombinant FMD VP1 proteins from all four VP1 subtypes (A, Asia, C, and O) Recombinant Consensus FMDV VP1 sequences (IgE Leader sequence is underlined at the N terminus)

The proteins were cloned into a HTS-tagged bacterial expression vector, and vector was expressed. The proteins were purified via Ni-column separation, and the expressed proteins are indicated with an arrow.

Next to test the efficacy of the DNA plasmids, Balb/C mice were immunized. Mice were immunized with 15 μg of DNA per immunization using CELLECTRA electroporation. There were 7 immunization groups:

1. pVax
2. pVax-FMDV VP1 A+pVAX1-IL-15
3. pVax-FMDV VP1 Asia+pVAX1-IL-15
4. pVax-FMDV VP1 C+pVAX1-IL-15
5. pVax-FMDV VP1 O+pVAX1-IL-15
6. pVax-FMDV VP1 A-C+pVAX1-IL-15
7. pVax-FMDV VP1 Asia-O+pVAX1-IL-15

The mice were immunized 3 times on day 0, 14, and 28, and were sacrificed 3 days after the last immunization. Sera from the animals were collected and analyzed for anti-VP1 ELISA. The recombinant proteins were used as the capture antigen. Sera from pVAX control mice failed to recognize A, Asia, C, and O VP1 proteins. Conversely, mice immunized with the A, Asia, C, and O DNA vaccines developed antibodies toward A, Asia, C, and O VP1 proteins, respectively. More importantly, mice immunized with either the VP1 A-C or AP1 Asia-O vaccines developed antibodies toward all 4 VP1 subtypes, suggesting that the consenus-VP1 fusion vaccine is generating immune responses against all 4 Asian-European FMD subtypes.

The invention claimed is:

1. An isolated nucleic acid comprising a nucleic acid sequence encoding a protein comprising a consensus VP1 of Asia subtype of FMDV and a consensus VP1 of O subtype of FMDV, wherein the protein is selected from the group consisting of: a protein comprising SEQ ID NO: 42 with or without a leader sequence, and a protein with 80% or more identity to SEQ ID NO: 42, wherein the protein induces an immune response against FMDV VP1.

2. The nucleic acid of claim 1, wherein the nucleic acid sequence is selected from the group consisting of: a nucleic acid sequence comprising SEQ ID NO: 41 with or without coding sequence for a leader sequence, and a nucleic acid sequence with 80% or more identity to SEQ ID NO: 41.

3. The nucleic acid of claim 1 wherein the nucleic acid sequence encodes a protein comprising SEQ ID NO: 42 with or without a leader sequence.

4. The nucleic acid of claim 1 wherein the nucleic acid sequence comprises SEQ ID NO: 41 with or without a coding sequence for a leader sequence.

5. The nucleic acid of claim 1 wherein the leader sequence is an Ige leader sequence.

6. The nucleic acid of claim 1 wherein said nucleic acid is a plasmid.

7. The nucleic acid of claim 1 wherein said nucleic acid is a plasmid that is an expression vector.

8. An immunogenic composition comprising a nucleic acid of claim 1 and/or a protein selected from the group consisting of SEQ ID NO: 42 with or without a leader sequence, a protein with 80% or more identity to SEQ ID NO: 42.

9. The immunogenic composition of claim 8 further comprising an adjuvant.

10. The immunogenic composition of claim 8 further comprising an adjuvant is selected from the group consisting of IL-12 and/or IL-15 or a nucleic acid sequence encoding IL-12 and/or IL-15.

11. A composition comprising one or more proteins selected from the group consisting of SEQ ID NO: 42 with or without a leader sequence, and a protein with 80% or more identity to SEQ ID NO: 42.

12. A method of eliciting an immune response against one or more FMDV virus subtypes in a mammal, comprising administering an immunogenic composition according to claim 8.

13. The method of claim 12 wherein the immunogenic composition comprises a nucleic acid molecule, the method comprising the steps of a) administering the nucleic acid molecule to the tissue of the mammal; and b) electroporating cells of the tissue with a pulse of energy at a constant current effective to permit entry of the nucleic acid molecule into the cells.

14. The method of claim 13 wherein step a) comprises injecting the immunogenic composition into intradermic, subcutaneous, or muscle tissue.

15. The method of claim 13 wherein the current is preset for delivering to the tissue and pulse of energy is at a constant current that equals the preset current.

16. The method of claim 13 wherein the electroporating step further comprises: (a) measuring the impedance in the electroporated cells; (b) adjusting the energy level of the pulse of energy relative to the measured impedance to maintain a constant current in the electroporated cells; wherein the measuring and adjusting steps occur within a lifetime of the pulse of energy.

17. The method of claim 13 wherein the electroporation step comprise delivering the pulse of energy to a plurality of electrodes according to a pulse sequence pattern that delivers the pulse of energy in a decentralized pattern.

18. The method of claim 12 wherein the mammal has not been infected with FMDV and the immune response is a protective immune response.

19. The method of claim 12, wherein the mammal has been infected with FMDV and the immune response is a therapeutic immune response.

20. A method of diagnosing a mammals infected with FMDV in mammal vaccinated with a vaccine of claim 8, the method comprising:
 a) isolating a fluid sample from the mammal; and
 b) detecting the presence of FMDV proteins not included in said vaccine and/or antibodies against FMDV proteins not included in said vaccine, wherein the presence of FMDV proteins not included in said vaccine and/or antibodies against FMDV proteins not included in said vaccine indicates the mammal has been infected with FM DV.

\* \* \* \* \*

SEQUENCE LISTING

```
<160> NUMBER OF SEQ ID NOS: 49

<210> SEQ ID NO 1
<211> LENGTH: 2916
<212> TYPE: DNA
<213> ORGANISM: Artificial Sequence
<220> FEATURE:
<223> OTHER INFORMATION: Plasmid Sequence 1

<400> SEQUENCE: 1
atgctgaacg gcgactggaa ggccaaggtg cagcgcaagc tgaagggcgc cggccagagc      60
agccccgcca ccggcagcca gaaccagagc ggcaacaccg gcagcatcat caacaactac     120
tacatgcagc agtaccagaa cagcatggac acccagctgg gcgacaacgc catcagcggc     180
ggcagcaacg agggcagcac cgacaccacc agcacccaca ccaccaacac ccagaacaac     240
gactggttca gcaagctggc cagcagcgcc ttcaccggcc tgttcggcgc cctgctggcc     300
gacaagaaga ccgaggagac caccctgctg gaggaccgca tcctgaccac ccgcaacggc     360
cacaccacca gcaccaccca gagcagcgtg ggcgtgacct acggctacag caccaccgag     420
gaccacgtgg ccggccccaa caccagcggc ctggagaccc gcgtggtgca ggccgagcgc     480
ttcttcaaga agttcctgtt cgactggacc accgacaagc ccttcggcca cctgcacaag     540
ctggagctgc ccaccgacca ccacggcgtg ttcggccacc tggtggacag ctacgcctac     600
atgcgcaacg gctgggacgt ggaggtgagc gccgtgggca accagttcaa cggcggctgc     660
ctgctggtgg ccatggtgcc cgagtggaag gagttcgaca cccgcgagaa gtaccagctg     720
accctgttcc cccaccagtt catcagcccc cgcaccaaca tgaccgccca catcaccgtg     780
ccctacctgg gcgtgaaccg ctacgaccag tacaagaagc acaagccctg gaccctggtg     840
gtgatggtgg tgagccccct gaccgtgaac accgccgccc agatcaaggt gtacgccaac     900 atcgcccca cctacgtgca cgtggccggc gagctgccca gcaaggaggg catcttcccc     960
gtggcctgcg ccgacggcta cggcggcctg gtgaccaccg accccaagac cgccgacccc    1020
gcctacgcca aggtgtacaa cccccccgc accaactacc ccggccgctt caccaacctg    1080
ctggacgtgg ccgaggcctg ccccaccttc tgtgcttcg acgacggcaa gccctacgtg    1140 accaccgca ccgacgagac ccgcctgctg gccaagttcg acgtgagcct ggccgccaag    1200
cacatgagca cacctacct gagcggcatc gcccagtact acacccagta cagcggcacc    1260
atcaacctgc acttcatgtt caccggcagc accgacagca ggcccgcta catggtggcc    1320
```

-continued

```
tacatccccc ccggcgtgga gacccccccc gacacccccg agcgcgccgc ccactgcatc   1380
cacgccgagt gggacaccgg cctgaacagc aagttcacct tcagcatccc ctacgtgagc   1440
gccgccgact acgcctacac cgccagcgac accgccgaga ccaccaacgt gcagggctgg   1500
gtgtgcgtgt accagatcac ccacggcaag gccgagaacg acaccctggt ggtgagcgtg   1560
agcgccggca aggacttcga gctgcgcctg cccatcgacc cccgccagca gaccaccgcc   1620
accggcgaga gcgccgaccc cgtgaccacc accgtggaga actacggcgg cgagacccag   1680
gtgcagcgcc gccaccacac cgacgtgggc ttcatcatgg accgcttcgt gaagatcaac   1740
agccccaagc ccacccacgt gatcgacctg atgcagaccc accagcacgg cctggtgggc   1800
gccctgctgc gcgccgccac ctactacttc agcgacctgg agatcgtggt gcgccacgac   1860
ggcctgacct gggtgcccaa cggcgccccc gagagcgccc tgagcaacac cagcaacccc   1920
accgcctaca acaaggcccc cttcacccgc ctggccctgc cctacaccgc cccccaccgc   1980
gtgctggcca ccgtgtacaa cggcaccagc aagtacaccg tgagcggcag cagccgccgc   2040
ggcgacctgg gcagcctggc cgcccgcgtg gccaagcagc tgcccgccag cttcaactac   2100
ggcgccatca aggccgacac catccacgag ctgctggtgc gcatgaagcg cgccgagctg   2160
tactgcgtga agaagcccgt ggccctgaag gtgaaggcca agaacaccct gatcgtgacc   2220
gagagcggcg cccccccccac cgacctgcag aagatggtga tgggcaacac caagcccgtg   2280
gagctgatcc tggacggcaa gaccgtggcc atctgctgcg ccaccggcgt gttcggcacc   2340
gcctacctgg tgccccgcca cctgttcgcc gagaagtacg acaagatcat gctggacggc   2400
cgcgccatga ccgacagcga ctaccgcgtg ttcgagttcg agatcaaggt gaagggccag   2460
gacatgctga gcgacgccgc cctgatggtg ctgcaccgcg gcaaccgcgt gcgcgacatc   2520
accaagcact tccgcgacac cgcccgcatg aagaagggca cccccgtggt gggcgtgatc   2580
aacaacgccg acgtgggccg cctgatcttc agcggcgagg ccctgaccta caaggacatc   2640
gtggtgtgca tggacggcga caccatgccc ggcctgttcg cctacaaggc cgccaccaag   2700
gccggctact gcggcggcgc cgtgctggcc aaggacggcg ccgacacctt catcgtgggc   2760
acccacagcg ccggcggccg caacggcgtg ggctactgca gctgcgtgag ccgcagcatg   2820
ctgctgaaga tgaaggccca catcgacccc gagccccacc acgagggcct gatcgtggac   2880
acccgcgacg tggaggagcg cgtgcacgtg atgtga                              2916
```

<210> SEQ ID NO 2
<211> LENGTH: 971
<212> TYPE: PRT
<213> ORGANISM: Artificial Sequence
<220> FEATURE:
<223> OTHER INFORMATION: consensus VP1-VP4 subtype A and consensus C3

<400> SEQUENCE: 2

```
Met Leu Asn Gly Asp Trp Lys Ala Lys Val Gln Arg Lys Leu Lys Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Thr Asn Thr Gln Asn Asn
65                  70                  75                  80
```

```
Asp Trp Phe Ser Lys Leu Ala Ser Ser Ala Phe Thr Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg Asn Gly His Thr Thr Ser Thr Thr Gln Ser
            115                 120                 125

Ser Val Gly Val Thr Tyr Gly Tyr Ser Thr Thr Glu Asp His Val Ala
            130                 135                 140

Gly Pro Asn Thr Ser Gly Leu Glu Thr Arg Val Val Gln Ala Glu Arg
145                 150                 155                 160

Phe Phe Lys Lys Phe Leu Phe Asp Trp Thr Thr Asp Lys Pro Phe Gly
                165                 170                 175

His Leu His Lys Leu Glu Leu Pro Thr Asp His His Gly Val Phe Gly
                180                 185                 190

His Leu Val Asp Ser Tyr Ala Tyr Met Arg Asn Gly Trp Asp Val Glu
                195                 200                 205

Val Ser Ala Val Gly Asn Gln Phe Asn Gly Gly Cys Leu Leu Val Ala
            210                 215                 220

Met Val Pro Glu Trp Lys Glu Phe Asp Thr Arg Glu Lys Tyr Gln Leu
225                 230                 235                 240

Thr Leu Phe Pro His Gln Phe Ile Ser Pro Arg Thr Asn Met Thr Ala
                245                 250                 255

His Ile Thr Val Pro Tyr Leu Gly Val Asn Arg Tyr Asp Gln Tyr Lys
                260                 265                 270

Lys His Lys Pro Trp Thr Leu Val Met Val Val Ser Pro Leu Thr
                275                 280                 285

Val Asn Thr Ala Ala Gln Ile Lys Val Tyr Ala Asn Ile Ala Pro Thr
            290                 295                 300

Tyr Val His Val Ala Gly Glu Leu Pro Ser Lys Glu Gly Ile Phe Pro
305                 310                 315                 320

Val Ala Cys Ala Asp Gly Tyr Gly Gly Leu Val Thr Thr Asp Pro Lys
                325                 330                 335

Thr Ala Asp Pro Ala Tyr Gly Lys Val Tyr Asn Pro Pro Arg Thr Asn
                340                 345                 350

Tyr Pro Gly Arg Phe Thr Asn Leu Leu Asp Val Ala Glu Ala Cys Pro
            355                 360                 365

Thr Phe Leu Cys Phe Asp Asp Gly Lys Pro Tyr Val Thr Thr Arg Thr
370                 375                 380

Asp Glu Thr Arg Leu Leu Ala Lys Phe Asp Val Ser Leu Ala Ala Lys
385                 390                 395                 400

His Met Ser Asn Thr Tyr Leu Ser Gly Ile Ala Gln Tyr Tyr Thr Gln
                405                 410                 415

Tyr Ser Gly Thr Ile Asn Leu His Phe Met Phe Thr Gly Ser Thr Asp
            420                 425                 430

Ser Lys Ala Arg Tyr Met Val Ala Tyr Ile Pro Pro Gly Val Glu Thr
            435                 440                 445

Pro Pro Asp Thr Pro Glu Arg Ala Ala His Cys Ile His Ala Glu Trp
450                 455                 460

Asp Thr Gly Leu Asn Ser Lys Phe Thr Phe Ser Ile Pro Tyr Val Ser
465                 470                 475                 480

Ala Ala Asp Tyr Ala Tyr Thr Ser Asp Thr Ala Glu Thr Thr Asn
                485                 490                 495
```

```
-continued

Val Gln Gly Trp Val Cys Val Tyr Gln Ile Thr His Gly Lys Ala Glu
                500                 505                 510

Asn Asp Thr Leu Val Val Ser Val Ser Ala Gly Lys Asp Phe Glu Leu
            515                 520                 525

Arg Leu Pro Ile Asp Pro Arg Gln Gln Thr Thr Ala Thr Gly Glu Ser
        530                 535                 540

Ala Asp Pro Val Thr Thr Thr Val Glu Asn Tyr Gly Gly Glu Thr Gln
545                 550                 555                 560

Val Gln Arg Arg His His Thr Asp Val Gly Phe Ile Met Asp Arg Phe
                565                 570                 575

Val Lys Ile Asn Ser Pro Lys Pro Thr His Val Ile Asp Leu Met Gln
            580                 585                 590

Thr His Gln His Gly Leu Val Gly Ala Leu Leu Arg Ala Ala Thr Tyr
        595                 600                 605

Tyr Phe Ser Asp Leu Glu Ile Val Val Arg His Asp Gly Leu Thr Trp
610                 615                 620

Val Pro Asn Gly Ala Pro Glu Ser Ala Leu Ser Asn Thr Ser Asn Pro
625                 630                 635                 640

Thr Ala Tyr Asn Lys Ala Pro Phe Thr Arg Leu Ala Leu Pro Tyr Thr
                645                 650                 655

Ala Pro His Arg Val Leu Ala Thr Val Tyr Asn Gly Thr Ser Lys Tyr
            660                 665                 670

Thr Val Ser Gly Ser Ser Arg Arg Gly Asp Leu Gly Ser Leu Ala Ala
        675                 680                 685

Arg Val Ala Lys Gln Leu Pro Ala Ser Phe Asn Tyr Gly Ala Ile Lys
690                 695                 700

Ala Asp Thr Ile His Glu Leu Leu Val Arg Met Lys Arg Ala Glu Leu
705                 710                 715                 720

Tyr Cys Val Lys Lys Pro Val Ala Leu Lys Val Lys Ala Lys Asn Thr
                725                 730                 735

Leu Ile Val Thr Glu Ser Gly Ala Pro Pro Thr Asp Leu Gln Lys Met
            740                 745                 750

Val Met Gly Asn Thr Lys Pro Val Glu Leu Ile Leu Asp Gly Lys Thr
        755                 760                 765

Val Ala Ile Cys Cys Ala Thr Gly Val Phe Gly Thr Ala Tyr Leu Val
770                 775                 780

Pro Arg His Leu Phe Ala Glu Lys Tyr Asp Lys Ile Met Leu Asp Gly
785                 790                 795                 800

Arg Ala Met Thr Asp Ser Asp Tyr Arg Val Phe Glu Phe Glu Ile Lys
                805                 810                 815

Val Lys Gly Gln Asp Met Leu Ser Asp Ala Ala Leu Met Val Leu His
            820                 825                 830

Arg Gly Asn Arg Val Arg Asp Ile Thr Lys His Phe Arg Asp Thr Ala
        835                 840                 845

Arg Met Lys Lys Gly Thr Pro Val Val Gly Val Ile Asn Asn Ala Asp
850                 855                 860

Val Gly Arg Leu Ile Phe Ser Gly Glu Ala Leu Thr Tyr Lys Asp Ile
865                 870                 875                 880

Val Val Cys Met Asp Gly Asp Thr Met Pro Gly Leu Phe Ala Tyr Lys
                885                 890                 895

Ala Ala Thr Lys Ala Gly Tyr Cys Gly Gly Ala Val Leu Ala Lys Asp
            900                 905                 910

Gly Ala Asp Thr Phe Ile Val Gly Thr His Ser Ala Gly Gly Arg Asn
```

-continued

```
        915                 920                 925

Gly Val Gly Tyr Cys Ser Cys Val Ser Arg Ser Met Leu Leu Lys Met
    930                 935                 940

Lys Ala His Ile Asp Pro Glu Pro His His Glu Gly Leu Ile Val Asp
945                 950                 955                 960

Thr Arg Asp Val Glu Glu Arg Val His Val Met
                965                 970

<210> SEQ ID NO 3
<211> LENGTH: 2916
<212> TYPE: DNA
<213> ORGANISM: Artificial Sequence
<220> FEATURE:
<223> OTHER INFORMATION: plasmid 2 consensus VP1-VP4 subtype Asia 1 and
      consensus C3

<400> SEQUENCE: 3
atgctgaacg gcgagtggaa ggccaaggtg cagaagcgcc tgaagggcgc cggccagagc     60
agccccgcca ccggcagcca gaaccagagc ggcaacaccg gcagcatcat caacaactac    120
tacatgcagc agtaccagaa cagcatggac acccagctgg gcgacaacgc catcagcggc    180
ggcagcaacg agggcagcac cgacaccacc agcacccaca ccaacaacac ccagaacaac    240
gactggttca gccgcctggc cagcagcgcc ttcagcggcc tgttcggcgc cctgctggcc    300
gacaagaaga ccgaggagac caccctgctg gaggaccgca tcctgaccac ccgcaacggc    360
cacaccacca gcaccaccca gagcagcgtg ggcgtgacct acggctacgc cgtggccgag    420
gacgccgtga gcggccccaa caccagcggc ctggagaccc gcgtgcagca ggccgagcgc    480
ttcttcaaga agcacctgtt cgactggacc cccaacctgg ccttcggcca ctgccactac    540
ctggagctgc ccaccgagca caagggcgtg tacggcagcc tgatggacag ctacgcctac    600
atgcgcaacg gctgggacat cgaggtgacc gccgtgggca accagttcaa cggcggctgc    660
ctgctggtgg ccctggtgcc cgagctgaag agcctggaca cccgccagaa gtaccagctg    720
accctgttcc cccaccagtt catcaacccc cgcaccaaca tgaccgccca catcaacgtg    780
cccttcgtgg gcgtgaaccg ctacgaccag tacgccctgc acaagccctg gaccctggtg    840
gtgatggtgg tggccccccct gaccgtgaag accggcggca gcgagcagat caaggtgtac    900
atgaacgccg cccccaccta cgtgcacgtg gccggcgagc tgcccagcaa ggagggcatc    960
gtgcccgtgg cctgcgccga cggctacggc aacatggtga ccaccgaccc caagaccgcc   1020
gaccccgtgt acggcaaggt gttcaacccc ccccgcacca acctgcccgg ccgcttcacc   1080
aacttcctgg acgtggccga ggcctgcccc accttcctgc gcttcggcga ggtgcccttc   1140
gtgaagaccg tgaacagcgg cgaccgcctg ctggccaagt tcgacgtgag cctggccgcc   1200
ggccacatga gcaacaccta cctggccggc ctggcccagt actacaccca gtacagcggc   1260
accatgaacg tgcacttcat gttcaccggc cccaccgacg ccaaggcccg ctacatggtg   1320
gcctacatcc cccccggcat gacccccccc accgaccccg agcgcgccgc ccactgcatc   1380
cacagcgagt gggacaccgg cctgaacagc aagttcacct tcagcatccc ctacctgagc   1440
gccgccgact acgcctacac cgccagcgac accgccgaga ccaccagcgt gcagggctgg   1500
gtgtgcatct accagatcac ccacggcaag gccgagggcg acgccctggt ggtgagcgtg   1560
agcgccggca aggacttcga gttccgcctg cccgtggacg cccgccgcca gaccaccacc   1620
accggcgaga gcgccgaccc cgtgaccacc accgtggaga actacggcgg cgagacccag   1680
accgcccgcc gcctgcacac cgacgtggcc ttcgtgctgg accgcttcgt gaagctgacc   1740
```

```
gcccccaaga acacccagac cctggacctg atgcagatcc ccagccacac cctggtgggc    1800
gccctgctgc gcagcgccac ctactacttc agcgacctgg aggtggccct ggtgcacacc    1860
ggccccgtga cctgggtgcc aacggcagc cccaaggacg ccctggacaa ccagaccaac    1920
cccaccgcct accagaagca gcccatcacc cgcctggccc tgcctacac cgcccccac    1980 cgcgtgctgg ccaccgtgta acggcaag accacctacg gcgagacccc cagccgccgc    2040
ggcgacatgg ccgccctggc ccagcgcctg agcgagcgcc tgcccaccag cttcaactac    2100
ggcgccgtga aggccgagac catcaccgag ctgctgatcc gcatgaagcg cgccgagacc    2160
tactgcgtga agaagcccgt ggccctgaag gtgaaggcca agaacaccct gatcgtgacc    2220
gagagcggcg ccccccccac cgacctgcag aagatggtga tgggcaacac caagcccgtg    2280
gagctgatcc tggacggcaa gaccgtggcc atctgctgcg ccaccggcgt gttcggcacc    2340
gcctacctgg tgccccgcca cctgttcgcc gagaagtacg acaagatcat gctggacggc    2400
cgcgccatga ccgacagcga ctaccgcgtg ttcgagttcg agatcaaggt gaagggccag    2460
gacatgctga gcgacgccgc cctgatggtg ctgcaccgcg gcaaccgcgt gcgcgacatc    2520
accaagcact ccgcgacac cgcccgcatg aagaagggca ccccgtggt gggcgtgatc    2580 aacaacgccg acgtgggccg cctgatcttc agcggcgagg ccctgaccta caaggacatc    2640
gtggtgtgca tggacggcga caccatgccc ggcctgttcg cctacaaggc cgccaccaag    2700
gccggctact gcggcggcgc cgtgctggcc aaggacggcg ccgacaccct catcgtgggc    2760
acccacagcg ccggcggccg caacggcgtg ggctactgca gctgcgtgag ccgcagcatg    2820
ctgctgaaga tgaaggccca catcgacccc gagccccacc acgagggcct gatcgtggac    2880
acccgcgacg tggaggagcg cgtgcacgtg atgtga                              2916
```

<210> SEQ ID NO 4
<211> LENGTH: 971
<212> TYPE: PRT
<213> ORGANISM: Artificial Sequence
<220> FEATURE:
<223> OTHER INFORMATION: consensus VP1-VP4 subtype Asia 1 and consensus C3

<400> SEQUENCE: 4

```
Met Leu Asn Gly Glu Trp Lys Ala Lys Val Gln Lys Arg Leu Lys Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Asn Asn Thr Gln Asn Asn
65                  70                  75                  80

Asp Trp Phe Ser Arg Leu Ala Ser Ser Ala Phe Ser Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg Asn Gly His Thr Thr Ser Thr Thr Gln Ser
        115                 120                 125

Ser Val Gly Val Thr Tyr Gly Tyr Ala Val Ala Glu Asp Ala Val Ser
    130                 135                 140
```

```
Gly Pro Asn Thr Ser Gly Leu Glu Thr Arg Val Gln Gln Ala Glu Arg
145                 150                 155                 160

Phe Phe Lys Lys His Leu Phe Asp Trp Thr Pro Asn Leu Ala Phe Gly
            165                 170                 175

His Cys His Tyr Leu Glu Leu Pro Thr Glu His Lys Gly Val Tyr Gly
            180                 185                 190

Ser Leu Met Asp Ser Tyr Ala Tyr Met Arg Asn Gly Trp Asp Ile Glu
        195                 200                 205

Val Thr Ala Val Gly Asn Gln Phe Asn Gly Gly Cys Leu Leu Val Ala
    210                 215                 220

Leu Val Pro Glu Leu Lys Ser Leu Asp Thr Arg Gln Lys Tyr Gln Leu
225                 230                 235                 240

Thr Leu Phe Pro His Gln Phe Ile Asn Pro Arg Thr Asn Met Thr Ala
            245                 250                 255

His Ile Asn Val Pro Phe Val Gly Val Asn Arg Tyr Asp Gln Tyr Ala
            260                 265                 270

Leu His Lys Pro Trp Thr Leu Val Val Met Val Val Ala Pro Leu Thr
        275                 280                 285

Val Lys Thr Gly Gly Ser Glu Gln Ile Lys Val Tyr Met Asn Ala Ala
    290                 295                 300

Pro Thr Tyr Val His Val Ala Gly Glu Leu Pro Ser Lys Glu Gly Ile
305                 310                 315                 320

Val Pro Val Ala Cys Ala Asp Gly Tyr Gly Asn Met Val Thr Thr Asp
            325                 330                 335

Pro Lys Thr Ala Asp Pro Val Tyr Gly Lys Val Phe Asn Pro Pro Arg
            340                 345                 350

Thr Asn Leu Pro Gly Arg Phe Thr Asn Phe Leu Asp Val Ala Glu Ala
        355                 360                 365

Cys Pro Thr Phe Leu Arg Phe Gly Glu Val Pro Phe Val Lys Thr Val
    370                 375                 380

Asn Ser Gly Asp Arg Leu Leu Ala Lys Phe Asp Val Ser Leu Ala Ala
385                 390                 395                 400

Gly His Met Ser Asn Thr Tyr Leu Ala Gly Leu Ala Gln Tyr Tyr Thr
            405                 410                 415

Gln Tyr Ser Gly Thr Met Asn Val His Phe Met Phe Thr Gly Pro Thr
            420                 425                 430

Asp Ala Lys Ala Arg Tyr Met Val Ala Tyr Ile Pro Pro Gly Met Thr
        435                 440                 445

Pro Pro Thr Asp Pro Glu Arg Ala Ala His Cys Ile His Ser Glu Trp
    450                 455                 460

Asp Thr Gly Leu Asn Ser Lys Phe Thr Phe Ser Ile Pro Tyr Leu Ser
465                 470                 475                 480

Ala Ala Asp Tyr Ala Tyr Thr Ala Ser Asp Thr Ala Glu Thr Thr Ser
            485                 490                 495

Val Gln Gly Trp Val Cys Ile Tyr Gln Ile Thr His Gly Lys Ala Glu
            500                 505                 510

Gly Asp Ala Leu Val Val Ser Val Ser Ala Gly Lys Asp Phe Glu Phe
        515                 520                 525

Arg Leu Pro Val Asp Ala Arg Gln Thr Thr Thr Thr Gly Glu Ser
    530                 535                 540

Ala Asp Pro Val Thr Thr Thr Val Glu Asn Tyr Gly Gly Glu Thr Gln
545                 550                 555                 560

Thr Ala Arg Arg Leu His Thr Asp Val Ala Phe Val Leu Asp Arg Phe
```

```
                          565                 570                 575
Val Lys Leu Thr Ala Pro Lys Asn Thr Gln Thr Leu Asp Leu Met Gln
                580                 585                 590

Ile Pro Ser His Thr Leu Val Gly Ala Leu Leu Arg Ser Ala Thr Tyr
            595                 600                 605

Tyr Phe Ser Asp Leu Glu Val Ala Leu Val His Thr Gly Pro Val Thr
        610                 615                 620

Trp Val Pro Asn Gly Ser Pro Lys Asp Ala Leu Asp Asn Gln Thr Asn
625                 630                 635                 640

Pro Thr Ala Tyr Gln Lys Gln Pro Ile Thr Arg Leu Ala Leu Pro Tyr
                645                 650                 655

Thr Ala Pro His Arg Val Leu Ala Thr Val Tyr Asn Gly Lys Thr Thr
            660                 665                 670

Tyr Gly Glu Thr Pro Ser Arg Arg Gly Asp Met Ala Ala Leu Ala Gln
        675                 680                 685

Arg Leu Ser Glu Arg Leu Pro Thr Ser Phe Asn Tyr Gly Ala Val Lys
690                 695                 700

Ala Glu Thr Ile Thr Glu Leu Leu Ile Arg Met Lys Arg Ala Glu Thr
705                 710                 715                 720

Tyr Cys Val Lys Lys Pro Val Ala Leu Lys Val Lys Ala Lys Asn Thr
                725                 730                 735

Leu Ile Val Thr Glu Ser Gly Ala Pro Pro Thr Asp Leu Gln Lys Met
            740                 745                 750

Val Met Gly Asn Thr Lys Pro Val Glu Leu Ile Leu Asp Gly Lys Thr
        755                 760                 765

Val Ala Ile Cys Cys Ala Thr Gly Val Phe Gly Thr Ala Tyr Leu Val
        770                 775                 780

Pro Arg His Leu Phe Ala Glu Lys Tyr Asp Lys Ile Met Leu Asp Gly
785                 790                 795                 800

Arg Ala Met Thr Asp Ser Asp Tyr Arg Val Phe Glu Phe Glu Ile Lys
                805                 810                 815

Val Lys Gly Gln Asp Met Leu Ser Asp Ala Ala Leu Met Val Leu His
            820                 825                 830

Arg Gly Asn Arg Val Arg Asp Ile Thr Lys His Phe Arg Asp Thr Ala
        835                 840                 845

Arg Met Lys Lys Gly Thr Pro Val Val Gly Val Ile Asn Asn Ala Asp
850                 855                 860

Val Gly Arg Leu Ile Phe Ser Gly Glu Ala Leu Thr Tyr Lys Asp Ile
865                 870                 875                 880

Val Val Cys Met Asp Gly Asp Thr Met Pro Gly Leu Phe Ala Tyr Lys
                885                 890                 895

Ala Ala Thr Lys Ala Gly Tyr Cys Gly Gly Ala Val Leu Ala Lys Asp
            900                 905                 910

Gly Ala Asp Thr Phe Ile Val Gly Thr His Ser Ala Gly Gly Arg Asn
        915                 920                 925

Gly Val Gly Tyr Cys Ser Cys Val Ser Arg Ser Met Leu Leu Lys Met
        930                 935                 940

Lys Ala His Ile Asp Pro Glu Pro His His Glu Gly Leu Ile Val Asp
945                 950                 955                 960

Thr Arg Asp Val Glu Glu Arg Val His Val Met
                965                 970

<210> SEQ ID NO 5
```

<211> LENGTH: 2913
<212> TYPE: DNA
<213> ORGANISM: Artificial Sequence
<220> FEATURE:
<223> OTHER INFORMATION: plasmid 3 consensus VP1-VP4 subtype C and consensus C3

<400> SEQUENCE: 5
atgctgaacg agggctggaa ggccagcgtg cagcgcaagc tgaagggcgc cggccagagc 60
agccccgcca ccggcagcca gaaccagagc ggcaacaccg gcagcatcat caacaactac 120
tacatgcagc agtaccagaa cagcatggac acccagctgg gcgacaacgc catcagcggc 180
ggcagcaacg agggcagcac cgacaccacc agcacccaca ccaccaacac ccagaacaac 240
gactggttca gcaagctggc cagcagcgcc ttcagcggcc tgttcggcgc cctgctggcc 300
gacaagaaga ccgaggagac caccctgctg gaggaccgca tcctgaccac ccgcaacggc 360
cacaccacca gcaccaccca gagcagcgtg ggcgtgacct tcggctacgc caccgccgag 420
gacagcacca gcggccccaa caccagcggc ctggagaccc gcgtgcacca ggccgagcgc 480
ttcttcaaga tggccctgtt cgactgggtg cccagccaga acttcggcca catgcacaag 540
gtggtgctgc cccacgagcc caagggcgtg tacggcggcc tggtgaagag ctacgcctac 600
atgcgcaacg gctgggacgt ggaggtgacc gccgtgggca accagttcaa cggcggctgc 660
ctgctggtgg ccctggtgcc cgagatgggc gacatcagcg accgcgagaa gtaccagctg 720
accctgtacc cccaccagtt catcaacccc cgcaccaaca tgaccgccca catcaccgtg 780
ccctacgtgg gcgtgaaccg ctacgaccag tacaagcagc accgcccctg gaccctggtg 840
gtgatggtgg tggccccccct gaccaccaac accgccggcg cccagcagat caaggtgtac 900
gccaacatcg cccccaccaa cgtgcacgtg gccggcgagc tgcccagcaa ggagggcatc 960
ttccccgtgg cctgcagcga cggctacggc aacatggtga ccaccgaccc caagaccgcc 1020
gaccccgtgt acggcaaggt gtacaacccc ccccgcaccg ccctgcccgg ccgcttcacc 1080
aactacctgg acgtggccga ggcctgcccc accttcctga tgttcgagaa cgtgccctac 1140
gtgagcaccc gcaccgacgg ccagcgcctg ctggccaagt tcgacgtgag cctggccgcc 1200
aagcacatga gcaacaccta cctggccggc ctggcccagt actacaccca gtacaccggc 1260
accatcaacc tgcacttcat gttcaccggc cccaccgacg ccaaggcccg ctacatggtg 1320
gcctacgtgc cccccggcat ggacgccccc gacaaccccg aggaggccgc ccactgcatc 1380
cacgccgagt gggacaccgg cctgaacagc aagttcacct tcagcatccc ctacatcagc 1440
gccgccgact acgcctacac cgccagccac aaggccgaga ccacctgcgt gcagggctgg 1500
gtgtgcgtgt accagatcac ccacggcaag gccgacgccg acgccctggt ggtgagcgcc 1560
agcgccggca aggacttcga gctgcgcctg cccgtggacg cccgcaagca gaccaccacc 1620
accggcgaga gcgccgaccc cgtgaccacc accgtggaga actacggcgg cgagacccag 1680
gtgcagcgcc gccaccacac cgacgtggcc ttcgtgctgg accgcttcgt ggaggtgacc 1740
gtgagcggcc gcaaccagca caccctggac gtgatgcagg cccacaagga caacatcgtg 1800
ggcgccctgc tgcgcgccgc cacctactac ttcagcgacc tggagatcgc cgtgacccac 1860
accggcaagc tgacctgggt gcccaacggc gcccccgtga gcgccctgaa caacaccacc 1920
aaccccaccg cctaccacaa gggccccgtg acccgcctgg ccctgcccta caccgccccc 1980
caccgcgtgc tggccaccgc ctacaccggc accaccacct acaccgccag cgcccgcggc 2040
gacctggccc acctgaccac cacccacgcc cgccacctgc ccaccagctt caacttcggc 2100

```
gccgtgaagg ccgagaccat caccgagctg ctggtgcgca tgaagcgcgc cgagctgtac    2160
tgcgtgaaga agcccgtggc cctgaaggtg aaggccaaga acaccctgat cgtgaccgag    2220
agcggcgccc ccccaccga cctgcagaag atggtgatgg caacaccaa gcccgtggag      2280 ctgatcctgg acggcaagac cgtggccatc tgctgcgcca ccggcgtgtt cggcaccgcc    2340
tacctggtgc ccgccacct gttcgccgag aagtacgaca agatcatgct ggacggccgc    2400
gccatgaccg acagcgacta ccgcgtgttc gagttcgaga tcaaggtgaa gggccaggac    2460
atgctgagcg acgccgccct gatggtgctg caccgcggca accgcgtgcg cgacatcacc    2520
aagcacttcc gcgacaccgc ccgcatgaag aagggcaccc ccgtggtggg cgtgatcaac    2580
aacgccgacg tgggccgcct gatcttcagc ggcgaggccc tgacctacaa ggacatcgtg    2640
gtgtgcatgg acggcgacac catgcccggc ctgttcgcct acaaggccgc caccaaggcc    2700
ggctactgcg gcggcgccgt gctggccaag gacgcgccg acaccttcat cgtgggcacc    2760
cacagcgccg gcggcgcaa cggcgtgggc tactgcagct gcgtgagccg cagcatgctg    2820
ctgaagatga aggcccacat cgaccccgag cccccaccacg agggcctgat cgtggacacc    2880
cgcgacgtgg aggagcgcgt gcacgtgatg tga                                2913
```

<210> SEQ ID NO 6
<211> LENGTH: 970
<212> TYPE: PRT
<213> ORGANISM: Artificial Sequence
<220> FEATURE:
<223> OTHER INFORMATION: Consensus VP1-VP4 subtype C and consensus C3

<400> SEQUENCE: 6

```
Met Leu Asn Glu Gly Trp Lys Ala Ser Val Gln Arg Lys Leu Lys Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Thr Asn Thr Gln Asn Asn
65                  70                  75                  80

Asp Trp Phe Ser Lys Leu Ala Ser Ala Phe Ser Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg Asn Gly His Thr Thr Ser Thr Thr Gln Ser
        115                 120                 125

Ser Val Gly Val Thr Phe Gly Tyr Ala Thr Ala Glu Asp Ser Thr Ser
    130                 135                 140

Gly Pro Asn Thr Ser Gly Leu Glu Thr Arg Val His Gln Ala Glu Arg
145                 150                 155                 160

Phe Phe Lys Met Ala Leu Phe Asp Trp Val Pro Ser Gln Asn Phe Gly
                165                 170                 175

His Met His Lys Val Val Leu Pro His Glu Pro Lys Gly Val Tyr Gly
            180                 185                 190

Gly Leu Val Lys Ser Tyr Ala Tyr Met Arg Asn Gly Trp Asp Val Glu
        195                 200                 205

Val Thr Ala Val Gly Asn Gln Phe Asn Gly Gly Cys Leu Leu Val Ala
    210                 215                 220
```

```
Leu Val Pro Glu Met Gly Asp Ile Ser Asp Arg Glu Lys Tyr Gln Leu
225                 230                 235                 240

Thr Leu Tyr Pro His Gln Phe Ile Asn Pro Arg Thr Asn Met Thr Ala
            245                 250                 255

His Ile Thr Val Pro Tyr Val Gly Val Asn Arg Tyr Asp Gln Tyr Lys
                260                 265                 270

Gln His Arg Pro Trp Thr Leu Val Val Met Val Val Ala Pro Leu Thr
            275                 280                 285

Thr Asn Thr Ala Gly Ala Gln Gln Ile Lys Val Tyr Ala Asn Ile Ala
        290                 295                 300

Pro Thr Asn Val His Val Ala Gly Glu Leu Pro Ser Lys Glu Gly Ile
305                 310                 315                 320

Phe Pro Val Ala Cys Ser Asp Gly Tyr Gly Asn Met Val Thr Thr Asp
                325                 330                 335

Pro Lys Thr Ala Asp Pro Val Tyr Gly Lys Val Tyr Asn Pro Pro Arg
            340                 345                 350

Thr Ala Leu Pro Gly Arg Phe Thr Asn Tyr Leu Asp Val Ala Glu Ala
        355                 360                 365

Cys Pro Thr Phe Leu Met Phe Glu Asn Val Pro Tyr Val Ser Thr Arg
370                 375                 380

Thr Asp Gly Gln Arg Leu Leu Ala Lys Phe Asp Val Ser Leu Ala Ala
385                 390                 395                 400

Lys His Met Ser Asn Thr Tyr Leu Ala Gly Leu Ala Gln Tyr Tyr Thr
                405                 410                 415

Gln Tyr Thr Gly Thr Ile Asn Leu His Phe Met Phe Thr Gly Pro Thr
            420                 425                 430

Asp Ala Lys Ala Arg Tyr Met Val Ala Tyr Val Pro Pro Gly Met Asp
        435                 440                 445

Ala Pro Asp Asn Pro Glu Glu Ala Ala His Cys Ile His Ala Glu Trp
450                 455                 460

Asp Thr Gly Leu Asn Ser Lys Phe Thr Phe Ser Ile Pro Tyr Ile Ser
465                 470                 475                 480

Ala Ala Asp Tyr Ala Tyr Thr Ala Ser His Lys Ala Glu Thr Thr Cys
                485                 490                 495

Val Gln Gly Trp Val Cys Val Tyr Gln Ile Thr His Gly Lys Ala Asp
            500                 505                 510

Ala Asp Ala Leu Val Val Ser Ala Ser Ala Gly Lys Asp Phe Glu Leu
        515                 520                 525

Arg Leu Pro Val Asp Ala Arg Lys Gln Thr Thr Thr Thr Gly Glu Ser
530                 535                 540

Ala Asp Pro Val Thr Thr Thr Val Glu Asn Tyr Gly Gly Glu Thr Gln
545                 550                 555                 560

Val Gln Arg Arg His His Thr Asp Val Ala Phe Val Leu Asp Arg Phe
            565                 570                 575

Val Glu Val Thr Val Ser Gly Arg Asn Gln His Thr Leu Asp Val Met
            580                 585                 590

Gln Ala His Lys Asp Asn Ile Val Gly Ala Leu Leu Arg Ala Ala Thr
        595                 600                 605

Tyr Tyr Phe Ser Asp Leu Glu Ile Ala Val Thr His Thr Gly Lys Leu
        610                 615                 620

Thr Trp Val Pro Asn Gly Ala Pro Val Ser Ala Leu Asn Asn Thr Thr
625                 630                 635                 640
```

```
Asn Pro Thr Ala Tyr His Lys Gly Pro Val Thr Arg Leu Ala Leu Pro
                645                 650                 655

Tyr Thr Ala Pro His Arg Val Leu Ala Thr Ala Tyr Thr Gly Thr Thr
            660                 665                 670

Thr Tyr Thr Ala Ser Ala Arg Gly Asp Leu Ala His Leu Thr Thr Thr
        675                 680                 685

His Ala Arg His Leu Pro Thr Ser Phe Asn Phe Gly Ala Val Lys Ala
    690                 695                 700

Glu Thr Ile Thr Glu Leu Leu Val Arg Met Lys Arg Ala Glu Leu Tyr
705                 710                 715                 720

Cys Val Lys Lys Pro Val Ala Leu Lys Val Lys Ala Lys Asn Thr Leu
                725                 730                 735

Ile Val Thr Glu Ser Gly Ala Pro Pro Thr Asp Leu Gln Lys Met Val
            740                 745                 750

Met Gly Asn Thr Lys Pro Val Glu Leu Ile Leu Asp Gly Lys Thr Val
        755                 760                 765

Ala Ile Cys Cys Ala Thr Gly Val Phe Gly Thr Ala Tyr Leu Val Pro
    770                 775                 780

Arg His Leu Phe Ala Glu Lys Tyr Asp Lys Ile Met Leu Asp Gly Arg
785                 790                 795                 800

Ala Met Thr Asp Ser Asp Tyr Arg Val Phe Glu Phe Glu Ile Lys Val
                805                 810                 815

Lys Gly Gln Asp Met Leu Ser Asp Ala Ala Leu Met Val Leu His Arg
            820                 825                 830

Gly Asn Arg Val Arg Asp Ile Thr Lys His Phe Arg Asp Thr Ala Arg
        835                 840                 845

Met Lys Lys Gly Thr Pro Val Val Gly Val Ile Asn Asn Ala Asp Val
    850                 855                 860

Gly Arg Leu Ile Phe Ser Gly Glu Ala Leu Thr Tyr Lys Asp Ile Val
865                 870                 875                 880

Val Cys Met Asp Gly Asp Thr Met Pro Gly Leu Phe Ala Tyr Lys Ala
                885                 890                 895

Ala Thr Lys Ala Gly Tyr Cys Gly Gly Ala Val Leu Ala Lys Asp Gly
            900                 905                 910

Ala Asp Thr Phe Ile Val Gly Thr His Ser Ala Gly Gly Arg Asn Gly
        915                 920                 925

Val Gly Tyr Cys Ser Cys Val Ser Arg Ser Met Leu Leu Lys Met Lys
    930                 935                 940

Ala His Ile Asp Pro Glu Pro His His Glu Gly Leu Ile Val Asp Thr
945                 950                 955                 960

Arg Asp Val Glu Glu Arg Val His Val Met
                965                 970
```

<210> SEQ ID NO 7
<211> LENGTH: 2925
<212> TYPE: DNA
<213> ORGANISM: Artificial Sequence
<220> FEATURE:
<223> OTHER INFORMATION: plasmid 4 consensus VP1-VP4 subtype O and consensus C3

<400> SEQUENCE: 7

```
atgctgaacg gcgagtggaa ggccaaggtg cagaagcgcc tgcgcggcgc cggccagagc      60
agccccgcca ccggcagcca gaaccagagc ggcaacaccg gcagcatcat caacaactac     120
tacatgcagc agtaccagaa cagcatggac acccagctgg gcgacaacgc catcagcggc     180
```

```
ggcagcaacg agggcagcac cgacaccacc agcacccaca ccaccaacac ccagaacaac    240
gactggttca gcaagctggc cagcagcgcc ttcagcggcc tgttcggcgc cctgctggcc    300
gacaagaaga ccgaggagac caccctgctg gaggaccgca tcctgaccac ccgcaacggc    360
cacaccacca gcaccaccca gagcagcgtg ggcgtgacct acggctacgc caccgccgag    420
gacttcgtga gcggccccaa caccagcggc ctggagaccc gcgtggtgca ggccgagcgc    480
ttcttcaaga cccacctgtt cgactgggtg accagcgacc ccttcggccg ctgctacctg    540
ctggagctgc ccaccgacca agggcgtg tacggcagcc tgaccgacag ctacgcctac     600
atgcgcaacg ctgggacgt ggaggtgacc gccgtgggca accagttcaa cggcggctgc     660
ctgctggtgg ccatggtgcc cgagctgtgc agcatcgaca agcgcgagct gtaccagctg    720
accctgttcc cccaccagtt catcaacccc cgcaccaaca tgaccgccca catcaccgtg    780
cccttcgtgg gcgtgaaccg ctacgaccag tacaaggtgc acaagccctg gaccctggtg    840
gtgatggtgg tggcccccct gaccgtgaac accgagggcg ccccccagat caaggtgtac    900
gccaacatcg cccccaccaa cgtgcacgtg gccggcgagt tccccagcaa ggagggcatc    960
ttccccgtgg cctgcagcga cggctacggc ggcctggtga ccaccgaccc caagaccgcc    1020
gaccccgcct acggcaaggt gttcaacccc cccgcaaca tgctgcccgg ccgcttcacc     1080
aacttcctgg acgtggccga ggcctgcccc accttcctgc acttcgaggg cggcgtgccc    1140
tacgtgacca ccaagaccga cagcgaccgc gtgctggccc agttcgacct gagcctggcc    1200
gccaagcaca tgagcaacac cttcctggcc ggcctggccc agtactacac ccagtacagc    1260
ggcaccatca acctgcactt catgttcacc ggccccaccg acgccaaggc ccgctacatg    1320
atcgcctacg ccccccccgg catggagccc cccaagaccc ccgaggccgc cgcccactgc    1380
atccacgccg agtgggacac cggcctgaac agcaagttca ccttcagcat cccctacctg    1440
agcgccgccg actacgccta caccgccagc gacgccgccg agaccaccaa cgtgcagggc    1500
tgggtgtgcc tgttccagat cacccacggc aaggccgacg cgacgccct ggtggtgctg     1560
gccagcgccg gcaaggactt cgagctgcgc ctgcccgtgg acgcccgcac ccagaccacc    1620
agcgccggcg agagcgccga ccccgtgacc gccaccgtgg agaactacgg cggcgagacc    1680
caggtgcagc gccgccagca caccgacgtg agcttcatcc tggaccgctt cgtgaaggtg    1740
accccccaagg accagatcaa cgtgctggac ctgatgcaga cccccgccca cccctggtg    1800
ggcgccctgc tgcgcaccgc cacctactac ttcgccgacc tggaggtggc cgtgaagcac    1860
gagggcaacc tgacctgggt gcccaacggc gcccccgaga ccgccctgga caacaccacc    1920
aaccccaccg cctaccacaa ggccccccctg acccgcctgg ccctgcccta caccgccccc    1980
caccgcgtgc tggccaccgt gtacaacggc aactgcaagt acggcgagag ccccgtgacc    2040
aacgtgcgcg cgacctgca ggtgctggcc cagaaggccg cccgcaccct gcccaccagc     2100
ttcaactacg cgccatcaa ggccaccgc gtgaccgagc tgctgtaccg catgaagcgc      2160
gccgagacct actgcgtgaa gagcccgtg gccctgaagg tgaaggccaa gaacaccctg     2220
atcgtgaccg agagcggcgc ccccccacc gacctgcaga gatggtgat gggcaacacc      2280
aagcccgtgg agctgatcct ggacggcaag accgtggcca tctgctgcgc caccggcgtg    2340
ttcggcaccg cctacctggt gccccgccac ctgttcgccg agaagtacga caagatcatg    2400
ctggacggcc gcgccatgac cgacagcgac taccgcgtgt cgagttcga gatcaaggtg     2460
aagggccagg acatgctgag cgacgccgcc ctgatggtgc tgcaccgcgg caaccgcgtg    2520
```

-continued

```
cgcgacatca ccaagcactt ccgcgacacc gcccgcatga agaagggcac ccccgtggtg   2580
ggcgtgatca acaacgccga cgtgggccgc ctgatcttca gcggcgaggc cctgacctac   2640
aaggacatcg tggtgtgcat ggacggcgac accatgcccg gcctgttcgc ctacaaggcc   2700
gccaccaagg ccggctactg cggcggcgcc gtgctggcca aggacggcgc cgacaccttc   2760
atcgtgggca cccacagcgc cggcggccgc aacggcgtgg gctactgcag ctgcgtgagc   2820
cgcagcatgc tgctgaagat gaaggcccac atcgaccccg agccccacca cgagggcctg   2880
atcgtggaca cccgcgacgt ggaggagcgc gtgcacgtga tgtga                   2925

<210> SEQ ID NO 8
<211> LENGTH: 974
<212> TYPE: PRT
<213> ORGANISM: Artificial Sequence
<220> FEATURE:
<223> OTHER INFORMATION: consensus VP1-VP4 subtype O and consensus C3

<400> SEQUENCE: 8

Met Leu Asn Gly Glu Trp Lys Ala Lys Val Gln Lys Arg Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Thr Asn Thr Gln Asn Asn
65                  70                  75                  80

Asp Trp Phe Ser Lys Leu Ala Ser Ser Ala Phe Ser Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg Asn Gly His Thr Thr Ser Thr Thr Gln Ser
        115                 120                 125

Ser Val Gly Val Thr Tyr Gly Tyr Ala Thr Ala Glu Asp Phe Val Ser
    130                 135                 140

Gly Pro Asn Thr Ser Gly Leu Glu Thr Arg Val Val Gln Ala Glu Arg
145                 150                 155                 160

Phe Phe Lys Thr His Leu Phe Asp Trp Val Thr Ser Asp Pro Phe Gly
                165                 170                 175

Arg Cys Tyr Leu Leu Glu Leu Pro Thr Asp His Lys Gly Val Tyr Gly
            180                 185                 190

Ser Leu Thr Asp Ser Tyr Ala Tyr Met Arg Asn Gly Trp Asp Val Glu
        195                 200                 205

Val Thr Ala Val Gly Asn Gln Phe Asn Gly Gly Cys Leu Leu Val Ala
    210                 215                 220

Met Val Pro Glu Leu Cys Ser Ile Asp Lys Arg Glu Leu Tyr Gln Leu
225                 230                 235                 240

Thr Leu Phe Pro His Gln Phe Ile Asn Pro Arg Thr Asn Met Thr Ala
                245                 250                 255

His Ile Thr Val Pro Phe Val Gly Val Asn Arg Tyr Asp Gln Tyr Lys
            260                 265                 270

Val His Lys Pro Trp Thr Leu Val Val Met Val Val Ala Pro Leu Thr
        275                 280                 285

Val Asn Thr Glu Gly Ala Pro Gln Ile Lys Val Tyr Ala Asn Ile Ala
```

```
                290                 295                 300
Pro Thr Asn Val His Val Ala Gly Glu Phe Pro Ser Lys Glu Gly Ile
305                 310                 315                 320

Phe Pro Val Ala Cys Ser Asp Gly Tyr Gly Leu Val Thr Thr Asp
                325                 330                 335

Pro Lys Thr Ala Asp Pro Ala Tyr Gly Lys Val Phe Asn Pro Arg
                340                 345                 350

Asn Met Leu Pro Gly Arg Phe Thr Asn Phe Leu Asp Val Ala Glu Ala
                355                 360                 365

Cys Pro Thr Phe Leu His Phe Glu Gly Gly Val Pro Tyr Val Thr Thr
370                 375                 380

Lys Thr Asp Ser Asp Arg Val Leu Ala Gln Phe Asp Leu Ser Leu Ala
385                 390                 395                 400

Ala Lys His Met Ser Asn Thr Phe Leu Ala Gly Leu Ala Gln Tyr Tyr
                405                 410                 415

Thr Gln Tyr Ser Gly Thr Ile Asn Leu His Phe Met Phe Thr Gly Pro
                420                 425                 430

Thr Asp Ala Lys Ala Arg Tyr Met Ile Ala Tyr Ala Pro Pro Gly Met
                435                 440                 445

Glu Pro Pro Lys Thr Pro Glu Ala Ala Ala His Cys Ile His Ala Glu
450                 455                 460

Trp Asp Thr Gly Leu Asn Ser Lys Phe Thr Phe Ser Ile Pro Tyr Leu
465                 470                 475                 480

Ser Ala Ala Asp Tyr Ala Tyr Thr Ala Ser Asp Ala Ala Glu Thr Thr
                485                 490                 495

Asn Val Gln Gly Trp Val Cys Leu Phe Gln Ile Thr His Gly Lys Ala
                500                 505                 510

Asp Gly Asp Ala Leu Val Val Leu Ala Ser Ala Gly Lys Asp Phe Glu
                515                 520                 525

Leu Arg Leu Pro Val Asp Ala Arg Thr Gln Thr Thr Ser Ala Gly Glu
530                 535                 540

Ser Ala Asp Pro Val Thr Ala Thr Val Glu Asn Tyr Gly Gly Glu Thr
545                 550                 555                 560

Gln Val Gln Arg Arg Gln His Thr Asp Val Ser Phe Ile Leu Asp Arg
                565                 570                 575

Phe Val Lys Val Thr Pro Lys Asp Gln Ile Asn Val Leu Asp Leu Met
                580                 585                 590

Gln Thr Pro Ala His Thr Leu Val Gly Ala Leu Leu Arg Thr Ala Thr
                595                 600                 605

Tyr Tyr Phe Ala Asp Leu Glu Val Ala Val Lys His Glu Gly Asn Leu
                610                 615                 620

Thr Trp Val Pro Asn Gly Ala Pro Glu Thr Ala Leu Asp Asn Thr Thr
625                 630                 635                 640

Asn Pro Thr Ala Tyr His Lys Ala Pro Leu Thr Arg Leu Ala Leu Pro
                645                 650                 655

Tyr Thr Ala Pro His Arg Val Leu Ala Thr Val Tyr Asn Gly Asn Cys
                660                 665                 670

Lys Tyr Gly Glu Ser Pro Val Asn Val Arg Gly Asp Leu Gln Val
                675                 680                 685

Leu Ala Gln Lys Ala Ala Arg Thr Leu Pro Thr Ser Phe Asn Tyr Gly
                690                 695                 700

Ala Ile Lys Ala Thr Arg Val Thr Glu Leu Leu Tyr Arg Met Lys Arg
705                 710                 715                 720
```

Ala Glu Thr Tyr Cys Val Lys Pro Val Ala Leu Val Lys Ala
                725                 730                 735

Lys Asn Thr Leu Ile Val Thr Glu Ser Gly Ala Pro Thr Asp Leu
        740                 745                 750

Gln Lys Met Val Met Gly Asn Thr Lys Pro Val Glu Leu Ile Leu Asp
            755                 760                 765

Gly Lys Thr Val Ala Ile Cys Cys Ala Thr Gly Val Phe Gly Thr Ala
        770                 775                 780

Tyr Leu Val Pro Arg His Leu Phe Ala Glu Lys Tyr Asp Lys Ile Met
785                 790                 795                 800

Leu Asp Gly Arg Ala Met Thr Asp Ser Asp Tyr Arg Val Phe Glu Phe
                805                 810                 815

Glu Ile Lys Val Lys Gly Gln Asp Met Leu Ser Asp Ala Ala Leu Met
                820                 825                 830

Val Leu His Arg Gly Asn Arg Val Arg Asp Ile Thr Lys His Phe Arg
                835                 840                 845

Asp Thr Ala Arg Met Lys Lys Gly Thr Pro Val Val Gly Val Ile Asn
        850                 855                 860

Asn Ala Asp Val Gly Arg Leu Ile Phe Ser Gly Glu Ala Leu Thr Tyr
865                 870                 875                 880

Lys Asp Ile Val Val Cys Met Asp Gly Asp Thr Met Pro Gly Leu Phe
                885                 890                 895

Ala Tyr Lys Ala Ala Thr Lys Ala Gly Tyr Cys Gly Gly Ala Val Leu
                900                 905                 910

Ala Lys Asp Gly Ala Asp Thr Phe Ile Val Gly Thr His Ser Ala Gly
                915                 920                 925

Gly Arg Asn Gly Val Gly Tyr Cys Ser Cys Val Ser Arg Ser Met Leu
        930                 935                 940

Leu Lys Met Lys Ala His Ile Asp Pro Glu Pro His His Glu Gly Leu
945                 950                 955                 960

Ile Val Asp Thr Arg Asp Val Glu Glu Arg Val His Val Met
                965                 970

<210> SEQ ID NO 9
<211> LENGTH: 2952
<212> TYPE: DNA
<213> ORGANISM: Artificial Sequence
<220> FEATURE:
<223> OTHER INFORMATION: nucleic acid, consensus VP1-VP4 subtype SAT1
       and consensus C3

<400> SEQUENCE: 9
atgctggacg tggactggca ggaccgcgcc ggcctgttcc tgcgcggcgc cggccagagc    60
agccccgcca ccggcagcca gaaccagagc ggcaacaccg gcagcatcat caacaactac   120
tacatgcagc agtaccagaa cagcatggac acccagctgg cgacaacgc catcagcggc   180 ggcagcaacg agggcagcac cgacaccacc agcacccaca ccaacaacac ccagaacaac   240
gactggttca gcaagctggc ccagagcgcc ttcagcggcc tggtgggcgc cctgctggcc   300
gacaagaaga ccgaggagac caccctgctg gaggaccgca tcatgaccac cagccacggc   360
accaccacca gcaccaccca gagcagcgtg ggcgtgacct acggctacgc cctggccgac   420
aagttcctgc ccggccccaa caccaacggc ctggagaccc gcgtggagca ggccgagcgc   480
ttcttcaagc acaagctgtt cgactggacc accgaccaga gttcggcac acccacgtg   540 ctggagctgc ccaccgacca aagggcatc tacggccagc tggtggacag ccacgcctac   600

```
atccgcaacg gctgggacgt gcaggtgagc gccaccgcca cccagttcaa cggcggctgc    660
ctgctggtgg ccatggtgcc cgagctgtgc aagctggacg accgcgagaa gtaccagctg    720
accctgttcc cccaccagtt cctgaacccc cgcaccaaca ccaccgccca catccaggtg    780
ccctacctgg gcgtggaccg ccacgaccag ggcacccgcc acaaggcctg gaccctggtg    840
gtgatggtgg tggcccccta caccaacgac cagaccatcg gcagcaccaa ggccgaggtg    900
tacgtgaaca tcgcccccac caacgtgtac gtggccggcg agaagcccgc caagcagggc    960
atcctgcccg tggccgtgag cgacggctac ggcggcttcc agaacaccga ccccaagacc   1020
agcgacccca tctacggcca cgtgtacaac cccgcccgca ccctgtaccc cggccgcttc   1080
accaacctgc tggacgtggc cgaggcctgc cccaccctgc tggacttcaa cggcgtgccc   1140
tacgtgcaga cccagaacaa cagcggcagc aaggtgctgg cccgcttcga cctggccttc   1200
ggccacaaga acatgaagaa cacctacatg agcggcctgg cccagtactt cgcccagtac   1260
agcggcaccc tgaacctgca cttcatgtac accggcccca ccaacaacaa ggccaagtac   1320
atggtggcct acatcccccc cggcacccac cccctgcccg agacccccga tggccagc     1380 cactgctacc acgccgagtg ggacaccggc ctgaacagca ccttcacctt caccgtgccc   1440
tacatcagcg ccgccgacta cgcctacacc tacgccgacg agcccgagca ggccagcgtg   1500
cagggctggg tgggcgtgta ccagatcacc gacacccacg agaaggacgg cgccgtgatc   1560
gtgaccgtga gcgccggccc cgacttcgag ttccgcatgc ccatcagccc cagccgccag   1620
accaccagcg ccggcgaggg cgccgacccc gtgaccaccg acgtgagcga gcacggcggc   1680
gacagccgca ccgcccgccg cgcccacacc gacgtggcct tcctgctgga ccgcttcacc   1740
ctggtgggca agacccagga caacaagctg gtgctggacc tgctgaccac caaggagaag   1800
agcctggtgg gcgccctgct gcgcgccgcc acctactact tcagcgacct ggaggtggcc   1860
tgcgtgggca ccaacaagtg ggtgggctgg accccaacg gcagcccgt gaagctgagc    1920 gaggtgggcg acaaccccgt ggtgttcagc cacaacggca ccacccgctt cgccctgccc   1980
tacaccgccc ccaccgcgt gctggccacc gtgtacaacg gcgactgcaa gtacaagccc   2040
accggcaccc ccccccgcga aacatccgc ggcgacctgg ccaccctggc cgcccgcatc   2100
gccagcgaga cccacatccc caccaccttc aactacggca tgatctacac cgaggccgag   2160
gtggacgtgt acctgcgcat gaagcgcgcc gagctgtact gcgtgaagaa gcccgtggcc   2220
ctgaaggtga aggccaagaa caccctgatc gtgaccgaga gcggcgcccc ccccaccgac   2280
ctgcagaaga tggtgatggg caacaccaag cccgtggagc tgatcctgga cggcaagacc   2340
gtggccatct gctgcgccac cggcgtgttc ggcaccgcct acctggtgcc ccgccacctg   2400
ttcgccgaga gtacgacaa gatcatgctg acggccgcg ccatgaccga cagcgactac   2460
cgcgtgttcg agttcgagat caaggtgaag ggccaggaca tgctgagcga cgccgccctg   2520
atggtgctgc accgcggcaa ccgcgtgcgc gacatcacca gcacttccg cgacaccgcc   2580 cgcatgaaga agggcacccc cgtggtgggc gtgatcaaca cgccgacgt gggccgcctg   2640 atcttcagcg gcgaggccct gacctacaag gacatcgtgg tgtgcatgga cggcgacacc   2700
atgcccggcc tgttcgccta caaggccgcc accaaggccg gctactgcgg cggcgccgtg   2760
ctggccaagg acggcgccga caccttcatc gtgggcaccc acagcgccgg cggccgcaac   2820
ggcgtgggct actgcagctg cgtgagccgc agcatgctgc tgaagatgaa ggcccacatc   2880
gaccccgagc cccaccacga gggcctgatc gtggacaccc gcgacgtgga ggagcgcgtg   2940
```
cacgtgatgt ga                                                      2952

<210> SEQ ID NO 10
<211> LENGTH: 983
<212> TYPE: PRT
<213> ORGANISM: Artificial Sequence
<220> FEATURE:
<223> OTHER INFORMATION: conconsensus VP1-VP4 subtypeSAT1 and consensus
     C3

<400> SEQUENCE: 10

Met Leu Asp Val Asp Trp Gln Asp Arg Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Asn Asn Thr Gln Asn Asn
65                  70                  75                  80

Asp Trp Phe Ser Lys Leu Ala Gln Ser Ala Phe Ser Gly Leu Val Gly
                85                  90                  95

Ala Leu Leu Ala Asp Lys Lys Thr Glu Glu Thr Thr Leu Leu Glu Asp
            100                 105                 110

Arg Ile Met Thr Thr Ser His Gly Thr Thr Thr Ser Thr Thr Gln Ser
        115                 120                 125

Ser Val Gly Val Thr Tyr Gly Tyr Ala Leu Ala Asp Lys Phe Leu Pro
    130                 135                 140

Gly Pro Asn Thr Asn Gly Leu Glu Thr Arg Val Glu Gln Ala Glu Arg
145                 150                 155                 160

Phe Phe Lys His Lys Leu Phe Asp Trp Thr Thr Asp Gln Gln Phe Gly
                165                 170                 175

Thr Thr His Val Leu Glu Leu Pro Thr Asp His Lys Gly Ile Tyr Gly
            180                 185                 190

Gln Leu Val Asp Ser His Ala Tyr Ile Arg Asn Gly Trp Asp Val Gln
        195                 200                 205

Val Ser Ala Thr Ala Thr Gln Phe Asn Gly Gly Cys Leu Leu Val Ala
    210                 215                 220

Met Val Pro Glu Leu Cys Lys Leu Asp Asp Arg Glu Lys Tyr Gln Leu
225                 230                 235                 240

Thr Leu Phe Pro His Gln Phe Leu Asn Pro Arg Thr Asn Thr Thr Ala
                245                 250                 255

His Ile Gln Val Pro Tyr Leu Gly Val Asp Arg His Asp Gln Gly Thr
            260                 265                 270

Arg His Lys Ala Trp Thr Leu Val Val Met Val Val Ala Pro Tyr Thr
        275                 280                 285

Asn Asp Gln Thr Ile Gly Ser Thr Lys Ala Glu Val Tyr Val Asn Ile
    290                 295                 300

Ala Pro Thr Asn Val Tyr Val Ala Gly Glu Lys Pro Ala Lys Gln Gly
305                 310                 315                 320

Ile Leu Pro Val Ala Val Ser Asp Gly Tyr Gly Gly Phe Gln Asn Thr
                325                 330                 335

Asp Pro Lys Thr Ser Asp Pro Ile Tyr Gly His Val Tyr Asn Pro Ala
            340                 345                 350

```
Arg Thr Leu Tyr Pro Gly Arg Phe Thr Asn Leu Leu Asp Val Ala Glu
            355                 360                 365

Ala Cys Pro Thr Leu Leu Asp Phe Asn Gly Val Pro Tyr Val Gln Thr
        370                 375                 380

Gln Asn Asn Ser Gly Ser Lys Val Leu Ala Arg Phe Asp Leu Ala Phe
385                 390                 395                 400

Gly His Lys Asn Met Lys Asn Thr Tyr Met Ser Gly Leu Ala Gln Tyr
                405                 410                 415

Phe Ala Gln Tyr Ser Gly Thr Leu Asn Leu His Phe Met Tyr Thr Gly
            420                 425                 430

Pro Thr Asn Asn Lys Ala Lys Tyr Met Val Ala Tyr Ile Pro Pro Gly
            435                 440                 445

Thr His Pro Leu Pro Glu Thr Pro Glu Met Ala Ser His Cys Tyr His
        450                 455                 460

Ala Glu Trp Asp Thr Gly Leu Asn Ser Thr Phe Thr Phe Thr Val Pro
465                 470                 475                 480

Tyr Ile Ser Ala Ala Asp Tyr Ala Tyr Thr Tyr Ala Asp Glu Pro Glu
                485                 490                 495

Gln Ala Ser Val Gln Gly Trp Val Gly Val Tyr Gln Ile Thr Asp Thr
        500                 505                 510

His Glu Lys Asp Gly Ala Val Ile Val Thr Val Ser Ala Gly Pro Asp
        515                 520                 525

Phe Glu Phe Arg Met Pro Ile Ser Pro Ser Arg Gln Thr Thr Ser Ala
        530                 535                 540

Gly Glu Gly Ala Asp Pro Val Thr Thr Asp Val Ser Glu His Gly Gly
545                 550                 555                 560

Asp Ser Arg Thr Ala Arg Arg Ala His Thr Asp Val Ala Phe Leu Leu
                565                 570                 575

Asp Arg Phe Thr Leu Val Gly Lys Thr Gln Asp Asn Lys Leu Val Leu
            580                 585                 590

Asp Leu Leu Thr Thr Lys Glu Lys Ser Leu Val Gly Ala Leu Leu Arg
            595                 600                 605

Ala Ala Thr Tyr Tyr Phe Ser Asp Leu Glu Val Ala Cys Val Gly Thr
        610                 615                 620

Asn Lys Trp Val Gly Trp Thr Pro Asn Gly Ser Pro Val Lys Leu Ser
625                 630                 635                 640

Glu Val Gly Asp Asn Pro Val Val Phe Ser His Asn Gly Thr Thr Arg
                645                 650                 655

Phe Ala Leu Pro Tyr Thr Ala Pro His Arg Val Leu Ala Thr Val Tyr
            660                 665                 670

Asn Gly Asp Cys Lys Tyr Lys Pro Thr Gly Thr Pro Arg Glu Asn
            675                 680                 685

Ile Arg Gly Asp Leu Ala Thr Leu Ala Ala Arg Ile Ala Ser Glu Thr
        690                 695                 700

His Ile Pro Thr Thr Phe Asn Tyr Gly Met Ile Tyr Thr Glu Ala Glu
705                 710                 715                 720

Val Asp Val Tyr Leu Arg Met Lys Arg Ala Glu Leu Tyr Cys Val Lys
                725                 730                 735

Lys Pro Val Ala Leu Lys Val Lys Ala Lys Asn Thr Leu Ile Val Thr
            740                 745                 750

Glu Ser Gly Ala Pro Pro Thr Asp Leu Gln Lys Met Val Met Gly Asn
        755                 760                 765

Thr Lys Pro Val Glu Leu Ile Leu Asp Gly Lys Thr Val Ala Ile Cys
```

```
                770               775              780
Cys Ala Thr Gly Val Phe Gly Thr Ala Tyr Leu Val Pro Arg His Leu
785                 790              795                 800

Phe Ala Glu Lys Tyr Asp Lys Ile Met Leu Asp Gly Arg Ala Met Thr
                805                 810                 815

Asp Ser Asp Tyr Arg Val Phe Glu Phe Glu Ile Lys Val Lys Gly Gln
                820                 825                 830

Asp Met Leu Ser Asp Ala Ala Leu Met Val Leu His Arg Gly Asn Arg
                835                 840                 845

Val Arg Asp Ile Thr Lys His Phe Arg Asp Thr Ala Arg Met Lys Lys
850                 855                 860

Gly Thr Pro Val Val Gly Val Ile Asn Asn Ala Asp Val Gly Arg Leu
865                 870                 875                 880

Ile Phe Ser Gly Glu Ala Leu Thr Tyr Lys Asp Ile Val Val Cys Met
                885                 890                 895

Asp Gly Asp Thr Met Pro Gly Leu Phe Ala Tyr Lys Ala Ala Thr Lys
                900                 905                 910

Ala Gly Tyr Cys Gly Gly Ala Val Leu Ala Lys Asp Gly Ala Asp Thr
                915                 920                 925

Phe Ile Val Gly Thr His Ser Ala Gly Gly Arg Asn Gly Val Gly Tyr
930                 935                 940

Cys Ser Cys Val Ser Arg Ser Met Leu Leu Lys Met Lys Ala His Ile
945                 950                 955                 960

Asp Pro Glu Pro His His Glu Gly Leu Ile Val Asp Thr Arg Asp Val
                965                 970                 975

Glu Glu Arg Val His Val Met
                980

<210> SEQ ID NO 11
<211> LENGTH: 2940
<212> TYPE: DNA
<213> ORGANISM: Artificial Sequence
<220> FEATURE:
<223> OTHER INFORMATION: nucleic acid, consensus VP1-VP4 subtype SAT2
      and consensus C3

<400> SEQUENCE: 11
atgctggacg tggactggca ggacaaggcc ggcctgttcc tgcgcggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc     180 ggcagcaacg agggcagcac cgacaccacc agcacccaca ccaacaacac ccagaacaac     240
gactggttca gcaagctggc ccagagcgcc atcagcggcc tgttcggcgc cctgctggcc     300
gacaagaaga ccgaggagac caccctgctg gaggaccgca tcctgaccac ccgccacggc     360
accaccacca gcaccaccca gagcagcgtg ggcatcacct acggctacgc cgacgccgac     420
agcttccgcc ccgccccaa caccagcggc ctggagaccc gcgtggagca ggccgagcgc     480
ttcttcaagg agaagctgtt cgactggacc agcgacaagc ccttcggcac cctgtacgtg     540
ctggagctgc caaggacca agggcatc tacggcagcc tgaccgacgc ctacacctac     600
atgcgcaacg gctgggacgt gcaggtgagc gccaccagca cccagttcaa cggcggcagc     660
ctgctggtgg ccatggtgcc cgagctgtgc agcctgaagg accgcgagga gttccagctg     720
accctgtacc ccaccagtt catcaacccc cgcaccaaca ccaccgccca catccaggtg     780
ccctacctgg gcgtgaaccg ccacgaccag ggcagcgcc accaggcctg gagcctggtg     840
```

```
gtgatggtgc tgacccccct gaccaccgag gcccagatga acagcggcac cgtggaggtg      900
tacgccaaca tcgcccccac caacgtgttc gtggccggcg agaagcccgc caagcagggc      960
atcatccccg tggcctgcgc cgacggctac ggcggcttcc agaacaccga ccccaagacc     1020
gccgacccca tctacggcta cgtgtacaac cccagccgca acgactgcca cggccgctac     1080
agcaacctgc tggacgtggc cgaggcctgc ccacccctgc tgaacttcga cggcaagccc     1140
tacgtggtga ccaagaacaa cggcgacaag gtgatggccg ccttcgacgt ggccttcacc     1200
cacaaggtgc acaagaacac cttcctggcc ggcctggccg actactacac ccagtaccag     1260
ggcagcctga actaccactt catgtacacc ggccccaccc accacaaggc caagttcatg     1320
gtggcctaca tccccccggg catcgagacc gacaagctgc ccaagacccc cgaggacgcc     1380
gcccactgct accacagcga gtgggacacc ggcctgaaca ccagttcac cttcgccgtg     1440
ccctacgtga gcgccagcga cttcagctac acccacaccg acacccccgc catggccacc     1500
accaacggct gggtggccgt gttccaggtg accgacaccc acagcgccga ggccgccgtg     1560
gtggtgagcg tgagcgccgg ccccgacctg gagttccgct tccccatcga ccccgtgcgc     1620
cagaccacca cgccggcga gggcgccgag gtggtgacca ccgaccccag cacccacggc     1680
ggcaaggtga ccgagaagcg ccgcgtgcac accgacgtgg ccttcgtgct ggaccgcttc     1740
acccacgtgc acaccaacaa gaccaccttc gccgtggacc tgatggacac caaggagaag     1800
accctggtgg gcgccctgct gcgcgccgcc acctactact tctgcgacct ggagatcgcc     1860
tgcgtgggcg agcacaagcg cgtgttctgg cagcccaacg cgcccccg caccacccag     1920
ctgggcgaca ccccatggt gttcagccac aacaaggtga cccgcttcgc catcccctac     1980
accgccccccc accgcctgct gagcaccgtg tacaacggcg agtgcgagta caccaagacc     2040
gtgaccgcca tccgcggcga ccgcgaggtg ctggccgcca gtacagcag cgccaagcac     2100
accctgccca gcaccttcaa cttcggcttc gtgaccgccg acgagcccgt ggacgtgtac     2160
taccgcatga agcgcgccga gctgtactgc gtgaagaagc ccgtggccct gaaggtgaag     2220
gccaagaaca ccctgatcgt gaccgagagc ggcgcccccc ccaccgacct gcagaagatg     2280
gtgatgggca caccaagcc cgtggagctg atcctggacg gcaagaccgt ggccatctgc     2340
tgcgccaccg cgtgttcgg caccgcctac ctggtgcccc gccacctgtt cgccgagaag     2400
tacgacaaga tcatgctgga cggccgcgcc atgaccgaca cgactaccg cgtgttcgag     2460
ttcgagatca aggtgaaggg ccaggacatg ctgagcgacg ccgccctgat ggtgctgcac     2520
cgcggcaacc gcgtgcgcga catcaccaag cacttccgcg caccgcccg catgaagaag     2580
ggcaccccccg tggtgggcgt gatcaacaac gccgacgtgg ccgcctgat cttcagcggc     2640
gaggccctga cctacaagga catcgtggtg tgcatggacg gcgacaccat gcccggcctg     2700
ttcgcctaca aggccgccac caaggccggc tactgcggcg gcgccgtgct ggccaaggac     2760
ggcgccgaca ccttcatcgt gggcacccac agcgccggcg gcgcaacgg cgtgggctac     2820
tgcagctgcg tgagccgcag catgctgctg aagatgaagg cccacatcga ccccgagccc     2880
caccacgagg gcctgatcgt ggacacccgc gacgtggagg agcgcgtgca cgtgatgtga     2940
```

<210> SEQ ID NO 12
<211> LENGTH: 979
<212> TYPE: PRT
<213> ORGANISM: Artificial Sequence
<220> FEATURE:
<223> OTHER INFORMATION: consensus VP1-VP4 subtype SAT2 and consensus C3

<400> SEQUENCE: 12

```
Met Leu Asp Val Asp Trp Gln Asp Lys Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
    50                  55                  60

Gly Ser Thr Asp Thr Thr Ser Thr His Thr Asn Asn Thr Gln Asn Asn
65                  70                  75                  80

Asp Trp Phe Ser Lys Leu Ala Gln Ser Ala Ile Ser Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg His Gly Thr Thr Thr Ser Thr Thr Gln Ser
        115                 120                 125

Ser Val Gly Ile Thr Tyr Gly Tyr Ala Asp Ala Asp Ser Phe Arg Pro
    130                 135                 140

Gly Pro Asn Thr Ser Gly Leu Glu Thr Arg Val Glu Gln Ala Glu Arg
145                 150                 155                 160

Phe Phe Lys Glu Lys Leu Phe Asp Trp Thr Ser Asp Lys Pro Phe Gly
                165                 170                 175

Thr Leu Tyr Val Leu Glu Leu Pro Lys Asp His Lys Gly Ile Tyr Gly
            180                 185                 190

Ser Leu Thr Asp Ala Tyr Thr Tyr Met Arg Asn Gly Trp Asp Val Gln
        195                 200                 205

Val Ser Ala Thr Ser Thr Gln Phe Asn Gly Gly Ser Leu Leu Val Ala
    210                 215                 220

Met Val Pro Glu Leu Cys Ser Leu Lys Asp Arg Glu Glu Phe Gln Leu
225                 230                 235                 240

Thr Leu Tyr Pro His Gln Phe Ile Asn Pro Arg Thr Asn Thr Thr Ala
                245                 250                 255

His Ile Gln Val Pro Tyr Leu Gly Val Asn Arg His Asp Gln Gly Lys
            260                 265                 270

Arg His Gln Ala Trp Ser Leu Val Val Met Val Leu Thr Pro Leu Thr
        275                 280                 285

Thr Glu Ala Gln Met Asn Ser Gly Thr Val Glu Val Tyr Ala Asn Ile
    290                 295                 300

Ala Pro Thr Asn Val Phe Val Ala Gly Glu Lys Pro Ala Lys Gln Gly
305                 310                 315                 320

Ile Ile Pro Val Ala Cys Ala Asp Gly Tyr Gly Gly Phe Gln Asn Thr
                325                 330                 335

Asp Pro Lys Thr Ala Asp Pro Ile Tyr Gly Tyr Val Tyr Asn Pro Ser
            340                 345                 350

Arg Asn Asp Cys His Gly Arg Tyr Ser Asn Leu Leu Asp Val Ala Glu
        355                 360                 365

Ala Cys Pro Thr Leu Leu Asn Phe Asp Gly Lys Pro Tyr Val Val Thr
    370                 375                 380

Lys Asn Asn Gly Asp Lys Val Met Ala Ala Phe Asp Val Ala Phe Thr
385                 390                 395                 400

His Lys Val His Lys Asn Thr Phe Leu Ala Gly Leu Ala Asp Tyr Tyr
                405                 410                 415
```

-continued

```
Thr Gln Tyr Gln Gly Ser Leu Asn Tyr His Phe Met Tyr Thr Gly Pro
            420                 425                 430
Thr His His Lys Ala Lys Phe Met Val Ala Tyr Ile Pro Pro Gly Ile
        435                 440                 445
Glu Thr Asp Lys Leu Pro Lys Thr Pro Glu Asp Ala Ala His Cys Tyr
    450                 455                 460
His Ser Glu Trp Asp Thr Gly Leu Asn Ser Gln Phe Thr Phe Ala Val
465                 470                 475                 480
Pro Tyr Val Ser Ala Ser Asp Phe Ser Tyr Thr His Thr Asp Thr Pro
                485                 490                 495
Ala Met Ala Thr Thr Asn Gly Trp Val Ala Val Phe Gln Val Thr Asp
            500                 505                 510
Thr His Ser Ala Glu Ala Val Val Ser Val Ser Ala Gly Pro
        515                 520                 525
Asp Leu Glu Phe Arg Phe Pro Ile Asp Pro Val Arg Gln Thr Thr Ser
    530                 535                 540
Ala Gly Glu Gly Ala Glu Val Val Thr Thr Asp Pro Ser Thr His Gly
545                 550                 555                 560
Gly Lys Val Thr Glu Lys Arg Arg Val His Thr Asp Val Ala Phe Val
                565                 570                 575
Leu Asp Arg Phe Thr His Val His Thr Asn Lys Thr Thr Phe Ala Val
            580                 585                 590
Asp Leu Met Asp Thr Lys Glu Lys Thr Leu Val Gly Ala Leu Leu Arg
        595                 600                 605
Ala Ala Thr Tyr Tyr Phe Cys Asp Leu Glu Ile Ala Cys Val Gly Glu
    610                 615                 620
His Lys Arg Val Phe Trp Gln Pro Asn Gly Ala Pro Arg Thr Thr Gln
625                 630                 635                 640
Leu Gly Asp Asn Pro Met Val Phe Ser His Asn Lys Val Thr Arg Phe
                645                 650                 655
Ala Ile Pro Tyr Thr Ala Pro His Arg Leu Leu Ser Thr Val Tyr Asn
            660                 665                 670
Gly Glu Cys Glu Tyr Thr Lys Thr Val Thr Ala Ile Arg Gly Asp Arg
        675                 680                 685
Glu Val Leu Ala Ala Lys Tyr Ser Ser Ala Lys His Thr Leu Pro Ser
    690                 695                 700
Thr Phe Asn Phe Gly Phe Val Thr Ala Asp Glu Pro Val Asp Val Tyr
705                 710                 715                 720
Tyr Arg Met Lys Arg Ala Glu Leu Tyr Cys Val Lys Lys Pro Val Ala
                725                 730                 735
Leu Lys Val Lys Ala Lys Asn Thr Leu Ile Val Thr Glu Ser Gly Ala
            740                 745                 750
Pro Pro Thr Asp Leu Gln Lys Met Val Met Gly Asn Thr Lys Pro Val
        755                 760                 765
Glu Leu Ile Leu Asp Gly Lys Thr Val Ala Ile Cys Cys Ala Thr Gly
    770                 775                 780
Val Phe Gly Thr Ala Tyr Leu Val Pro Arg His Leu Phe Ala Glu Lys
785                 790                 795                 800
Tyr Asp Lys Ile Met Leu Asp Gly Arg Ala Met Thr Asp Ser Asp Tyr
                805                 810                 815
Arg Val Phe Glu Phe Glu Ile Lys Val Lys Gly Gln Asp Met Leu Ser
            820                 825                 830
```

```
Asp Ala Ala Leu Met Val Leu His Arg Gly Asn Arg Val Arg Asp Ile
        835                 840                 845

Thr Lys His Phe Arg Asp Thr Ala Arg Met Lys Lys Gly Thr Pro Val
    850                 855                 860

Val Gly Val Ile Asn Asn Ala Asp Val Gly Arg Leu Ile Phe Ser Gly
865                 870                 875                 880

Glu Ala Leu Thr Tyr Lys Asp Ile Val Val Cys Met Asp Gly Asp Thr
                885                 890                 895

Met Pro Gly Leu Phe Ala Tyr Lys Ala Ala Thr Lys Ala Gly Tyr Cys
            900                 905                 910

Gly Gly Ala Val Leu Ala Lys Asp Gly Ala Asp Thr Phe Ile Val Gly
        915                 920                 925

Thr His Ser Ala Gly Gly Arg Asn Gly Val Gly Tyr Cys Ser Cys Val
    930                 935                 940

Ser Arg Ser Met Leu Leu Lys Met Lys Ala His Ile Asp Pro Glu Pro
945                 950                 955                 960

His His Glu Gly Leu Ile Val Asp Thr Arg Asp Val Glu Glu Arg Val
                965                 970                 975

His Val Met

<210> SEQ ID NO 13
<211> LENGTH: 2937
<212> TYPE: DNA
<213> ORGANISM: Artificial Sequence
<220> FEATURE:
<223> OTHER INFORMATION: nucleic acid, consensus VP1-VP4 subtype SAT3
      and consensus C3

<400> SEQUENCE: 13
atgctggacg tggactggca ggaccgcgcc ggcctgttcc tgcgcggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc     180 ggcagcaacg agggcagcac cgacaccacc agcacccaca ccaacaacac ccagaacaac     240
gactggttca gcaagctggc ccagagcgcc atcagcggcc tgttcggcgc cctgctggcc     300
gacaagaaga ccgaggagac caccacctg gaggaccgca tcctgaccac ccgccacaac     360
accaccacca gcaccaccca gagcagcgtg gcgtgacct acggctacgt gagcgccgac     420
cgcttcctgc ccggccccaa caccagcggc ctggagagcc gcgtggagca ggccgagcgc     480
ttcttcaagg agaagctgtt cacctggacc gccagccagg agtacgccca cgtgcacctg     540
ctggagctgc ccaccgacca agggcatc tacggcgcca tggtggacag ccacgcctac     600
gtgcgcaacg ctgggacgt gcaggtgacc gccaccagca cccagttcaa cggcggcacc     660
ctgctggtgg ccatggtgcc cgagctgcac agcctggaca cccgcgacgt gagccagctg     720
accctgttcc cccaccagtt catcaacccc gcaccaaca ccaccgccca catcgtggtg     780
ccctacgtgg gcgtgaaccg ccacgaccag gtgcagatgc acaaggcctg gaccctggtg     840
gtggccgtga tggccccct gaccaccagc agcatgggcc aggacaacgt ggaggtgtac     900
gccaacatcg cccccaccaa cgtgtacgtg gccggcgagc gccccagcaa gagggcatc     960 atccccgtgg cctgcaacga cggctacggc ggcttccaga caccgaccc caagaccgcc    1020 gaccccatct acggcctggt gagcaacccc cccgcaccg ccttcccgg cgcttcacc    1080 aacctgctgg acgtggccga ggcctgcccc accttcctgg acttcgacgg cgtgccctac    1140
gtgaagacca cccacaacag cggcagcaag atcctgaccc acatcgacct ggccttcggc    1200
```

```
cacaagagct tcaagaacac ctacctggcc ggcctggccc agtactacgc ccagtacagc    1260
ggcagcatca acctgcactt catgtacacc ggccccaccc agagcaaggc ccgcttcatg    1320
gtggcctaca tccccccggg caccaccgtg cccaacaccc ccgagcaggc cgcccactgc    1380
taccacagcg agtgggacac cggcctgaac agcaagttca ccttcaccgt gccctacatg    1440
agcgccgccg acttcgccta cacctactgc gacgagcccg agcaggccag cgcccagggc    1500
tgggtgaccc tgtaccagat caccgacacc acgaccccg acagcgccgt gctggtgagc    1560
gtgagcgccg cgccgacttc gagctgcgc ctgcccatca cccccgccgc ccagaccacc    1620
agcgccggcg agggcgccga cgtggtgacc accgacgtga ccacccacgg cggcgaggtg    1680
agcgtgcccc gccgccagca caccaacgtg gagttcctgc tggaccgctt cacccacatc    1740
ggcaccatca acgccaccg caccatctgc ctgatggaca ccaaggagca cccctggtg    1800 ggcgccatcc tgcgcagcgc cacctactac ttctgcgacc tggaggtggc cgtgctgggc    1860
aacgccaagt acgccgcctg ggtgcccaac ggctgccccc acaccgaccg cgtggaggac    1920
aaccccgtgg tgcacagcaa gggcagcgtg gtgcgcttcg ccctgcccta caccgccccc    1980
cacggcgtgc tggccaccgt gtacaacggc aactgcaagt acagcaccac ccagcgcgtg    2040
gccccccgcc gcggcgacct gggcgtgctg agccagcgcg tggagaacga ccacccgc     2100 tgcatcccca ccaccttcaa cttcggccgc ctgctgtgcg agagcggcga cgtgtactac    2160
cgcatgaagc gcaccgagct gtactgcgtg aagaagcccg tggccctgaa ggtgaaggcc    2220
aagaacaccc tgatcgtgac cgagagcggc gccccccca ccgacctgca gaagatggtg    2280
atgggcaaca ccaagcccgt ggagctgatc ctggacggca gaccgtggc catctgctgc    2340 gccaccggcg tgttcggcac cgcctacctg gtgccccgcc acctgttcgc cgagaagtac    2400
gacaagatca tgctggacgg ccgcgccatg accgacagcg actaccgcgt gttcgagttc    2460
gagatcaagg tgaagggcca ggacatgctg agcgacgccg ccctgatggt gctgcaccgc    2520
ggcaaccgcg tgcgcgacat caccaagcac ttccgcgaca ccgcccgcat gaagaaggc    2580 acccccgtgg tgggcgtgat caacaacgcc gacgtgggcc gcctgatctt cagcggcgag    2640
gccctgacct acaaggacat cgtggtgtgc atggacggca caccatgcc cggcctgttc    2700 gcctacaagg ccgccaccaa ggccggctac tgcggcggcg ccgtgctggc caaggacggc    2760
gccgacacct tcatcgtggg cacccacagc gccggcggcc gcaacggcgt gggctactgc    2820
agctgcgtga ccgcagcat gctgctgaag atgaaggccc acatcgaccc cgagccccac    2880
cacgagggcc tgatcgtgga cacccgcgac gtggaggagc gcgtgcacgt gatgtga       2937
```

<210> SEQ ID NO 14
<211> LENGTH: 978
<212> TYPE: PRT
<213> ORGANISM: Artificial Sequence
<220> FEATURE:
<223> OTHER INFORMATION: consensus VP1-VP4 subtype SAT3 and consensus C3

<400> SEQUENCE: 14

```
Met Leu Asp Val Asp Trp Gln Asp Arg Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
```

```
            50                  55                  60
Gly Ser Thr Asp Thr Thr Ser Thr His Thr Asn Asn Thr Gln Asn Asn
 65                  70                  75                  80

Asp Trp Phe Ser Lys Leu Ala Gln Ser Ala Ile Ser Gly Leu Phe Gly
                 85                  90                  95

Ala Leu Leu Ala Asp Lys Lys Thr Glu Thr Thr His Leu Glu Asp
                100                 105                 110

Arg Ile Leu Thr Thr Arg His Asn Thr Thr Ser Thr Thr Gln Ser
                115                 120                 125

Ser Val Gly Val Thr Tyr Gly Tyr Val Ser Ala Asp Arg Phe Leu Pro
                130                 135                 140

Gly Pro Asn Thr Ser Gly Leu Glu Ser Arg Val Glu Gln Ala Glu Arg
145                 150                 155                 160

Phe Phe Lys Glu Lys Leu Phe Thr Trp Thr Ala Ser Gln Glu Tyr Ala
                165                 170                 175

His Val His Leu Leu Glu Leu Pro Thr Asp His Lys Gly Ile Tyr Gly
                180                 185                 190

Ala Met Val Asp Ser His Ala Tyr Val Arg Asn Gly Trp Asp Val Gln
                195                 200                 205

Val Thr Ala Thr Ser Thr Gln Phe Asn Gly Gly Thr Leu Leu Val Ala
210                 215                 220

Met Val Pro Glu Leu His Ser Leu Asp Thr Arg Asp Val Ser Gln Leu
225                 230                 235                 240

Thr Leu Phe Pro His Gln Phe Ile Asn Pro Arg Thr Asn Thr Thr Ala
                245                 250                 255

His Ile Val Val Pro Tyr Val Gly Val Asn Arg His Asp Gln Val Gln
                260                 265                 270

Met His Lys Ala Trp Thr Leu Val Val Ala Val Met Ala Pro Leu Thr
                275                 280                 285

Thr Ser Ser Met Gly Gln Asp Asn Val Glu Val Tyr Ala Asn Ile Ala
290                 295                 300

Pro Thr Asn Val Tyr Val Ala Gly Glu Arg Pro Ser Lys Gln Gly Ile
305                 310                 315                 320

Ile Pro Val Ala Cys Asn Asp Gly Tyr Gly Gly Phe Gln Asn Thr Asp
                325                 330                 335

Pro Lys Thr Ala Asp Pro Ile Tyr Gly Leu Val Ser Asn Pro Pro Arg
                340                 345                 350

Thr Ala Phe Pro Gly Arg Phe Thr Asn Leu Leu Asp Val Ala Glu Ala
                355                 360                 365

Cys Pro Thr Phe Leu Asp Phe Asp Gly Val Pro Tyr Val Lys Thr Thr
                370                 375                 380

His Asn Ser Gly Ser Lys Ile Leu Thr His Ile Asp Leu Ala Phe Gly
385                 390                 395                 400

His Lys Ser Phe Lys Asn Thr Tyr Leu Ala Gly Leu Ala Gln Tyr Tyr
                405                 410                 415

Ala Gln Tyr Ser Gly Ser Ile Asn Leu His Phe Met Tyr Thr Gly Pro
                420                 425                 430

Thr Gln Ser Lys Ala Arg Phe Met Val Ala Tyr Ile Pro Pro Gly Thr
                435                 440                 445

Thr Val Pro Asn Thr Pro Glu Gln Ala Ala His Cys Tyr His Ser Glu
                450                 455                 460

Trp Asp Thr Gly Leu Asn Ser Lys Phe Thr Phe Thr Val Pro Tyr Met
465                 470                 475                 480
```

```
Ser Ala Ala Asp Phe Ala Tyr Thr Tyr Cys Asp Glu Pro Glu Gln Ala
                485                 490                 495

Ser Ala Gln Gly Trp Val Thr Leu Tyr Gln Ile Thr Asp Thr His Asp
            500                 505                 510

Pro Asp Ser Ala Val Leu Val Ser Val Ser Ala Gly Ala Asp Phe Glu
            515                 520                 525

Leu Arg Leu Pro Ile Asn Pro Ala Ala Gln Thr Thr Ser Ala Gly Glu
        530                 535                 540

Gly Ala Asp Val Val Thr Thr Asp Val Thr Thr His Gly Gly Glu Val
545                 550                 555                 560

Ser Val Pro Arg Arg Gln His Thr Asn Val Glu Phe Leu Leu Asp Arg
                565                 570                 575

Phe Thr His Ile Gly Thr Ile Asn Gly His Arg Thr Ile Cys Leu Met
                580                 585                 590

Asp Thr Lys Glu His Thr Leu Val Gly Ala Ile Leu Arg Ser Ala Thr
                595                 600                 605

Tyr Tyr Phe Cys Asp Leu Glu Val Ala Val Leu Gly Asn Ala Lys Tyr
        610                 615                 620

Ala Ala Trp Val Pro Asn Gly Cys Pro His Thr Asp Arg Val Glu Asp
625                 630                 635                 640

Asn Pro Val Val His Ser Lys Gly Ser Val Val Arg Phe Ala Leu Pro
                645                 650                 655

Tyr Thr Ala Pro His Gly Val Leu Ala Thr Val Tyr Asn Gly Asn Cys
                660                 665                 670

Lys Tyr Ser Thr Thr Gln Arg Val Ala Pro Arg Arg Gly Asp Leu Gly
        675                 680                 685

Val Leu Ser Gln Arg Val Glu Asn Glu Thr Thr Arg Cys Ile Pro Thr
        690                 695                 700

Thr Phe Asn Phe Gly Arg Leu Leu Cys Glu Ser Gly Asp Val Tyr Tyr
705                 710                 715                 720

Arg Met Lys Arg Thr Glu Leu Tyr Cys Val Lys Pro Val Ala Leu
                725                 730                 735

Lys Val Lys Ala Lys Asn Thr Leu Ile Val Thr Glu Ser Gly Ala Pro
                740                 745                 750

Pro Thr Asp Leu Gln Lys Met Val Met Gly Asn Thr Lys Pro Val Glu
            755                 760                 765

Leu Ile Leu Asp Gly Lys Thr Val Ala Ile Cys Cys Ala Thr Gly Val
        770                 775                 780

Phe Gly Thr Ala Tyr Leu Val Pro Arg His Leu Phe Ala Glu Lys Tyr
785                 790                 795                 800

Asp Lys Ile Met Leu Asp Gly Arg Ala Met Thr Asp Ser Asp Tyr Arg
                805                 810                 815

Val Phe Glu Phe Glu Ile Lys Val Lys Gly Gln Asp Met Leu Ser Asp
                820                 825                 830

Ala Ala Leu Met Val Leu His Arg Gly Asn Arg Val Arg Asp Ile Thr
                835                 840                 845

Lys His Phe Arg Asp Thr Ala Arg Met Lys Lys Gly Thr Pro Val Val
        850                 855                 860

Gly Val Ile Asn Asn Ala Asp Val Gly Arg Leu Ile Phe Ser Gly Glu
865                 870                 875                 880

Ala Leu Thr Tyr Lys Asp Ile Val Val Cys Met Asp Gly Asp Thr Met
                885                 890                 895
```

```
Pro Gly Leu Phe Ala Tyr Lys Ala Ala Thr Lys Ala Gly Tyr Cys Gly
            900                 905                 910
Gly Ala Val Leu Ala Lys Asp Gly Ala Asp Thr Phe Ile Val Gly Thr
        915                 920                 925
His Ser Ala Gly Gly Arg Asn Gly Val Gly Tyr Cys Ser Cys Val Ser
    930                 935                 940
Arg Ser Met Leu Leu Lys Met Lys Ala His Ile Asp Pro Glu Pro His
945                 950                 955                 960
His Glu Gly Leu Ile Val Asp Thr Arg Asp Val Glu Glu Arg Val His
                965                 970                 975
Val Met

<210> SEQ ID NO 15
<211> LENGTH: 756
<212> TYPE: DNA
<213> ORGANISM: Artificial Sequence
<220> FEATURE:
<223> OTHER INFORMATION: consensus FMDV Protease c3 sequence

<400> SEQUENCE: 15
tactgcgtga agaagcccgt ggccctgaag gtgaaggcca agaacaccct gatcgtgacc      60
gagagcggcg ccccccccac cgacctgcag aagatggtga tgggcaacac caagcccgtg     120
gagctgatcc tggacggcaa gaccgtggcc atctgctgcg ccaccggcgt gttcggcacc     180
gcctacctgg tgccccgcca cctgttcgcc gagaagtacg acaagatcat gctggacggc     240
cgcgccatga ccgacagcga ctaccgcgtg ttcgagttcg agatcaaggt gaagggccag     300
gacatgctga gcgacgccgc cctgatggtg ctgcaccgcg gcaaccgcgt gcgcgacatc     360
accaagcact ccgcgacac cgcccgcatg aagaagggca cccccgtggt gggcgtgatc     420
aacaacgccg acgtgggccg cctgatcttc agcggcgagg ccctgaccta caaggacatc     480
gtggtgtgca tggacggcga caccatgccc ggcctgttcg cctacaaggc cgccaccaag     540
gccggctact gcggcggcgc cgtgctggcc aaggacggcg ccgacacctt catcgtgggc     600
acccacagcg ccggcggccg caacggcgtg ggctactgca gctgcgtgag ccgcagcatg     660
ctgctgaaga tgaaggccca catcgacccc gagccccacc acgagggcct gatcgtggac     720
acccgcgacg tggaggagcg cgtgcacgtg atgtga                               756

<210> SEQ ID NO 16
<211> LENGTH: 251
<212> TYPE: PRT
<213> ORGANISM: Artificial Sequence
<220> FEATURE:
<223> OTHER INFORMATION: Amino Acid consensus Protease c3 sequence

<400> SEQUENCE: 16

Tyr Cys Val Lys Lys Pro Val Ala Leu Lys Val Lys Ala Lys Asn Thr
1               5                  10                  15
Leu Ile Val Thr Glu Ser Gly Ala Pro Pro Thr Asp Leu Gln Lys Met
            20                  25                  30
Val Met Gly Asn Thr Lys Pro Val Glu Leu Ile Leu Asp Gly Lys Thr
        35                  40                  45
Val Ala Ile Cys Cys Ala Thr Gly Val Phe Gly Thr Ala Tyr Leu Val
    50                  55                  60
Pro Arg His Leu Phe Ala Glu Lys Tyr Asp Lys Ile Met Leu Asp Gly
65                  70                  75                  80
Arg Ala Met Thr Asp Ser Asp Tyr Arg Val Phe Glu Phe Glu Ile Lys
```

|  |  |  | 85 |  |  |  |  | 90 |  |  |  |  | 95 |  |  |
|---|---|---|---|---|---|---|---|---|---|---|---|---|---|---|---|
| Val | Lys | Gly | Gln | Asp | Met | Leu | Ser | Asp | Ala | Ala | Leu | Met | Val | Leu | His |
|  |  |  | 100 |  |  |  |  | 105 |  |  |  |  | 110 |  |  |
| Arg | Gly | Asn | Arg | Val | Arg | Asp | Ile | Thr | Lys | His | Phe | Arg | Asp | Thr | Ala |
|  |  |  | 115 |  |  |  |  | 120 |  |  |  |  | 125 |  |  |
| Arg | Met | Lys | Lys | Gly | Thr | Pro | Val | Val | Gly | Val | Ile | Asn | Asn | Ala | Asp |
|  |  |  | 130 |  |  |  |  | 135 |  |  |  |  | 140 |  |  |
| Val | Gly | Arg | Leu | Ile | Phe | Ser | Gly | Glu | Ala | Leu | Thr | Tyr | Lys | Asp | Ile |
| 145 |  |  |  |  | 150 |  |  |  |  | 155 |  |  |  |  | 160 |
| Val | Val | Cys | Met | Asp | Gly | Asp | Thr | Met | Pro | Gly | Leu | Phe | Ala | Tyr | Lys |
|  |  |  |  |  | 165 |  |  |  |  | 170 |  |  |  |  | 175 |
| Ala | Ala | Thr | Lys | Ala | Gly | Tyr | Cys | Gly | Gly | Ala | Val | Leu | Ala | Lys | Asp |
|  |  |  | 180 |  |  |  |  | 185 |  |  |  |  | 190 |  |  |
| Gly | Ala | Asp | Thr | Phe | Ile | Val | Gly | Thr | His | Ser | Ala | Gly | Gly | Arg | Asn |
|  |  |  | 195 |  |  |  |  | 200 |  |  |  |  | 205 |  |  |
| Gly | Val | Gly | Tyr | Cys | Ser | Cys | Val | Ser | Arg | Ser | Met | Leu | Leu | Lys | Met |
|  |  |  | 210 |  |  |  |  | 215 |  |  |  |  | 220 |  |  |
| Lys | Ala | His | Ile | Asp | Pro | Glu | Pro | His | His | Glu | Gly | Leu | Ile | Val | Asp |
| 225 |  |  |  |  | 230 |  |  |  |  | 235 |  |  |  |  | 240 |
| Thr | Arg | Asp | Val | Glu | Glu | Arg | Val | His | Val | Met |  |  |  |  |  |
|  |  |  |  |  | 245 |  |  |  |  | 250 |  |  |  |  |  |

```
<210> SEQ ID NO 17
<211> LENGTH: 2160
<212> TYPE: DNA
<213> ORGANISM: Artificial Sequence
<220> FEATURE:
<223> OTHER INFORMATION: nucleic acid, consensus vp1-4 Subtype A

<400

```
accacccgca ccgacgagac ccgcctgctg gccaagttcg acgtgagcct ggccgccaag    1200
cacatgagca acacctacct gagcggcatc gcccagtact acacccagta cagcggcacc    1260
atcaacctgc acttcatgtt caccggcagc accgacagca aggcccgcta catggtggcc    1320
tacatccccc ccggcgtgga gaccccccc gacacccccg agcgcgccgc ccactgcatc    1380
cacgccgagt gggacaccgg cctgaacagc aagttcacct tcagcatccc ctacgtgagc    1440
gccgccgact acgcctacac cgccagcgac ccgccgaga ccaccaacgt gcagggctgg    1500
gtgtgcgtgt accagatcac ccacggcaag gccgagaacg cacccctggt ggtgagcgtg    1560
agcgccggca aggacttcga gctgcgcctg cccatcgacc ccgccagca gaccaccgcc    1620 accggcgaga gcgccgaccc cgtgaccacc accgtggaga actacggcgg cgagacccag    1680
gtgcagcgcc gccaccacac cgacgtgggc ttcatcatgg accgcttcgt gaagatcaac    1740
agccccaagc ccacccacgt gatcgacctg atgcagaccc accagcacgg cctggtgggc    1800
gccctgctgc gcgccgccac ctactacttc agcgacctgg agatcgtggt gcgccacgac    1860
ggcctgacct gggtgcccaa cggcgccccc gagagcgccc tgagcaacac cagcaacccc    1920
accgcctaca caaggcccc cttcacccgc ctggccctgc cctacaccgc ccccaccgc     1980 gtgctggcca ccgtgtacaa cggcaccagc aagtacaccg tgagcggcag cagccgccgc    2040
ggcgacctgg gcagcctggc cgcccgcgtg gccaagcagc tgcccgccag cttcaactac    2100
ggcgccatca aggccgacac catccacgag ctgctggtgc gcatgaagcg cgccgagctg    2160
```

<210> SEQ ID NO 18
<211> LENGTH: 720
<212> TYPE: PRT
<213> ORGANISM: Artificial Sequence
<220> FEATURE:
<223> OTHER INFORMATION: Consensus vp1-4 Subtype A

<400> SEQUENCE: 18

```
Met Leu Asn Gly Asp Trp Lys Ala Lys Val Gln Arg Lys Leu Lys Gly
1               5                   10                  15

Ala Gly Gln Ser Ser Pro Ala Thr Gly Ser Gln Asn Gln Ser Gly Asn

```
                    180                 185                 190
His Leu Val Asp Ser Tyr Ala Tyr Met Arg Asn Gly Trp Asp Val Glu
            195                 200                 205
Val Ser Ala Val Gly Asn Gln Phe Asn Gly Gly Cys Leu Leu Val Ala
        210                 215                 220
Met Val Pro Glu Trp Lys Glu Phe Asp Thr Arg Glu Lys Tyr Gln Leu
225                 230                 235                 240
Thr Leu Phe Pro His Gln Phe Ile Ser Pro Arg Thr Asn Met Thr Ala
                245                 250                 255
His Ile Thr Val Pro Tyr Leu Gly Val Asn Arg Tyr Asp Gln Tyr Lys
            260                 265                 270
Lys His Lys Pro Trp Thr Leu Val Met Val Val Ser Pro Leu Thr
        275                 280                 285
Val Asn Thr Ala Ala Gln Ile Lys Val Tyr Ala Asn Ile Ala Pro Thr
    290                 295                 300
Tyr Val His Val Ala Gly Glu Leu Pro Ser Lys Glu Gly Ile Phe Pro
305                 310                 315                 320
Val Ala Cys Ala Asp Gly Tyr Gly Leu Val Thr Thr Asp Pro Lys
                325                 330                 335
Thr Ala Asp Pro Ala Tyr Gly Lys Val Tyr Asn Pro Pro Arg Thr Asn
            340                 345                 350
Tyr Pro Gly Arg Phe Thr Asn Leu Leu Asp Val Ala Glu Ala Cys Pro
        355                 360                 365
Thr Phe Leu Cys Phe Asp Asp Gly Lys Pro Tyr Val Thr Thr Arg Thr
    370                 375                 380
Asp Glu Thr Arg Leu Leu Ala Lys Phe Asp Val Ser Leu Ala Ala Lys
385                 390                 395                 400
His Met Ser Asn Thr Tyr Leu Ser Gly Ile Ala Gln Tyr Tyr Thr Gln
                405                 410                 415
Tyr Ser Gly Thr Ile Asn Leu His Phe Met Phe Thr Gly Ser Thr Asp
            420                 425                 430
Ser Lys Ala Arg Tyr Met Val Ala Tyr Ile Pro Pro Gly Val Glu Thr
        435                 440                 445
Pro Pro Asp Thr Pro Glu Arg Ala Ala His Cys Ile His Ala Glu Trp
    450                 455                 460
Asp Thr Gly Leu Asn Ser Lys Phe Thr Phe Ser Ile Pro Tyr Val Ser
465                 470                 475                 480
Ala Ala Asp Tyr Ala Tyr Thr Ala Ser Asp Thr Ala Glu Thr Thr Asn
                485                 490                 495
Val Gln Gly Trp Val Cys Val Tyr Gln Ile Thr His Gly Lys Ala Glu
            500                 505                 510
Asn Asp Thr Leu Val Val Ser Val Ser Ala Gly Lys Asp Phe Glu Leu
        515                 520                 525
Arg Leu Pro Ile Asp Pro Arg Gln Gln Thr Thr Ala Thr Gly Glu Ser
    530                 535                 540
Ala Asp Pro Val Thr Thr Thr Val Glu Asn Tyr Gly Gly Glu Thr Gln
545                 550                 555                 560
Val Gln Arg Arg His His Thr Asp Val Gly Phe Ile Met Asp Arg Phe
                565                 570                 575
Val Lys Ile Asn Ser Pro Lys Pro Thr His Val Ile Asp Leu Met Gln
            580                 585                 590
Thr His Gln His Gly Leu Val Gly Ala Leu Leu Arg Ala Ala Thr Tyr
        595                 600                 605
```

```
Tyr Phe Ser Asp Leu Glu Ile Val Val Arg His Asp Gly Leu Thr Trp
        610                 615                 620

Val Pro Asn Gly Ala Pro Glu Ser Ala Leu Ser Asn Thr Ser Asn Pro
625                 630                 635                 640

Thr Ala Tyr Asn Lys Ala Pro Phe Thr Arg Leu Ala Leu Pro Tyr Thr
                645                 650                 655

Ala Pro His Arg Val Leu Ala Thr Val Tyr Asn Gly Thr Ser Lys Tyr
            660                 665                 670

Thr Val Ser Gly Ser Ser Arg Arg Gly Asp Leu Gly Ser Leu Ala Ala
        675                 680                 685

Arg Val Ala Lys Gln Leu Pro Ala Ser Phe Asn Tyr Gly Ala Ile Lys
    690                 695                 700

Ala Asp Thr Ile His Glu Leu Leu Val Arg Met Lys Arg Ala Glu Leu
705                 710                 715                 720

<210> SEQ ID NO 19
<211> LENGTH: 2160
<212> TYPE: DNA
<213> ORGANISM: Artificial Sequence
<220> FEATURE:
<223> OTHER INFORMATION: nucleic acid, consensus vp1-4 Subtype Asia 1

<400> SEQUENCE: 19
atgctgaacg cgagtggaa ggccaaggtg cagaagcgcc tgaagggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc     180 ggcagcaacg agggcagcac cgacaccacc agcacccaca ccaacaacac ccagaacaac     240
gactggttca gccgcctggc cagcagcgcc ttcagcggcc tgttcggcgc cctgctggcc     300
gacaagaaga ccgaggagac caccctgctg gaggaccgca tcctgaccac ccgcaacggc     360
cacaccacca gcaccaccca gagcagcgtg gcgtgaccct acggctacgc cgtggccgag     420
gacgccgtga gcggccccaa caccagcggc ctggagaccc gcgtgcagca ggccgagcgc     480
ttcttcaaga agcaccctgtt cgactggacc cccaacctgg ccttcggcca ctgccactac     540
ctggagctgc ccaccgagca agggcgtg tacggcagcc tgatggacag ctacgcctac     600
atgcgcaacg gctgggacat cgaggtgacc gccgtgggca ccagttcaa cggcggctgc     660 ctgctggtgg ccctggtgcc cgagctgaag agcctggaca cccgccagaa gtaccagctg     720 acccctgttcc ccaccagtt catcaacccc cgcaccaaca tgaccgccca catcaacgtg     780
cccttcgtgg gcgtgaaccg ctacgaccag tacgccctgc acaagccctg gaccctggtg     840
gtgatggtgg tggccccccct gaccgtgaag accggcggca gcgagcagat caaggtgtac     900
atgaacgccg ccccccaccta cgtgcacgtg gccggcgagc tgcccagcaa ggagggcatc     960
gtgcccgtgg cctgcgccga cggctacggc aacatggtga ccaccgaccc caagaccgcc    1020
gaccccgtgt acggcaaggt gttcaacccc cccgcacca acctgccccgg ccgcttcacc    1080 aacttcctgg acgtggccga ggcctgcccc accttcctgc gcttcggcga ggtgcccttc    1140
gtgaagaccg tgaacagcgg cgaccgcctg ctggccaagt cgacgtgag cctgccgcc    1200 ggccacatga gcaacaccta cctggccggc ctggcccagt actacccca gtacagcggc    1260 accatgaacg tgcacttcat gttcaccggc cccaccgacg ccaaggcccg ctacatggtg    1320
gcctacatcc ccccggcat gacccccccc ccgaccccg agcgcgccgc ccactgcatc    1380
cacagcgagt gggacaccgg cctgaacagc aagttcacct tcagcatccc ctacctgagc    1440
```

```
gccgccgact acgcctacac cgccagcgac accgccgaga ccaccagcgt gcagggctgg    1500
gtgtgcatct accagatcac ccacggcaag gccgagggcg acgccctggt ggtgagcgtg    1560
agcgccggca aggacttcga gttccgcctg cccgtggacg cccgccgcca gaccaccacc    1620
accggcgaga gcgccgaccc cgtgaccacc accgtggaga actacggcgg cgagacccag    1680
accgcccgcc gcctgcacac cgacgtggcc ttcgtgctgg accgcttcgt gaagctgacc    1740
gcccccaaga cacccagac cctggacctg atgcagatcc ccagccacac cctggtgggc     1800
gccctgctgc gcagcgccac ctactacttc agcgacctgg aggtggccct ggtgcacacc    1860
ggccccgtga cctgggtgcc caacggcagc cccaaggacg ccctggacaa ccagaccaac    1920
cccaccgcct accagaagca gcccatcacc cgcctggccc tgccctacac cgcccccac    1980 cgcgtgctgg ccaccgtgta caacggcaag accacctacg gcgagacccc cagccgccgc    2040
ggcgacatgg ccgccctggc ccagcgcctg agcgagcgcc tgcccaccag cttcaactac    2100
ggcgccgtga aggccgagac catcaccgag ctgctgatcc gcatgaagcg cgccgagacc    2160
```

<210> SEQ ID NO 20
<211> LENGTH: 704
<212> TYPE: PRT
<213> ORGANISM: Artificial Sequence
<220> FEATURE:
<223> OTHER INFORMATION: Consensus vp1-4 Subtype Asia 1

<400> SEQUENCE: 20

```
Ala Gly Gln Ser Ser Pro Ala Thr Gly Ser Gln Asn Gln Ser Gly Asn
  1               5                  10                  15

Thr Gly Ser Ile Ile Asn Asn Tyr Tyr Met Gln Gln Tyr Gln Asn Ser
             20                  25                  30

Met Asp Thr Gln Leu Gly Asp Asn Ala Ile Ser Gly Gly Ser Asn Glu
         35                  40                  45

Gly Ser Thr Asp Thr Thr Ser Thr His Thr Asn Asn Thr Gln Asn Asn
     50                  55                  60

Asp Trp Phe Ser Arg Leu Ala Ser Ser Ala Phe Ser Gly Leu Phe Gly
 65                  70                  75                  80

Ala Leu Leu Ala Asp Lys Lys Thr Glu Glu Thr Thr Leu Leu Glu Asp
                 85                  90                  95

Arg Ile Leu Thr Thr Arg Asn Gly His Thr Thr Ser Thr Thr Gln Ser
            100                 105                 110

Ser Val Gly Val Thr Tyr Gly Tyr Ala Val Ala Glu Asp Ala Val Ser
        115                 120                 125

Gly Pro Asn Thr Ser Gly Leu Glu Thr Arg Val Gln Gln Ala Glu Arg
    130                 135                 140

Phe Phe Lys Lys His Leu Phe Asp Trp Thr Pro Asn Leu Ala Phe Gly
145                 150                 155                 160

His Cys His Tyr Leu Glu Leu Pro Thr Glu His Lys Gly Val Tyr Gly
                165                 170                 175

Ser Leu Met Asp Ser Tyr Ala Tyr Met Arg Asn Gly Trp Asp Ile Glu
            180                 185                 190

Val Thr Ala Val Gly Asn Gln Phe Asn Gly Gly Cys Leu Leu Val Ala
        195                 200                 205

Leu Val Pro Glu Leu Lys Ser Leu Asp Thr Arg Gln Lys Tyr Gln Leu
    210                 215                 220

Thr Leu Phe Pro His Gln Phe Ile Asn Pro Arg Thr Asn Met Thr Ala
225                 230                 235                 240
```

-continued

```
His Ile Asn Val Pro Phe Val Gly Val Asn Arg Tyr Asp Gln Tyr Ala
                245                 250                 255
Leu His Lys Pro Trp Thr Leu Val Val Met Val Ala Pro Leu Thr
        260                 265                 270
Val Lys Thr Gly Gly Ser Glu Gln Ile Lys Val Tyr Met Asn Ala Ala
        275                 280                 285
Pro Thr Tyr Val His Val Ala Gly Glu Leu Pro Ser Lys Glu Gly Ile
    290                 295                 300
Val Pro Val Ala Cys Ala Asp Gly Tyr Gly Asn Met Val Thr Thr Asp
305                 310                 315                 320
Pro Lys Thr Ala Asp Pro Val Tyr Gly Lys Val Phe Asn Pro Pro Arg
                325                 330                 335
Thr Asn Leu Pro Gly Arg Phe Thr Asn Phe Leu Asp Val Ala Glu Ala
                340                 345                 350
Cys Pro Thr Phe Leu Arg Phe Gly Glu Val Pro Phe Val Lys Thr Val
                355                 360                 365
Asn Ser Gly Asp Arg Leu Leu Ala Lys Phe Asp Val Ser Leu Ala Ala
    370                 375                 380
Gly His Met Ser Asn Thr Tyr Leu Ala Gly Leu Ala Gln Tyr Tyr Thr
385                 390                 395                 400
Gln Tyr Ser Gly Thr Met Asn Val His Phe Met Phe Thr Gly Pro Thr
                405                 410                 415
Asp Ala Lys Ala Arg Tyr Met Val Ala Tyr Ile Pro Pro Gly Met Thr
                420                 425                 430
Pro Pro Thr Asp Pro Glu Arg Ala Ala His Cys Ile His Ser Glu Trp
                435                 440                 445
Asp Thr Gly Leu Asn Ser Lys Phe Thr Phe Ser Ile Pro Tyr Leu Ser
    450                 455                 460
Ala Ala Asp Tyr Ala Tyr Thr Ala Ser Asp Thr Ala Glu Thr Thr Ser
465                 470                 475                 480
Val Gln Gly Trp Val Cys Ile Tyr Gln Ile Thr His Gly Lys Ala Glu
                485                 490                 495
Gly Asp Ala Leu Val Val Ser Val Ser Ala Gly Lys Asp Phe Glu Phe
    500                 505                 510
Arg Leu Pro Val Asp Ala Arg Arg Gln Thr Thr Thr Thr Gly Glu Ser
    515                 520                 525
Ala Asp Pro Val Thr Thr Thr Val Glu Asn Tyr Gly Gly Glu Thr Gln
    530                 535                 540
Thr Ala Arg Arg Leu His Thr Asp Val Ala Phe Val Leu Asp Arg Phe
545                 550                 555                 560
Val Lys Leu Thr Ala Pro Lys Asn Thr Gln Thr Leu Asp Leu Met Gln
                565                 570                 575
Ile Pro Ser His Thr Leu Val Gly Ala Leu Leu Arg Ser Ala Thr Tyr
                580                 585                 590
Tyr Phe Ser Asp Leu Glu Val Ala Leu Val His Thr Gly Pro Val Thr
                595                 600                 605
Trp Val Pro Asn Gly Ser Pro Lys Asp Ala Leu Asp Asn Gln Thr Asn
    610                 615                 620
Pro Thr Ala Tyr Gln Lys Gln Pro Ile Thr Arg Leu Ala Leu Pro Tyr
625                 630                 635                 640
Thr Ala Pro His Arg Val Leu Ala Thr Val Tyr Asn Gly Lys Thr Thr
                645                 650                 655
```

```
Tyr Gly Glu Thr Pro Ser Arg Arg Gly Asp Met Ala Ala Leu Ala Gln
            660                 665                 670

Arg Leu Ser Glu Arg Leu Pro Thr Ser Phe Asn Tyr Gly Ala Val Lys
        675                 680                 685

Ala Glu Thr Ile Thr Glu Leu Leu Ile Arg Met Lys Arg Ala Glu Thr
    690                 695                 700

<210> SEQ ID NO 21
<211> LENGTH: 2157
<212> TYPE: DNA
<213> ORGANISM: Artificial Sequence
<220> FEATURE:
<223> OTHER INFORMATION: nucleic acid, consensus vp1-4 Subtype C

<400> SEQUENCE: 21
atgctgaacg agggctggaa ggccagcgtg cagcgcaagc tgaagggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc     180 ggcagcaacg agggcagcac cgacaccacc agcacccaca ccaccaacac ccagaacaac     240
gactggttca gcaagctggc cagcagcgcc ttcagcggcc tgttcggcgc cctgctggcc     300
gacaagaaga ccgaggagac caccctgctg gaggaccgca tcctgaccac ccgcaacggc     360
cacaccacca gcaccaccca gagcagcgtg ggcgtgacct tcggctacgc caccgccgag     420
gacagcacca gcggccccaa caccagcggc ctggagaccc gcgtgcacca ggccgagcgc     480
ttcttcaaga tggccctgtt cgactgggtg cccagccaga acttcggcca catgcacaag     540
gtggtgctgc ccacgagcc caagggcgtg tacgccggcc tggtgaagag ctacgcctac     600
atgcgcaacg gctgggacgt ggaggtgacc gccgtgggca ccagttcaa cggcggctgc     660 ctgctggtgg ccctggtgcc cgagatgggc gacatcagcg accgcgagaa gtaccagctg     720
accctgtacc ccaccagtt catcaacccc cgcaccaaca tgaccgccca catcaccgtg     780
ccctacgtgg gcgtgaaccg ctacgaccag tacaagcagc accgcccctg gaccctggtg     840
gtgatggtgg tggcccccct gaccaccaac accgccggcg cccagcagat caaggtgtac     900
gccaacatcg ccccaccaa cgtgcacgtg gccggcgagc tgcccagcaa ggagggcatc     960
ttccccgtgg cctgcagcga cggctacggc aacatggtga ccaccgaccc caagaccgcc    1020
gaccccgtgt acggcaaggt gtacaacccc cccgcaccg cctgcccgg ccgcttcacc    1080 aactacctgg acgtggccga ggcctgcccc accttcctga tgttcgagaa cgtgccctac    1140
gtgagcaccc gcaccgacgg ccagcgcctg ctggccaagt cgacgtgag cctgccgcc    1200 aagcacatga gcaacaccta cctggccggc ctggcccagt actacacccca gtacaccggc    1260 accatcaacc tgcacttcat gttcaccggc cccaccgacg ccaaggcccg ctacatggtg    1320
gcctacgtgc cccccggcat ggacgccccc gacaacccccg aggaggccgc ccactgcatc    1380
cacgccgagt gggacaccgg cctgaacagc aagttcacct tcagcatccc ctacatcagc    1440
gccgccgact acgcctacac cgccagccac aaggccgaga ccacctgcgt gcagggctgg    1500
gtgtgcgtgt accagatcac ccacggcaag gccgacgccg acgccctggt ggtgagcgcc    1560
agcgccggca aggacttcga gctgcgcctg cccgtgacg cccgcaagca gaccaccacc    1620
accggcgaga gcgccgaccc cgtgaccacc accgtggaga actacggcgg cgagaccca    1680 gtgcagcgcc gccaccacac cgacgtggcc ttcgtgctgg accgcttcgt ggaggtgacc    1740
gtgagcggcc gcaaccagca caccctggac gtgatgcagg cccacaagga caacatcgtg    1800
```

-continued

```
ggcgccctgc tgcgcgccgc cacctactac ttcagcgacc tggagatcgc cgtgacccac    1860
accggcaagc tgacctgggt gcccaacggc gcccccgtga gcgccctgaa caacaccacc    1920
aaccccaccg cctaccacaa gggccccgtg accgcctgg ccctgcccta caccgccccc    1980
caccgcgtgc tggccaccgc ctacaccggc accaccacct acaccgccag cgcccgcggc    2040
gacctggccc acctgaccac cacccacgcc cgccacctgc ccaccagctt caacttcggc    2100
gccgtgaagg ccgagaccat caccgagctg ctggtgcgca tgaagcgcgc cgagctg      2157
```

<210> SEQ ID NO 22
<211> LENGTH: 719
<212> TYPE: PRT
<213> ORGANISM: Artificial Sequence
<220> FEATURE:
<223> OTHER INFORMATION: Consensus vp1-4 Subtype C

<400> SEQUENCE: 22

```
Met Leu Asn Glu Gly Trp Lys Ala Ser Val Gln Arg Lys Leu Lys Gly
1               5                   10                  15

```
Pro Thr Asn Val His Val Ala Gly Glu Leu Pro Ser Lys Glu Gly Ile
305                 310                 315                 320

Phe Pro Val Ala Cys Ser Asp Gly Tyr Gly Asn Met Val Thr Thr Asp
            325                 330                 335

Pro Lys Thr Ala Asp Pro Val Tyr Gly Lys Val Tyr Asn Pro Pro Arg
        340                 345                 350

Thr Ala Leu Pro Gly Arg Phe Thr Asn Tyr Leu Asp Val Ala Glu Ala
    355                 360                 365

Cys Pro Thr Phe Leu Met Phe Glu Asn Val Pro Tyr Val Ser Thr Arg
    370                 375                 380

Thr Asp Gly Gln Arg Leu Leu Ala Lys Phe Asp Val Ser Leu Ala Ala
385                 390                 395                 400

Lys His Met Ser Asn Thr Tyr Leu Ala Gly Leu Ala Gln Tyr Tyr Thr
            405                 410                 415

Gln Tyr Thr Gly Thr Ile Asn Leu His Phe Met Phe Thr Gly Pro Thr
        420                 425                 430

Asp Ala Lys Ala Arg Tyr Met Val Ala Tyr Val Pro Pro Gly Met Asp
    435                 440                 445

Ala Pro Asp Asn Pro Glu Glu Ala Ala His Cys Ile His Ala Glu Trp
450                 455                 460

Asp Thr Gly Leu Asn Ser Lys Phe Thr Phe Ser Ile Pro Tyr Ile Ser
465                 470                 475                 480

Ala Ala Asp Tyr Ala Tyr Thr Ala Ser His Lys Ala Glu Thr Thr Cys
            485                 490                 495

Val Gln Gly Trp Val Cys Val Tyr Gln Ile Thr His Gly Lys Ala Asp
        500                 505                 510

Ala Asp Ala Leu Val Val Ser Ala Ser Ala Gly Lys Asp Phe Glu Leu
    515                 520                 525

Arg Leu Pro Val Asp Ala Arg Lys Gln Thr Thr Thr Gly Glu Ser
530                 535                 540

Ala Asp Pro Val Thr Thr Thr Val Glu Asn Tyr Gly Gly Glu Thr Gln
545                 550                 555                 560

Val Gln Arg Arg His His Thr Asp Val Ala Phe Val Leu Asp Arg Phe
            565                 570                 575

Val Glu Val Thr Val Ser Gly Arg Asn Gln His Thr Leu Asp Val Met
        580                 585                 590

Gln Ala His Lys Asp Asn Ile Val Gly Ala Leu Leu Arg Ala Ala Thr
    595                 600                 605

Tyr Tyr Phe Ser Asp Leu Glu Ile Ala Val Thr His Thr Gly Lys Leu
    610                 615                 620

Thr Trp Val Pro Asn Gly Ala Pro Val Ser Ala Leu Asn Asn Thr Thr
625                 630                 635                 640

Asn Pro Thr Ala Tyr His Lys Gly Pro Val Thr Arg Leu Ala Leu Pro
            645                 650                 655

Tyr Thr Ala Pro His Arg Val Leu Ala Thr Ala Tyr Thr Gly Thr Thr
        660                 665                 670

Thr Tyr Thr Ala Ser Ala Arg Gly Asp Leu Ala His Leu Thr Thr Thr
    675                 680                 685

His Ala Arg His Leu Pro Thr Ser Phe Asn Phe Gly Ala Val Lys Ala
    690                 695                 700

Glu Thr Ile Thr Glu Leu Leu Val Arg Met Lys Arg Ala Glu Leu
705                 710                 715
```

<210> SEQ ID NO 23
<211> LENGTH: 2169
<212> TYPE: DNA
<213> ORGANISM: Artificial Sequence
<220> FEATURE:
<223> OTHER INFORMATION: nucleic acid, consensus vp1-4 Subtype O

<400> SEQUENCE: 23

| | | | | | |
|---|---|---|---|---|---|
| atgctgaacg | gcgagtggaa | ggccaaggtg | cagaagcgcc | tgcgcggcgc | cggccagagc | 60 |
| agccccgcca | ccggcagcca | gaaccagagc | ggcaacaccg | gcagcatcat | caacaactac | 120 |
| tacatgcagc | agtaccagaa | cagcatggac | acccagctgg | gcgacaacgc | catcagcggc | 180 |
| ggcagcaacg | agggcagcac | cgacaccacc | agcacccaca | ccaccaacac | ccagaacaac | 240 |
| gactggttca | gcaagctggc | cagcagcgcc | ttcagcggcc | tgttcggcgc | cctgctggcc | 300 |
| gacaagaaga | ccgaggagac | caccctgctg | gaggaccgca | tcctgaccac | ccgcaacggc | 360 |
| cacaccacca | gcaccaccca | gagcagcgtg | ggcgtgacct | acggctacgc | caccgccgag | 420 |
| gacttcgtga | gcggccccaa | caccagcggc | ctggagaccc | gcgtggtgca | ggccgagcgc | 480 |
| ttcttcaaga | cccacctgtt | cgactgggtg | accagcgacc | ccttcggccg | ctgctacctg | 540 |
| ctggagctgc | ccaccgacca | aagggcgtg | tacggcagcc | tgaccgacag | ctacgcctac | 600 |
| atgcgcaacg | gctgggacgt | ggaggtgacc | gccgtgggca | accagttcaa | cggcggctgc | 660 |
| ctgctggtgg | ccatggtgcc | cgagctgtgc | agcatcgaca | agcgcgagct | gtaccagctg | 720 |
| accctgttcc | cccaccagtt | catcaacccc | cgcaccaaca | tgaccgccca | catcaccgtg | 780 |
| cccttcgtgg | gcgtgaaccg | ctacgaccag | tacaaggtgc | acaagccctg | gaccctggtg | 840 |
| gtgatggtgg | tggccccct | accgtgaac | accgagggcg | cccccagat | caaggtgtac | 900 |
| gccaacatcg | cccccaccaa | cgtgcacgtg | gccggcgagt | tccccagcaa | ggagggcatc | 960 |
| ttccccgtgg | cctgcagcga | cggctacggc | ggcctggtga | ccaccgaccc | caagaccgcc | 1020 |
| gaccccgcct | acggcaaggt | gttcaacccc | cccgcaaca | tgctgccgg | ccgcttcacc | 1080 |
| aacttcctgg | acgtggccga | ggcctgcccc | accttcctgc | acttcgaggg | cggcgtgccc | 1140 |
| tacgtgacca | ccaagaccga | cagcgaccgc | gtgctggccc | agttcgacct | gagcctggcc | 1200 |
| gccaagcaca | tgagcaacac | cttcctggcc | ggcctggccc | agtactacac | ccagtacagc | 1260 |
| ggcaccatca | acctgcactt | catgttcacc | ggccccaccg | acgccaaggc | ccgctacatg | 1320 |
| atcgcctacg | ccccccccgg | catggagccc | cccaagaccc | ccgaggccgc | cgcccactgc | 1380 |
| atccacgccg | agtgggacac | cggcctgaac | agcaagttca | ccttcagcat | cccctacctg | 1440 |
| agcgccgcca | actacgccta | caccgccagc | gacgccgccg | agaccaccaa | cgtgcagggc | 1500 |
| tgggtgtgcc | tgttccagat | cacccacggc | aaggccgacg | gcgacgccct | ggtggtgctg | 1560 |
| gccagcgccg | gcaaggactt | cgagctgcgc | ctgcccgtgg | acgcccgcac | ccagaccacc | 1620 |
| agcgccggcg | agagcgccga | cccccgtgacc | gccaccgtgg | agaactacgg | cggcgagacc | 1680 |
| caggtgcagc | gccgccagca | caccgacgtg | agcttcatcc | tggaccgctt | cgtgaaggtg | 1740 |
| acccccaagg | accagatcaa | cgtgctggac | ctgatgcaga | ccccgccca | caccctggtg | 1800 |
| ggcgccctgc | tgcgcaccgc | cacctactac | ttcgccgacc | tggaggtggc | cgtgaagcac | 1860 |
| gagggcaacc | tgacctgggt | gcccaacggc | gcccccgaga | ccgccctgga | caacaccacc | 1920 |
| aaccccaccg | cctaccacaa | ggccccctg | accgcctgg | ccctgcccta | caccgccccc | 1980 |
| caccgcgtgc | tggccaccgt | gtacaacggc | aactgcaagt | acggcgagag | ccccgtgacc | 2040 |
| aacgtgcgcg | gcgacctgca | ggtgctggcc | cagaaggccg | cccgcacccct | gcccaccagc | 2100 | ttcaactacg gcgccatcaa ggccacccgc gtgaccgagc tgctgtaccg catgaagcgc 2160 gccgagacc 2169

<210> SEQ ID NO 24
<211> LENGTH: 723
<212> TYPE: PRT
<213> ORGANISM: Artificial Sequence
<220> FEATURE:
<223> OTHER INFORMATION: Consensus vp1-4 Subtype O

<400> SEQUENCE: 24

Met Leu Asn Gly Glu Trp Lys Ala Lys Val Gln Lys Arg Leu Arg Gly
1 5 10 15

Ala Gly Gln Ser Ser Pro Ala Thr Gly Ser Gln Asn Gln Ser Gly Asn
20 25 30

Thr Gly Ser Ile Ile Asn Asn Tyr Tyr Met Gln Gln Tyr Gln Asn Ser
35 40 45

Met Asp Thr Gln Leu Gly Asp Asn Ala Ile Ser Gly Gly Ser Asn Glu
50 55 60

Gly Ser Thr Asp Thr Thr Ser Thr His Thr Thr Asn Thr Gln Asn Asn
65 70 75 80

Asp Trp Phe Ser Lys Leu Ala Ser Ser Ala Phe Ser Gly Leu Phe Gly
85 90 95

Ala Leu Leu Ala Asp Lys Lys Thr Glu Glu Thr Thr Leu Leu Glu Asp
100 105 110

Arg Ile Leu Thr Thr Arg Asn Gly His Thr Thr Ser Thr Thr Gln Ser
115 120 125

Ser Val Gly Val Thr Tyr Gly Tyr Ala Thr Ala Glu Asp Phe Val Ser
130 135 140

Gly Pro Asn Thr Ser Gly Leu Glu Thr Arg Val Val Gln Ala Glu Arg
145 150 155 160

Phe Phe Lys Thr His Leu Phe Asp Trp Val Thr Ser Asp Pro Phe Gly
165 170 175

Arg Cys Tyr Leu Leu Glu Leu Pro Thr Asp His Lys Gly Val Tyr Gly
180 185 190

Ser Leu Thr Asp Ser Tyr Ala Tyr Met Arg Asn Gly Trp Asp Val Glu
195 200 205

Val Thr Ala Val Gly Asn Gln Phe Asn Gly Gly Cys Leu Leu Val Ala
210 215 220

Met Val Pro Glu Leu Cys Ser Ile Asp Lys Arg Glu Leu Tyr Gln Leu
225 230 235 240

Thr Leu Phe Pro His Gln Phe Ile Asn Pro Arg Thr Asn Met Thr Ala
245 250 255

His Ile Thr Val Pro Phe Val Gly Val Asn Arg Tyr Asp Gln Tyr Lys
260 265 270

Val His Lys Pro Trp Thr Leu Val Val Met Val Val Ala Pro Leu Thr
275 280 285

Val Asn Thr Glu Gly Ala Pro Gln Ile Lys Val Tyr Ala Asn Ile Ala
290 295 300

Pro Thr Asn Val His Val Ala Gly Glu Phe Pro Ser Lys Glu Gly Ile
305 310 315 320

Phe Pro Val Ala Cys Ser Asp Gly Tyr Gly Gly Leu Val Thr Thr Asp
325 330 335

Pro Lys Thr Ala Asp Pro Ala Tyr Gly Lys Val Phe Asn Pro Pro Arg
340 345 350

Asn Met Leu Pro Gly Arg Phe Thr Asn Phe Leu Asp Val Ala Glu Ala
        355                 360                 365

Cys Pro Thr Phe Leu His Phe Glu Gly Gly Val Pro Tyr Val Thr Thr
370                 375                 380

Lys Thr Asp Ser Asp Arg Val Leu Ala Gln Phe Asp Leu Ser Leu Ala
385                 390                 395                 400

Ala Lys His Met Ser Asn Thr Phe Leu Ala Gly Leu Ala Gln Tyr Tyr
                405                 410                 415

Thr Gln Tyr Ser Gly Thr Ile Asn Leu His Phe Met Phe Thr Gly Pro
            420                 425                 430

Thr Asp Ala Lys Ala Arg Tyr Met Ile Ala Tyr Ala Pro Pro Gly Met
            435                 440                 445

Glu Pro Pro Lys Thr Pro Glu Ala Ala Ala His Cys Ile His Ala Glu
        450                 455                 460

Trp Asp Thr Gly Leu Asn Ser Lys Phe Thr Phe Ser Ile Pro Tyr Leu
465                 470                 475                 480

Ser Ala Ala Asp Tyr Ala Tyr Thr Ala Ser Asp Ala Ala Glu Thr Thr
                485                 490                 495

Asn Val Gln Gly Trp Val Cys Leu Phe Gln Ile Thr His Gly Lys Ala
            500                 505                 510

Asp Gly Asp Ala Leu Val Val Leu Ala Ser Ala Gly Lys Asp Phe Glu
        515                 520                 525

Leu Arg Leu Pro Val Asp Ala Arg Thr Gln Thr Thr Ser Ala Gly Glu
530                 535                 540

Ser Ala Asp Pro Val Thr Ala Thr Val Glu Asn Tyr Gly Gly Glu Thr
545                 550                 555                 560

Gln Val Gln Arg Arg Gln His Thr Asp Val Ser Phe Ile Leu Asp Arg
                565                 570                 575

Phe Val Lys Val Thr Pro Lys Asp Gln Ile Asn Val Leu Asp Leu Met
            580                 585                 590

Gln Thr Pro Ala His Thr Leu Val Gly Ala Leu Leu Arg Thr Ala Thr
        595                 600                 605

Tyr Tyr Phe Ala Asp Leu Glu Val Ala Val Lys His Glu Gly Asn Leu
610                 615                 620

Thr Trp Val Pro Asn Gly Ala Pro Glu Thr Ala Leu Asp Asn Thr Thr
625                 630                 635                 640

Asn Pro Thr Ala Tyr His Lys Ala Pro Leu Thr Arg Leu Ala Leu Pro
                645                 650                 655

Tyr Thr Ala Pro His Arg Val Leu Ala Thr Val Tyr Asn Gly Asn Cys
            660                 665                 670

Lys Tyr Gly Glu Ser Pro Val Thr Asn Val Arg Gly Asp Leu Gln Val
        675                 680                 685

Leu Ala Gln Lys Ala Ala Arg Thr Leu Pro Thr Ser Phe Asn Tyr Gly
690                 695                 700

Ala Ile Lys Ala Thr Arg Val Thr Glu Leu Leu Tyr Arg Met Lys Arg
705                 710                 715                 720

Ala Glu Thr

<210> SEQ ID NO 25
<211> LENGTH: 2196
<212> TYPE: DNA
<213> ORGANISM: Artificial Sequence
<220> FEATURE:
<223> OTHER INFORMATION: nucleic acid, Consensus vp1-4 Subtype SAT1

<400> SEQUENCE: 25

```
atgctggacg tggactggca ggaccgcgcc ggcctgttcc tgcgcggcgc cggccagagc      60
agccccgcca ccggcagcca gaaccagagc ggcaacaccg gcagcatcat caacaactac     120
tacatgcagc agtaccagaa cagcatggac acccagctgg cgacaacgc catcagcggc      180
ggcagcaacg agggcagcac cgacaccacc agcacccaca ccaacaacac ccagaacaac     240
gactggttca gcaagctggc ccagagcgcc ttcagcggcc tggtgggcgc cctgctggcc     300
gacaagaaga ccgaggagac caccctgctg gaggaccgca tcatgaccac cagccacggc     360
accaccacca gcaccaccca gagcagcgtg ggcgtgacct acggctacgc cctggccgac     420
aagttcctgc ccggccccaa caccaacggc ctggagaccc gcgtggagca ggccgagcgc     480
ttcttcaagc acaagctgtt cgactggacc accgaccagc agttcggcac cacccacgtg     540
ctggagctgc ccaccgacca agggcatc tacggccagc tggtggacag ccacgcctac       600
atccgcaacg ctgggacgt gcaggtgagc gccaccgcca cccagttcaa cggcggctgc      660
ctgctggtgg ccatggtgcc cgagctgtgc aagctggacg accgcgagaa gtaccagctg     720
accctgttcc cccaccagtt cctgaacccc gcaccaaca ccaccgccca catccaggtg      780
ccctacctgg gcgtggaccg ccacgaccag ggcacccgcc acaaggcctg gaccctggtg     840
gtgatggtgg tggcccccta caccaacgac cagaccatcg gcagcaccaa ggccgaggtg     900
tacgtgaaca tcgcccccac caacgtgtac gtggccggcg agaagcccgc caagcagggc     960
atcctgcccg tggccgtgag cgacggctac ggcggcttcc agaacaccga ccccaagacc    1020
agcgacccca tctacggcca cgtgtacaac cccgcccgca ccctgtaccc cggccgcttc    1080
accaacctgc tggacgtggc cgaggcctgc cccacccgc tggacttcaa cggcgtgccc     1140
tacgtgcaga cccagaacaa cagcggcagc aaggtgctgg cccgcttcga cctggccttc    1200
ggccacaaga acatgaagaa cacctacatg agcggcctgg cccagtactt cgcccagtac    1260
agcggcaccc tgaacctgca cttcatgtac accggcccca ccaacaacaa ggccaagtac    1320
atggtggcct acatcccccc cggcacccac cccctgcccg agaccccga gatggccagc    1380
cactgctacc acgccgagtg ggacaccggc ctgaacagca ccttcacctt caccgtgccc    1440
tacatcagcg ccgccgacta cgcctacacc tacgccgacg agcccgagca ggccagcgtg    1500
cagggctggg tgggcgtgta ccagatcacc gacacccacg agaaggacgg cgccgtgatc    1560
gtgaccgtga gcgccggccc cgacttcgag ttccgcatgc ccatcagccc cagccgccag    1620
accaccagcg ccggcgaggg cgccgacccc gtgaccaccg acgtgagcga gcacggcggc    1680
gacagccgca ccgcccgccg cgcccacacc gacgtggcct cctgctgga ccgcttcacc     1740
ctggtgggca agaccaggga caacaagctg gtgctggacc tgctgaccac caaggagaag    1800
agcctggtgg gcgccctgct gcgcgccgcc acctactact tcagcgacct ggaggtggcc    1860
tgcgtgggca ccaacaagtg ggtgggctgg accccaacg cagccccgt gaagctgagc      1920
gaggtgggcg acaaccccgt ggtgttcagc cacaacggca ccaccgctt cgccctgccc     1980
tacaccgccc ccaccgcgt gctggccacc gtgtacaacg cgactgcaa gtacaagccc      2040
accggcaccc ccccgcga aacatccgc ggcgacctgg ccaccctggc cgcccgcatc      2100
gccagcgaga cccacatccc caccaccttc aactacggca tgatctacac cgaggccgag    2160
gtggacgtgt acctgcgcat gaagcgcgcc gagctg                               2196
```

<210> SEQ ID NO 26

<211> LENGTH: 732
<212> TYPE: PRT
<213> ORGANISM: Artificial Sequence
<220> FEATURE:
<223> OTHER INFORMATION: Consensus vp1-4 Subtype SAT1

<400> SEQUENCE: 26

```
Met Leu Asp Val Asp Trp Gln Asp Arg Ala Gly Leu Phe Leu Arg Gly
 1               5                  10                  15
Ala Gly Gln Ser Ser Pro Ala Thr Gly Ser Gln Asn Gln Ser Gly Asn
                20                  25                  30
Thr Gly Ser Ile Ile Asn Asn Tyr Tyr Met Gln Gln Tyr Gln Asn Ser
            35                  40                  45
Met Asp Thr Gln Leu Gly Asp Asn Ala Ile Ser Gly Gly Ser Asn Glu
 50                  55                  60
Gly Ser Thr Asp Thr Thr Ser Thr His Thr Asn Asn Thr Gln Asn Asn
 65                  70                  75                  80
Asp Trp Phe Ser Lys Leu Ala Gln Ser Ala Phe Ser Gly Leu Val Gly
                85                  90                  95
Ala Leu Leu Ala Asp Lys Lys Thr Glu Glu Thr Thr Leu Leu Glu Asp
            100                 105                 110
Arg Ile Met Thr Thr Ser His Gly Thr Thr Thr Ser Thr Thr Gln Ser
            115                 120                 125
Ser Val Gly Val Thr Tyr Gly Tyr Ala Leu Ala Asp Lys Phe Leu Pro
130                 135                 140
Gly Pro Asn Thr Asn Gly Leu Glu Thr Arg Val Glu Gln Ala Glu Arg
145                 150                 155                 160
Phe Phe Lys His Lys Leu Phe Asp Trp Thr Thr Asp Gln Gln Phe Gly
                165                 170                 175
Thr Thr His Val Leu Glu Leu Pro Thr Asp His Lys Gly Ile Tyr Gly
            180                 185                 190
Gln Leu Val Asp Ser His Ala Tyr Ile Arg Asn Gly Trp Asp Val Gln
            195                 200                 205
Val Ser Ala Thr Ala Thr Gln Phe Asn Gly Gly Cys Leu Leu Val Ala
210                 215                 220
Met Val Pro Glu Leu Cys Lys Leu Asp Asp Arg Glu Lys Tyr Gln Leu
225                 230                 235                 240
Thr Leu Phe Pro His Gln Phe Leu Asn Pro Arg Thr Asn Thr Thr Ala
                245                 250                 255
His Ile Gln Val Pro Tyr Leu Gly Val Asp Arg His Asp Gln Gly Thr
            260                 265                 270
Arg His Lys Ala Trp Thr Leu Val Val Met Val Val Ala Pro Tyr Thr
            275                 280                 285
Asn Asp Gln Thr Ile Gly Ser Thr Lys Ala Glu Val Tyr Val Asn Ile
290                 295                 300
Ala Pro Thr Asn Val Tyr Val Ala Gly Glu Lys Pro Ala Lys Gln Gly
305                 310                 315                 320
Ile Leu Pro Val Ala Val Ser Asp Gly Tyr Gly Gly Phe Gln Asn Thr
                325                 330                 335
Asp Pro Lys Thr Ser Asp Pro Ile Tyr Gly His Val Tyr Asn Pro Ala
            340                 345                 350
Arg Thr Leu Tyr Pro Gly Arg Phe Thr Asn Leu Leu Asp Val Ala Glu
            355                 360                 365
Ala Cys Pro Thr Leu Leu Asp Phe Asn Gly Val Pro Tyr Val Gln Thr
370                 375                 380
```

Gln Asn Asn Ser Gly Ser Lys Val Leu Ala Arg Phe Asp Leu Ala Phe
385                 390                 395                 400

Gly His Lys Asn Met Lys Asn Thr Tyr Met Ser Gly Leu Ala Gln Tyr
            405                 410                 415

Phe Ala Gln Tyr Ser Gly Thr Leu Asn Leu His Phe Met Tyr Thr Gly
            420                 425                 430

Pro Thr Asn Asn Lys Ala Lys Tyr Met Val Ala Tyr Ile Pro Pro Gly
            435                 440                 445

Thr His Pro Leu Pro Glu Thr Pro Glu Met Ala Ser His Cys Tyr His
            450                 455                 460

Ala Glu Trp Asp Thr Gly Leu Asn Ser Thr Phe Thr Phe Thr Val Pro
465                 470                 475                 480

Tyr Ile Ser Ala Ala Asp Tyr Ala Tyr Thr Tyr Ala Asp Glu Pro Glu
            485                 490                 495

Gln Ala Ser Val Gln Gly Trp Val Gly Val Tyr Gln Ile Thr Asp Thr
            500                 505                 510

His Glu Lys Asp Gly Ala Val Ile Val Thr Val Ser Ala Gly Pro Asp
            515                 520                 525

Phe Glu Phe Arg Met Pro Ile Ser Pro Ser Arg Gln Thr Thr Ser Ala
530                 535                 540

Gly Glu Gly Ala Asp Pro Val Thr Thr Asp Val Ser Glu His Gly Gly
545                 550                 555                 560

Asp Ser Arg Thr Ala Arg Arg Ala His Thr Asp Val Ala Phe Leu Leu
            565                 570                 575

Asp Arg Phe Thr Leu Val Gly Lys Thr Gln Asp Asn Lys Leu Val Leu
            580                 585                 590

Asp Leu Leu Thr Thr Lys Glu Lys Ser Leu Val Gly Ala Leu Leu Arg
            595                 600                 605

Ala Ala Thr Tyr Tyr Phe Ser Asp Leu Glu Val Ala Cys Val Gly Thr
610                 615                 620

Asn Lys Trp Val Gly Trp Thr Pro Asn Gly Ser Pro Val Lys Leu Ser
625                 630                 635                 640

Glu Val Gly Asp Asn Pro Val Val Phe Ser His Asn Gly Thr Thr Arg
            645                 650                 655

Phe Ala Leu Pro Tyr Thr Ala Pro His Arg Val Leu Ala Thr Val Tyr
            660                 665                 670

Asn Gly Asp Cys Lys Tyr Lys Pro Thr Gly Thr Pro Arg Glu Asn
            675                 680                 685

Ile Arg Gly Asp Leu Ala Thr Leu Ala Ala Arg Ile Ala Ser Glu Thr
            690                 695                 700

His Ile Pro Thr Thr Phe Asn Tyr Gly Met Ile Tyr Thr Glu Ala Glu
705                 710                 715                 720

Val Asp Val Tyr Leu Arg Met Lys Arg Ala Glu Leu
            725                 730

<210> SEQ ID NO 27
<211> LENGTH: 2184
<212> TYPE: DNA
<213> ORGANISM: Artificial Sequence
<220> FEATURE:
<223> OTHER INFORMATION: nucleic acid, Consensus vp1-4 Subtype SAT2

<400> SEQUENCE: 27
atgctggacg tggactggca ggacaaggcc ggcctgttcc tgcgcggcgc cggccagagc    60

| | |
|---|---|
| agccccgcca ccggcagcca gaaccagagc ggcaacaccg gcagcatcat caacaactac | 120 |
| tacatgcagc agtaccagaa cagcatggac acccagctgg gcgacaacgc catcagcggc | 180 |
| ggcagcaacg agggcagcac cgacaccacc agcacccaca ccaacaacac ccagaacaac | 240 |
| gactggttca gcaagctggc ccagagcgcc atcagcggcc tgttcggcgc cctgctggcc | 300 |
| gacaagaaga ccgaggagac caccctgctg gaggaccgca tcctgaccac ccgccacggc | 360 |
| accaccacca gcaccaccca gagcagcgtg ggcatcacct acggctacgc cgacgccgac | 420 |
| agcttccgcc ccggccccaa caccagcggc ctggagaccc gcgtggagca ggccgagcgc | 480 |
| ttcttcaagg agaagctgtt cgactggacc agcgacaagc ccttcggcac cctgtacgtg | 540 |
| ctggagctgc ccaaggacca aagggcatc tacggcagcc tgaccgacgc ctacacctac | 600 |
| atgcgcaacg gctgggacgt gcaggtgagc gccaccagca cccagttcaa cggcggcagc | 660 |
| ctgctggtgg ccatggtgcc cgagctgtgc agcctgaagg accgcgagga gttccagctg | 720 |
| accctgtacc cccaccagtt catcaacccc cgcaccaaca ccaccgccca catccaggtg | 780 |
| ccctacctgg gcgtgaaccg ccacgaccag ggcaagcgcc accaggcctg gagcctggtg | 840 |
| gtgatggtgc tgacccccct gaccaccgag gcccagatga acagcggcac cgtggaggtg | 900 |
| tacgccaaca tcgcccccac caacgtgttc gtggccggcg agaagcccgc caagcagggc | 960 |
| atcatccccg tggcctgcgc cgacggctac ggcggcttcc agaacaccga ccccaagacc | 1020 |
| gccgacccca tctacggcta cgtgtacaac cccagccgca acgactgcca cggccgctac | 1080 |
| agcaacctgc tggacgtggc cgaggcctgc cccaccctgc tgaacttcga cggcaagccc | 1140 |
| tacgtggtga ccaagaacaa cggcgacaag gtgatggccg ccttcgacgt ggccttcacc | 1200 |
| cacaaggtgc acaagaacac cttcctggcc ggcctggccg actactacac ccagtaccag | 1260 |
| ggcagcctga ctaccactt catgtacacc ggccccaccc accacaaggc caagttcatg | 1320 |
| gtggcctaca tccccccgg catcgagacc gacaagctgc ccaagacccc cgaggacgcc | 1380 |
| gcccactgct accacagcga gtgggacacc ggcctgaaca gccagttcac cttcgccgtg | 1440 |
| ccctacgtga gcgccagcga cttcagctac acccacaccg acacccccgc catggccacc | 1500 |
| accaacggct gggtggccgt gttccaggtg accgacaccc acagcgccga ggccgccgtg | 1560 |
| gtggtgagcg tgagcgccgg ccccgacctg gagttccgct tccccatcga ccccgtgcgc | 1620 |
| cagaccacca cgccggcga gggcgccgag gtggtgacca ccgaccccag caccacggc | 1680 |
| ggcaaggtga ccgagaagcg ccgcgtgcac accgacgtgg ccttcgtgct ggaccgcttc | 1740 |
| acccacgtgc acaccaacaa gaccaccttc gccgtggacc tgatggacac caaggagaag | 1800 |
| accctggtgg gcgccctgct gcgcgccgcc acctactact ctgcgacct ggagatcgcc | 1860 |
| tgcgtgggcg agcacaagcg cgtgttctgg cagcccaacg gcgccccccg caccacccag | 1920 |
| ctgggcgaca ccccatggt gttcagccac aacaaggtga cccgcttcgc catcccctac | 1980 |
| accgccccc accgcctgct gagcaccgtg tacaacggcg agtgcgagta caccaagacc | 2040 |
| gtgaccgcca tccgcggcga ccgcgaggtg ctggccgcca gtacagcag cgccaagcac | 2100 |
| accctgccca gcaccttcaa cttcggcttc gtgaccgccg acgagcccgt ggacgtgtac | 2160 |
| taccgcatga agcgcgccga gctg | 2184 |

<210> SEQ ID NO 28
<211> LENGTH: 728
<212> TYPE: PRT
<213> ORGANISM: Artificial Sequence
<220> FEATURE:
<223> OTHER INFORMATION: Consensus vp1-4 Subtype SAT2

<400> SEQUENCE: 28

Met Leu Asp Val Asp Trp Gln Asp Lys Ala Gly Leu Phe Leu Arg Gly
1               5                   10                  15

Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
        35                  40                  45

Met Asp Thr Gln Leu Gly Asp Asn Ala Ile Ser Gly Gly Ser Asn Glu
50                  55                  60

Gly Ser Thr Asp Thr Thr Ser Thr His Thr Asn Asn Thr Gln Asn Asn
65                  70                  75                  80

Asp Trp Phe Ser Lys Leu Ala Gln Ser Ala Ile Ser Gly Leu Phe Gly
                85                  90                  95

Ala Leu Leu Ala Asp Lys Lys Thr Glu Glu Thr Thr Leu Leu Glu Asp
            100                 105                 110

Arg Ile Leu Thr Thr Arg His Gly Thr Thr Thr Ser Thr Thr Gln Ser
        115                 120                 125

Ser Val Gly Ile Thr Tyr Gly Tyr Ala Asp Ala Asp Ser Phe Arg Pro
    130                 135                 140

Gly Pro Asn Thr Ser Gly Leu Glu Thr Arg Val Glu Gln Ala Glu Arg
145                 150                 155                 160

Phe Phe Lys Glu Lys Leu Phe Asp Trp Thr Asp Lys Pro Phe Gly
                165                 170                 175

Thr Leu Tyr Val Leu Glu Leu Pro Lys Asp His Lys Gly Ile Tyr Gly
            180                 185                 190

Ser Leu Thr Asp Ala Tyr Thr Tyr Met Arg Asn Gly Trp Asp Val Gln
        195                 200                 205

Val Ser Ala Thr Ser Thr Gln Phe Asn Gly Gly Ser Leu Leu Val Ala
    210                 215                 220

Met Val Pro Glu Leu Cys Ser Leu Lys Asp Arg Glu Glu Phe Gln Leu
225                 230                 235                 240

Thr Leu Tyr Pro His Gln Phe Ile Asn Pro Arg Thr Asn Thr Thr Ala
            245                 250                 255

His Ile Gln Val Pro Tyr Leu Gly Val Asn Arg His Asp Gln Gly Lys
        260                 265                 270

Arg His Gln Ala Trp Ser Leu Val Met Val Leu Thr Pro Leu Thr
    275                 280                 285

Thr Glu Ala Gln Met Asn Ser Gly Thr Val Glu Val Tyr Ala Asn Ile
290                 295                 300

Ala Pro Thr Asn Val Phe Val Ala Gly Glu Lys Pro Ala Lys Gln Gly
305                 310                 315                 320

Ile Ile Pro Val Ala Cys Ala Asp Gly Tyr Gly Gly Phe Gln Asn Thr
            325                 330                 335

Asp Pro Lys Thr Ala Asp Pro Ile Tyr Gly Tyr Val Tyr Asn Pro Ser
        340                 345                 350

Arg Asn Asp Cys His Gly Arg Tyr Ser Asn Leu Leu Asp Val Ala Glu
    355                 360                 365

Ala Cys Pro Thr Leu Leu Asn Phe Asp Gly Lys Pro Tyr Val Val Thr
    370                 375                 380

Lys Asn Asn Gly Asp Lys Val Met Ala Ala Phe Asp Val Ala Phe Thr
385                 390                 395                 400

His Lys Val His Lys Asn Thr Phe Leu Ala Gly Leu Ala Asp Tyr Tyr

```
            405                 410                 415
Thr Gln Tyr Gln Gly Ser Leu Asn Tyr His Phe Met Tyr Thr Gly Pro
            420                 425                 430

Thr His His Lys Ala Lys Phe Met Val Ala Tyr Ile Pro Pro Gly Ile
            435                 440                 445

Glu Thr Asp Lys Leu Pro Lys Thr Pro Glu Asp Ala Ala His Cys Tyr
        450                 455                 460

His Ser Glu Trp Asp Thr Gly Leu Asn Ser Gln Phe Thr Phe Ala Val
465                 470                 475                 480

Pro Tyr Val Ser Ala Ser Asp Phe Ser Tyr Thr His Thr Asp Thr Pro
                485                 490                 495

Ala Met Ala Thr Thr Asn Gly Trp Val Ala Val Phe Gln Val Thr Asp
            500                 505                 510

Thr His Ser Ala Glu Ala Ala Val Val Ser Val Ser Ala Gly Pro
        515                 520                 525

Asp Leu Glu Phe Arg Phe Pro Ile Asp Pro Val Arg Gln Thr Thr Ser
530                 535                 540

Ala Gly Glu Gly Ala Glu Val Val Thr Thr Asp Pro Ser Thr His Gly
545                 550                 555                 560

Gly Lys Val Thr Glu Lys Arg Val His Thr Asp Val Ala Phe Val
                565                 570                 575

Leu Asp Arg Phe Thr His Val His Thr Asn Lys Thr Thr Phe Ala Val
            580                 585                 590

Asp Leu Met Asp Thr Lys Glu Lys Thr Leu Val Gly Ala Leu Leu Arg
            595                 600                 605

Ala Ala Thr Tyr Tyr Phe Cys Asp Leu Glu Ile Ala Cys Val Gly Glu
        610                 615                 620

His Lys Arg Val Phe Trp Gln Pro Asn Gly Ala Pro Arg Thr Thr Gln
625                 630                 635                 640

Leu Gly Asp Asn Pro Met Val Phe Ser His Asn Lys Val Thr Arg Phe
                645                 650                 655

Ala Ile Pro Tyr Thr Ala Pro His Arg Leu Leu Ser Thr Val Tyr Asn
            660                 665                 670

Gly Glu Cys Glu Tyr Thr Lys Thr Val Thr Ala Ile Arg Gly Asp Arg
        675                 680                 685

Glu Val Leu Ala Ala Lys Tyr Ser Ser Ala Lys His Thr Leu Pro Ser
        690                 695                 700

Thr Phe Asn Phe Gly Phe Val Thr Ala Asp Glu Pro Val Asp Val Tyr
705                 710                 715                 720

Tyr Arg Met Lys Arg Ala Glu Leu
                725
```

<210> SEQ ID NO 29
<211> LENGTH: 2181
<212> TYPE: DNA
<213> ORGANISM: Artificial Sequence
<220> FEATURE:
<223> OTHER INFORMATION: nucleic acid, Consensus vp1-4 Subtype SAT3

<400> SEQUENCE: 29

```
atgctggacg tggactggca ggaccgcgcc ggcctgttcc tgcgcggcgc cggccagagc    60
agccccgcca ccggcagcca gaaccagagc ggcaacaccg gcagcatcat caacaactac   120
tacatgcagc agtaccagaa cagcatggac acccagctgg cgacaacgc catcagcggc   180 ggcagcaacg agggcagcac cgacaccacc agcacccaca ccaacaacac ccagaacaac   240
```

```
gactggttca gcaagctggc ccagagcgcc atcagcggcc tgttcggcgc cctgctggcc      300
gacaagaaga ccgaggagac cacccacctg gaggaccgca tcctgaccac ccgccacaac      360
accaccacca gcaccaccca gagcagcgtg ggcgtgacct acggctacgt gagcgccgac      420
cgcttcctgc ccggccccaa caccagcggc ctggagagcc gcgtggagca ggccgagcgc      480
ttcttcaagg agaagctgtt cacctggacc gccagccagg agtacgccca cgtgcacctg      540
ctggagctgc ccaccgacca aggggcatc tacggcgcca tggtggacag ccacgcctac      600
gtgcgcaacg gctgggacgt gcaggtgacc gccaccagca cccagttcaa cggcggcacc      660
ctgctggtgg ccatggtgcc cgagctgcac agcctggaca cccgcgacgt gagccagctg      720
accctgttcc cccaccagtt catcaacccc gcaccaaca ccaccgccca catcgtggtg       780
ccctacgtgg gcgtgaaccg ccacgaccag gtgcagatgc acaaggcctg gaccctggtg      840
gtggccgtga tggcccccct gaccaccagc agcatgggcc aggacaacgt ggaggtgtac     900
gccaacatcg ccccccacca cgtgtacgtg gccggcgagc gccccagcaa gagggcatc     960
atccccgtgg cctgcaacga cggctacggc ggcttccaga caccgaccc caagaccgcc    1020
gaccccatct acggcctggt gagcaacccc cccgcaccg ccttccccgg ccgcttcacc     1080
aacctgctgg acgtggccga ggcctgcccc accttcctgg acttcgacgg cgtgccctac    1140
gtgaagacca cccacaacag cggcagcaag atcctgaccc catcgacct ggccttcggc     1200
cacaagagct tcaagaacac ctacctggcc ggcctggccc agtactacgc ccagtacagc    1260
ggcagcatca acctgcactt catgtacacc ggccccaccc agagcaaggc ccgcttcatg    1320
gtggcctaca tccccccgg caccaccgtg cccaacaccc ccgagcaggc cgcccactgc    1380
taccacagcg agtgggacac cggcctgaac agcaagttca ccttcaccgt gcccctacatg   1440
agcgccgccg acttcgccta cacctactgc gacgagcccg gcaggccag cgcccagggc    1500
tgggtgaccc tgtaccagat caccgacacc cacgaccccg acagcgccgt gctggtgagc    1560
gtgagcgccg gcgccgactt cgagctgcgc ctgcccatca ccccgccgc cagaccacc    1620
agcgccggcg agggcgccga cgtggtgacc accgacgtga ccaccacggg cggcgaggtg   1680
agcgtgcccc gccgccagca caccaacgtg gagttcctgc tggaccgctt cacccacatc    1740
ggcaccatca acgcccaccg caccatctgc ctgatggaca ccaaggagca cacctggtg    1800
ggcgccatcc tgcgcagcgc cacctactac ttctgcgacc tggaggtggc cgtgctgggc    1860
aacgccaagt acgccgcctg ggtgcccaac ggctgccccc acaccgaccg cgtggaggac   1920
aaccccgtgt gcacagcaa gggcagcgtg gtgcgcttcg ccctgcccta caccgccccc   1980
cacggcgtgc tggccaccgt gtacaacggc aactgcaagt acagcaccac ccagcgcgtg    2040
gccccccgcc gcggcgacct gggcgtgctg agccagcgcg tggagaacga gaccaccgc   2100
tgcatccccca ccaccttcaa cttcggccgc ctgctgtgcg agagcggcga cgtgtactac    2160
cgcatgaagc gcaccgagct g                                              2181
```

<210> SEQ ID NO 30
<211> LENGTH: 727
<212> TYPE: PRT
<213> ORGANISM: Artificial Sequence
<220> FEATURE:
<223> OTHER INFORMATION: Consensus vp1-4 Subtype SAT3

<400> SEQUENCE: 30

Met Leu Asp Val Asp Trp Gln Asp Arg Ala Gly Leu Phe Leu Arg Gly
1               5                   10                  15

```
Ala Gly Gln Ser Ser Pro Ala Thr Gly Ser Gln Asn Gln Ser Gly Asn
            20                  25                  30

Thr Gly Ser Ile Ile Asn Asn Tyr Tyr Met Gln Gln Tyr Gln Asn Ser
            35                  40                  45

Met Asp Thr Gln Leu Gly Asp Asn Ala Ile Ser Gly Gly Ser Asn Glu
 50                  55                  60

Gly Ser Thr Asp Thr Ser Thr His Thr Asn Asn Thr Gln Asn Asn
 65                  70                  75                  80

Asp Trp Phe Ser Lys Leu Ala Gln Ser Ala Ile Ser Gly Leu Phe Gly
                85                  90                  95

Ala Leu Leu Ala Asp Lys Lys Thr Glu Thr Thr His Leu Glu Asp
            100                 105                 110

Arg Ile Leu Thr Thr Arg His Asn Thr Thr Ser Thr Thr Gln Ser
            115                 120                 125

Ser Val Gly Val Thr Tyr Gly Tyr Val Ser Ala Asp Arg Phe Leu Pro
    130                 135                 140

Gly Pro Asn Thr Ser Gly Leu Glu Ser Arg Val Glu Gln Ala Glu Arg
145                 150                 155                 160

Phe Phe Lys Glu Lys Leu Phe Thr Trp Thr Ala Ser Gln Glu Tyr Ala
                165                 170                 175

His Val His Leu Leu Glu Leu Pro Thr Asp His Lys Gly Ile Tyr Gly
            180                 185                 190

Ala Met Val Asp Ser His Ala Tyr Val Arg Asn Gly Trp Asp Val Gln
            195                 200                 205

Val Thr Ala Thr Ser Thr Gln Phe Asn Gly Gly Thr Leu Leu Val Ala
    210                 215                 220

Met Val Pro Glu Leu His Ser Leu Asp Thr Arg Asp Val Ser Gln Leu
225                 230                 235                 240

Thr Leu Phe Pro His Gln Phe Ile Asn Pro Arg Thr Asn Thr Thr Ala
                245                 250                 255

His Ile Val Val Pro Tyr Val Gly Val Asn Arg His Asp Gln Val Gln
            260                 265                 270

Met His Lys Ala Trp Thr Leu Val Val Ala Val Met Ala Pro Leu Thr
            275                 280                 285

Thr Ser Ser Met Gly Gln Asp Asn Val Glu Val Tyr Ala Asn Ile Ala
    290                 295                 300

Pro Thr Asn Val Tyr Val Ala Gly Glu Arg Pro Ser Lys Gln Gly Ile
305                 310                 315                 320

Ile Pro Val Ala Cys Asn Asp Gly Tyr Gly Gly Phe Gln Asn Thr Asp
                325                 330                 335

Pro Lys Thr Ala Asp Pro Ile Tyr Gly Leu Val Ser Asn Pro Pro Arg
            340                 345                 350

Thr Ala Phe Pro Gly Arg Phe Thr Asn Leu Leu Asp Val Ala Glu Ala
            355                 360                 365

Cys Pro Thr Phe Leu Asp Phe Asp Gly Val Pro Tyr Val Lys Thr Thr
            370                 375                 380

His Asn Ser Gly Ser Lys Ile Leu Thr His Ile Asp Leu Ala Phe Gly
385                 390                 395                 400

His Lys Ser Phe Lys Asn Thr Tyr Leu Ala Gly Leu Ala Gln Tyr Tyr
                405                 410                 415

Ala Gln Tyr Ser Gly Ser Ile Asn Leu His Phe Met Thr Gly Pro
            420                 425                 430
```

| | | | | | | | | | | | |
|---|---|---|---|---|---|---|---|---|---|---|---|
|Thr|Gln|Ser|Lys|Ala|Arg|Phe|Met|Val|Ala|Tyr|Ile|Pro|Pro|Gly|Thr|
| | |435| | | |440| | | |445| | | | | |

Thr Gln Ser Lys Ala Arg Phe Met Val Ala Tyr Ile Pro Pro Gly Thr
            435                 440                 445

Thr Val Pro Asn Thr Pro Glu Gln Ala Ala His Cys Tyr His Ser Glu
450                 455                 460

Trp Asp Thr Gly Leu Asn Ser Lys Phe Thr Phe Thr Val Pro Tyr Met
465                 470                 475                 480

Ser Ala Ala Asp Phe Ala Tyr Thr Tyr Cys Asp Glu Pro Glu Gln Ala
                485                 490                 495

Ser Ala Gln Gly Trp Val Thr Leu Tyr Gln Ile Thr Asp Thr His Asp
                500                 505                 510

Pro Asp Ser Ala Val Leu Val Ser Val Ser Ala Gly Ala Asp Phe Glu
                515                 520                 525

Leu Arg Leu Pro Ile Asn Pro Ala Ala Gln Thr Thr Ser Ala Gly Glu
530                 535                 540

Gly Ala Asp Val Val Thr Thr Asp Val Thr Thr His Gly Gly Glu Val
545                 550                 555                 560

Ser Val Pro Arg Arg Gln His Thr Asn Val Glu Phe Leu Leu Asp Arg
                565                 570                 575

Phe Thr His Ile Gly Thr Ile Asn Gly His Arg Thr Ile Cys Leu Met
                580                 585                 590

Asp Thr Lys Glu His Thr Leu Val Gly Ala Ile Leu Arg Ser Ala Thr
                595                 600                 605

Tyr Tyr Phe Cys Asp Leu Glu Val Ala Val Leu Gly Asn Ala Lys Tyr
                610                 615                 620

Ala Ala Trp Val Pro Asn Gly Cys Pro His Thr Asp Arg Val Glu Asp
625                 630                 635                 640

Asn Pro Val Val His Ser Lys Gly Ser Val Val Arg Phe Ala Leu Pro
                645                 650                 655

Tyr Thr Ala Pro His Gly Val Leu Ala Thr Val Tyr Asn Gly Asn Cys
                660                 665                 670

Lys Tyr Ser Thr Thr Gln Arg Val Ala Pro Arg Gly Asp Leu Gly
                675                 680                 685

Val Leu Ser Gln Arg Val Glu Asn Glu Thr Thr Arg Cys Ile Pro Thr
690                 695                 700

Thr Phe Asn Phe Gly Arg Leu Leu Cys Glu Ser Gly Asp Val Tyr Tyr
705                 710                 715                 720

Arg Met Lys Arg Thr Glu Leu
                725

<210> SEQ ID NO 31
<211> LENGTH: 678
<212> TYPE: DNA
<213> ORGANISM: Artificial Sequence
<220> FEATURE:
<223> OTHER INFORMATION: nucleic acid consensus VP1-Asia

<400> SEQUENCE: 31

```
atggactgga cctggatcct gttcctggtc gccgctgcca ctagggtgca cagcaccacc      60
accaccggcg agagcgccga ccccgtgacc accaccgtgg agaactacgg cggcgagaca     120
cagaccgcca ggcgcctcca caccgacgtg gccttcgtgc tggacagatt cgtgaagctg     180
acccagccca agagcaccca gaccctggac ctgatgcaga tccccagcca caccctcgtg     240
ggcgccctgc tgagaagcgc cacctactac ttcagcgacc tggaagtggc cctggtgcac     300
accgcccctg tgacctgggt gcccaacggc gctcccaaga ccgccctgaa caaccacacc     360
```

```
aaccccaccg cctaccagaa gcagcccatc accaggctgg ccctgcccta caccgcccct    420
cacagggtgc tgtccaccgt gtacaacggc aagaccacct acggcgagga aagcagcaga    480 agggcgatc tggccgctct cgccaggcgc gtgaacaaca ggctgcccac ctccttcaac    540
tatggcgccg tcaaggccga caccatcacc gagctgctga tcaggatgaa gagggccgag    600
acatactgcc ccaggcccct gctggccctg gacaccacca ggacaggcg caagcaggaa    660 atcattgccc ccgagaag                                                 678
```

<210> SEQ ID NO 32
<211> LENGTH: 229
<212> TYPE: PRT
<213> ORGANISM: Artificial Sequence
<220> FEATURE:
<223> OTHER INFORMATION: Consensus VP1-Asia

<400> SEQUENCE: 32

```

```
tctaccgggg agtccgccga tcctgtgaca gccacagtgg aaaattacgg cggggaaacc    120
caggtgcaga ggcggcagca caccgatgtg tctttcatcc tggaccgctt cgtgaaagtg    180 accccccaagg ccgaccagat caacgtgctg gatctcatgc agattcccgc ccatacactc    240 gtcgggctc tgctgcgcac cgccacatac tatttcgccg atctcgaggt ggccgtgaag    300
cacgagggca acctgacatg ggtgccaaat ggcgccctg aggccgctct ggacaacacc    360
accaatccta cagcctacca caaggcccc ctgaccagac tggctctgcc ttatacagcc    420
ccccaccgcg tgctggccac agtgtataat ggcaactgca gtacggcga gtggccgtc    480 accaacgtgc gcggcgacct ccaggtgctg gcccagaagg ccgccaggac cctgcctacc    540
agctttaact acggggccat caaggccacc agagtgaccg aactgctgta cagaatgaag    600
cgcgccgaaa cctactgccc tagacctctg ctcgccatcc accccagcga ggccaggcac    660
aagcagaaaa ttgtggcccc tgtgaagcag ctgctgtgat gactgcagat atccagcaca    720
gtggcggccg ctcgagtcta ga                                              742
```

<210> SEQ ID NO 34
<211> LENGTH: 201
<212> TYPE: PRT
<213> ORGANISM: Artificial Sequence
<220> FEATURE:
<223> OTHER INFORMATION: Consensus VP1- O

<400> SEQUENCE: 34

```
Met Asp Trp Thr Trp Ile Leu Phe Leu Val Ala Ala Thr Arg Val
1               5                   10                  15

His Ser Thr Thr Ser Thr Gly Glu Ser Ala Asp Pro Val Thr Ala Thr
            20                  25                  30

Val Glu Asn Tyr Gly Gly Glu Thr Gln Val Gln Arg Arg Gln His Thr
        35                  40                  45

Asp Val Ser Phe Ile Leu Asp Arg Phe Val Lys Val Thr Pro Lys Ala
    50                  55                  60

Asp Gln Ile Asn Val Leu Asp Leu Met Gln Ile Pro Ala His Thr Leu
65                  70                  75                  80

Val Gly Ala Leu Leu Arg Thr Ala Thr Tyr Tyr Phe Ala Asp Leu Glu
                85                  90                  95

Val Ala Val Lys His Glu Gly Asn Leu Thr Trp Val Pro Asn Gly Ala
            100                 105                 110

Pro Glu Ala Ala Leu Asp Asn Thr Thr Asn Pro Thr Ala Tyr His Lys
        115                 120                 125

Ala Pro Leu Thr Arg Leu Ala Leu Pro Tyr Thr Ala Pro His Arg Val
    130                 135                 140

Leu Ala Thr Val Tyr Asn Gly Asn Cys Lys Tyr Gly Glu Val Ala Val
145                 150                 155                 160

Thr Asn Val Arg Gly Asp Leu Gln Val Leu Ala Gln Lys Ala Ala Arg
                165                 170                 175

Thr Leu Pro Thr Ser Phe Asn Tyr Gly Ala Ile Lys Ala Thr Arg Val
            180                 185                 190

Thr Glu Leu Leu Tyr Arg Met Lys Arg
        195                 200
```

<210> SEQ ID NO 35
<211> LENGTH: 771
<212> TYPE: DNA
<213> ORGANISM: Artificial Sequence
<220> FEATURE:

<223> OTHER INFORMATION: nucleic acid consensus VP1-A

<400> SEQUENCE: 35

```
atggactgga cctggattct gtttctggtg gccgctgcca caagagtgca ctccaccacc    60
tctgccggcg agtccgccga cccagtgacc accaccgtgg agaactacgg cggcgagaca   120
caggtgcagc gcaggcacca caccgacgtg ggcttcatca tggaccgctt cgtgaagatc   180
ggcaacacct cccccaccca cgtgatcgac ctgatgcaga cccaccagca cggactggtg   240
ggagccctgc tgagagccgc cacctactac ttctccgacc tggaaatcgt ggtgcgccac   300
gacggaaacc tgacatgggt gcccaatggc gccccagagg ccgccctgtc aacaccggc    360
aaccccaccg cctacaacaa ggccccctcc accagactgg ccctgccata caccgcccct   420
cacagggtgc tggccaccgt gtacaacggc accaacaagt actccgccgc ctccggaaga   480
acaagaggcg acctgggcac cgtggccgcc agaatcgccg cccagctgcc cgcctccttc   540
aacttcggcg ccatcaaggc cgacgccatc cacgaactgc tggtgcgcat gaagcgcgcc   600
gagctgtact gcccaagacc cctgctggcc gtggaggtgt cctcccagga ccgccacaag   660
cagaagatca tcgccccagc caagcagctg ctgtaccct acgacgtgcc cgactacgcc    720
tccctgggcg accatgatg actcgagtct agagggcccg tttaaacccg c             771
```

<210> SEQ ID NO 36
<211> LENGTH: 231
<212> TYPE: PRT
<213> ORGANISM: Artificial Sequence
<220> FEATURE:
<223> OTHER INFORMATION: Consensus VP1-A

<400> SEQUENCE: 36

```
Met Asp Trp Thr Trp Ile Leu Phe Leu Val Ala Ala Thr Arg Val
1               5                   10                  15

His Ser Thr Thr Ser Ala Gly Glu Ser Ala Asp Pro Val Thr Thr Thr
            20                  25                  30

Val Glu Asn Tyr Gly Gly Glu Thr Gln Val Gln Arg Arg His His Thr
        35                  40                  45

Asp Val Gly Phe Ile Met Asp Arg Phe Val Lys Ile Gly Asn Thr Ser
    50                  55                  60

Pro Thr His Val Ile Asp Leu Met Gln Thr His Gln His Gly Leu Val
65                  70                  75                  80

Gly Ala Leu Leu Arg Ala Ala Thr Tyr Tyr Phe Ser Asp Leu Glu Ile
                85                  90                  95

Val Val Arg His Asp Gly Asn Leu Thr Trp Val Pro Asn Gly Ala Pro
            100                 105                 110

Glu Ala Ala Leu Ser Asn Thr Gly Asn Pro Thr Ala Tyr Asn Lys Ala
        115                 120                 125

Pro Phe Thr Arg Leu Ala Leu Pro Tyr Thr Ala Pro His Arg Val Leu
    130                 135                 140

Ala Thr Val Tyr Asn Gly Thr Asn Lys Tyr Ser Ala Ala Ser Gly Arg
145                 150                 155                 160

Thr Arg Gly Asp Leu Gly Thr Val Ala Ala Arg Ile Ala Ala Gln Leu
                165                 170                 175

Pro Ala Ser Phe Asn Phe Gly Ala Ile Lys Ala Asp Ala Ile His Glu
            180                 185                 190

Leu Leu Val Arg Met Lys Arg Ala Glu Leu Tyr Cys Pro Arg Pro Leu
        195                 200                 205
```

```
Leu Ala Val Glu Val Ser Ser Gln Asp Arg His Lys Gln Lys Ile Ile
    210                 215                 220

Ala Pro Ala Lys Gln Leu Leu
225                 230

<210> SEQ ID NO 37
<211> LENGTH: 732
<212> TYPE: DNA
<213> ORGANISM: Artificial Sequence
<220> FEATURE:
<223> OTHER INFORMATION: nucleic acid consensus VP1-C

<400> SEQUENCE: 37
atggactgga cctggattct gtttctcgtg gccgctgcca caagagtgca cagcaccacc      60
accaccggcg agtccgccga cccagtgacc accaccgtgg agaactacgg cggcgagaca     120
cagacccagc gcaggcacca cacagacgtg gccttcgtgc tggaccgctt cgtgaaggtg     180
caggtgtccg gcaaccagca caccctggac gtgatgcagg tgcacaagga ctccatcgtg     240
ggcgccctgc tgagagccgc cacctactac ttctccgacc tggaaatcgc cgtgacccac     300
accggaaagc tgacctgggt gcccaatggc gccccagtgt ccgccctgga caacaccacc     360
aaccccaccg cctaccacaa gggcccactg accagactgg ccctgccata caccgccccc     420
cacagagtgc tggccacagc ctacaccggc acaaccgcct actccgcctc cgccagaaga     480
ggcgatctgg cccacctcgc cgctgcccac gccagcacc tgcccaccag cttcaacttc      540
ggcgccgtga aggccgagac aatcaccgag ctgctggtgc gcatgaagcg cgccgagctg     600 tactgccccca gacccgtgct gccagtgcag ccatccggcg acagacacaa gcagcccctg     660
atcgccccag ccaagcagct gctgtacccc tacgacgtgc ccgactacgc ctccctgggc     720
ggaccatgat ga                                                          732

<210> SEQ ID NO 38
<211> LENGTH: 228
<212> TYPE: PRT
<213> ORGANISM: Artificial Sequence
<220> FEATURE:
<223> OTHER INFORMATION: Consensus VP1-C

<400> SEQUENCE: 38

Met Asp Trp Thr Trp Ile Leu Phe Leu Val Ala Ala Thr Arg Val
1               5                   10                  15

His Ser Thr Thr Thr Thr Gly Glu Ser Ala Asp Pro Val Thr Thr Thr
                20                  25                  30

Val Glu Asn Tyr Gly Gly Glu Thr Gln Thr Gln Arg His His Thr
            35                  40                  45

Asp Val Ala Phe Val Leu Asp Arg Phe Val Lys Val Gln Val Ser Gly
    50                  55                  60

Asn Gln His Thr Leu Asp Val Met Gln Val His Lys Asp Ser Ile Val
65                  70                  75                  80

Gly Ala Leu Leu Arg Ala Ala Thr Tyr Tyr Phe Ser Asp Leu Glu Ile
                85                  90                  95

Ala Val Thr His Thr Gly Lys Leu Thr Trp Val Pro Asn Gly Ala Pro
            100                 105                 110

Val Ser Ala Leu Asp Asn Thr Thr Asn Pro Thr Ala Tyr His Lys Gly
        115                 120                 125

Pro Leu Thr Arg Leu Ala Leu Pro Tyr Thr Ala Pro His Arg Val Leu
    130                 135                 140
```

```
Ala Thr Ala Tyr Thr Gly Thr Thr Ala Tyr Ser Ala Ser Ala Arg Arg
145                 150                 155                 160

Gly Asp Leu Ala His Leu Ala Ala Ala His Ala Arg His Leu Pro Thr
                165                 170                 175

Ser Phe Asn Phe Gly Ala Val Lys Ala Glu Thr Ile Thr Glu Leu Leu
            180                 185                 190

Val Arg Met Lys Arg Ala Glu Leu Tyr Cys Pro Arg Pro Val Leu Pro
        195                 200                 205

Val Gln Pro Ser Gly Asp Arg His Lys Gln Pro Leu Ile Ala Pro Ala
    210                 215                 220

Lys Gln Leu Leu
225

<210> SEQ ID NO 39
<211> LENGTH: 1404
<212> TYPE: DNA
<213> ORGANISM: Artificial Sequence
<220> FEATURE:
<223> OTHER INFORMATION: nucleic acid, VP1-A+ VP1-C sequence

<400> SEQUENCE: 39
atggactgga cctggattct gtttctcgtg gccgctgcta caagagtgca ctccaccacc      60
tctgccggcg agtccgccga cccagtgacc accaccgtgg agaactacgg cggcgagaca     120
caggtgcagc gcaggcacca caccgacgtg ggcttcatca tggaccgctt cgtgaagatc     180
ggcaacacct cccccaccca cgtgatcgac ctgatgcaga cccaccagca cggactggtg     240
ggagccctgc tgagagccgc cacctactac ttctccgacc tggaaatcgt ggtgcgccac     300
gacggaaacc tgacctgggt gcccaatggc gctccagagg ccgccctgtc caacaccggc     360
aaccccaccg cctacaacaa ggccccctte accagactgg ccctgccata caccgcccct     420
cacagggtgc tggccaccgt gtacaacggc accaacaagt actccgccgc ctccggaaga     480
acaagaggcg acctgggcac cgtggccgcc agaatcgccg cccagctgcc cgcctccttc     540
aacttcggcg ccatcaaggc cgacgccatc cacgaactgc tggtgcgcat gaagcgcgcc     600
gagctgtact gcccaagacc cctgctggcc gtggaggtgt cctcccagga ccgccacaag     660
cagaagatca tcgccccagc caagcagctg ctgcgcggca ggaagagaag atccaccacc     720
accacaggcg aaagcgccga tcccgtgaca acaacagtgg aaaattacgg cggggaaacc     780
cagacccagc ggcgccacca cacagatgtg gccttcgtgc tggacagatt cgtgaaggtg     840
caggtgtccg gcaaccagca caccctggac gtgatgcagg tgcacaagga ctccatcgtg     900
ggcgccctgc tgagggccgc cacctactac tttagcgatc tggaaatcgc cgtgacccac     960
accggcaagc tgacatgggt gccaaatggg gcccctgtgt ctgccctgga caacaccacc    1020
aacccaacag cctaccacaa agggccactg acacgcctgg ccctgcctta cacagcccca    1080
caccgcgtgc tggccacagc ctacaccgga accaccgcct actccgcctc cgccagaaga    1140
ggcgatctgg cccatctggc cgctgcccac gccagacacc tgcccaccag cttcaacttt    1200
ggggccgtga aagccgagac aatcaccgag ctgctggtgc ggatgaagag ggccgaactg    1260
tactgtcctc gccccgtgct gccagtgcag ccatccggcg acagacacaa gcagcccctg    1320
atcgcccctg ccaaacagct gctgtacccc tacgacgtgc ccgactacgc ctccctgggc    1380
ggaccatgat gactcgagtc taga                                           1404

<210> SEQ ID NO 40
<211> LENGTH: 448
```

-continued

<212> TYPE: PRT
<213> ORGANISM: Artificial Sequence
<220> FEATURE:
<223> OTHER INFORMATION: VP1-A+ VP1-C amino acid sequence

<400> SEQUENCE: 40

```
Met Asp Trp Thr Trp Ile Leu Phe Leu Val Ala Ala Ala Thr Arg Val
1               5                   10                  15

His Ser Thr Thr Ser Ala Gly Glu Ser Ala Asp Pro Val Thr Thr Thr
            20                  25                  30

Val Glu Asn Tyr Gly Gly Glu Thr Gln Val Gln Arg Arg His His Thr
        35                  40                  45

Asp Val Gly Phe Ile Met Asp Arg Phe Val Lys Ile Gly Asn Thr Ser
    50                  55                  60

Pro Thr His Val Ile Asp Leu Met Gln Thr His Gln His Gly Leu Val
65                  70                  75                  80

Gly Ala Leu Leu Arg Ala Ala Thr Tyr Tyr Phe Ser Asp Leu Glu Ile
                85                  90                  95

Val Val Arg His Asp Gly Asn Leu Thr Trp Val Pro Asn Gly Ala Pro
            100                 105                 110

Glu Ala Ala Leu Ser Asn Thr Gly Asn Pro Thr Ala Tyr Asn Lys Ala
        115                 120                 125

Pro Phe Thr Arg Leu Ala Leu Pro Tyr Thr Ala Pro His Arg Val Leu
    130                 135                 140

Ala Thr Val Tyr Asn Gly Thr Asn Lys Tyr Ser Ala Ala Ser Gly Arg
145                 150                 155                 160

Thr Arg Gly Asp Leu Gly Thr Val Ala Ala Arg Ile Ala Ala Gln Leu
                165                 170                 175

Pro Ala Ser Phe Asn Phe Gly Ala Ile Lys Ala Asp Ala Ile His Glu
            180                 185                 190

Leu Leu Val Arg Met Lys Arg Ala Glu Leu Tyr Cys Pro Arg Pro Leu
        195                 200                 205

Leu Ala Val Glu Val Ser Ser Gln Asp Arg His Lys Gln Lys Ile Ile
    210                 215                 220

Ala Pro Ala Lys Gln Leu Leu Arg Gly Arg Lys Arg Arg Ser Thr Thr
225                 230                 235                 240

Ala Thr Gly Glu Ser Ala Asp Pro Val Thr Thr Thr Val Glu Asn Tyr
                245                 250                 255

Gly Gly Glu Thr Gln Thr Gln Arg Arg His His Thr Asp Val Ala Phe
            260                 265                 270

Val Leu Asp Arg Phe Val Lys Val Gln Val Ser Gly Asn Gln His Thr
        275                 280                 285

Leu Asp Val Met Gln Val His Lys Asp Ser Ile Val Gly Ala Leu Leu
    290                 295                 300

Arg Ala Ala Thr Tyr Tyr Phe Ser Asp Leu Glu Ile Ala Val Thr His
305                 310                 315                 320

Thr Gly Lys Leu Thr Trp Val Pro Asn Gly Ala Pro Val Ser Ala Leu
                325                 330                 335

Asp Asn Thr Thr Asn Pro Thr Ala Tyr His Lys Gly Pro Leu Thr Arg
            340                 345                 350

Leu Ala Leu Pro Tyr Thr Ala Pro His Arg Val Leu Ala Thr Ala Tyr
        355                 360                 365

Thr Gly Thr Thr Ala Tyr Ser Ala Ser Ala Arg Arg Gly Asp Leu Ala
    370                 375                 380
```

-continued

```
His Leu Ala Ala Ala His Ala Arg His Leu Pro Thr Ser Phe Asn Phe
385                 390                 395                 400

Gly Ala Val Lys Ala Glu Thr Ile Thr Glu Leu Leu Val Arg Met Lys
                405                 410                 415

Arg Ala Glu Leu Tyr Cys Pro Arg Pro Val Leu Pro Val Gln Pro Ser
            420                 425                 430

Gly Asp Arg His Lys Gln Pro Leu Ile Ala Pro Ala Lys Gln Leu Leu
        435                 440                 445

<210> SEQ ID NO 41
<211> LENGTH: 1350
<212> TYPE: DNA
<213> ORGANISM: Artificial Sequence
<220> FEATURE:
<223> OTHER INFORMATION: nucleic acid VP1-Asia + VP1-O sequence

<400> SEQUENCE: 41
atggactgga cctggatcct gttcctggtc gccgctgcca ctagggtgca cagcaccacc      60
accaccggcg agagcgccga ccccgtgacc accaccgtgg agaactacgg cggcgagaca     120
cagaccgcca ggcgcctcca caccgacgtg gccttcgtgc tggacagatt cgtgaagctg     180
acccagccca agagcaccca gaccctggac ctgatgcaga tccccagcca caccctcgtg     240
ggcgccctgc tgagaagcgc cacctactac ttcagcgacc tggaagtggc cctggtgcac     300
accggccctg tgacctgggt gcccaacggc gctcccaaga ccgccctgaa caaccacacc     360
aaccccaccg cctaccagaa gcagcccatc accaggctgg ccctgcccta caccgcccct     420
cacagggtgc tgtccaccgt gtacaacggc aagaccacct acggcgagga aagcagcaga     480
aggggcgatc tggccgctct cgccaggcgc gtgaacaaca ggctgcccac ctccttcaac     540
tatggcgccg tcaaggccga caccatcacc gagctgctga tcaggatgaa gagggccgag     600
acatactgcc ccaggcccct gctggccctg gacaccaccc aggacaggcg caagcaggaa     660
atcattgccc ccgagaagca gaccctgagg ggcaggaaga ggcgctccac cacctctacc     720
ggggagtccg ccgatcctgt gacagccaca gtggaaaatt acggcgggga aacccaggtg     780
cagaggcggc agcacaccga tgtgtctttc atcctggacc gcttcgtgaa agtgaccccc     840
aaggccgacc agatcaacgt gctggatctc atgcagattc ccgcccatac actcgtcggg     900
gctctgctgc gcaccgccac atactatttc gccgatctcg aggtggccgt gaagcacgag     960
ggcaacctga catgggtgcc aaatggcgcc cctgaggccg ctctggacaa caccaccaat    1020
cctacagcct accacaaggc cccctgacc agactggctc tgccttatac agccccccac     1080
cgcgtgctgg ccacagtgta taatggcaac tgcaagtacg gcgaagtggc cgtcaccaac    1140
gtgcgcggcg acctccaggt gctggcccag aaggccgcca ggaccctgcc taccagcttt    1200
aactacgggg ccatcaaggc caccagagtg accgaactgc tgtacagaat gaagcgcgcc    1260
gaaacctact gccctagacc tctgctcgcc atccacccag cgaggccagg cacaagcaga    1320
aaattgtggc ccctgtgaag cagctgctgt                                     1350

<210> SEQ ID NO 42
<211> LENGTH: 470
<212> TYPE: PRT
<213> ORGANISM: Artificial Sequence
<220> FEATURE:
<223> OTHER INFORMATION: VP1-Asia + VP1-O amino acid sequence

<400> SEQUENCE: 42

Met Asp Trp Thr Trp Ile Leu Phe Leu Val Ala Ala Ala Thr Arg Val
```

```
  1               5                  10                 15
His Ser Thr Thr Thr Thr Gly Glu Ser Ala Asp Pro Val Thr Thr Thr
                    20                  25                  30

Val Glu Asn Tyr Gly Gly Glu Thr Gln Thr Ala Arg Arg Leu His Thr
                    35                  40                  45

Asp Val Ala Phe Val Leu Asp Arg Phe Val Lys Leu Thr Gln Pro Lys
                    50                  55                  60

Ser Thr Gln Thr Leu Asp Leu Met Gln Ile Pro Ser His Thr Leu Val
 65                 70                  75                  80

Gly Ala Leu Leu Arg Ser Ala Thr Tyr Tyr Phe Ser Asp Leu Glu Val
                    85                  90                  95

Ala Leu Val His Thr Gly Pro Val Thr Trp Val Pro Asn Gly Ala Pro
                   100                 105                 110

Lys Thr Ala Leu Asn Asn His Thr Asn Pro Thr Ala Tyr Trp Val Pro
                   115                 120                 125

Asn Gly Ala Pro Lys Thr Ala Leu Asn Asn His Thr Asn Pro Thr Ala
                   130                 135                 140

Tyr Gln Lys Gln Pro Ile Thr Arg Leu Ala Leu Pro Tyr Thr Ala Pro
145                    150                 155                 160

His Arg Val Leu Ser Thr Val Tyr Asn Gly Lys Thr Thr Tyr Gly Glu
                   165                 170                 175

Glu Ser Ser Arg Arg Gly Asp Leu Ala Ala Leu Ala Arg Arg Val Asn
                   180                 185                 190

Asn Arg Leu Pro Thr Ser Phe Asn Tyr Gly Ala Val Lys Ala Asp Thr
                   195                 200                 205

Ile Thr Glu Leu Leu Ile Arg Met Lys Arg Ala Glu Thr Tyr Cys Pro
                   210                 215                 220

Arg Pro Leu Leu Ala Leu Asp Thr Thr Gln Asp Arg Arg Lys Gln Glu
225                    230                 235                 240

Ile Ile Ala Pro Glu Lys Gln Thr Leu Arg Gly Arg Lys Arg Arg Ser
                   245                 250                 255

Thr Thr Ser Thr Gly Glu Ser Ala Asp Pro Val Thr Ala Thr Val Glu
                   260                 265                 270

Asn Tyr Gly Gly Glu Thr Gln Val Gln Arg Gln Arg Gln His Thr Asp Val
                   275                 280                 285

Ser Phe Ile Leu Asp Arg Phe Val Lys Val Thr Pro Lys Ala Asp Gln
                   290                 295                 300

Ile Asn Val Leu Asp Leu Met Gln Ile Pro Ala His Thr Leu Val Gly
305                    310                 315                 320

Ala Leu Leu Arg Thr Ala Thr Tyr Tyr Phe Ala Asp Leu Glu Val Ala
                   325                 330                 335

Val Lys His Glu Gly Asn Leu Thr Trp Val Pro Asn Gly Ala Pro Glu
                   340                 345                 350

Ala Ala Leu Asp Asn Thr Thr Asn Pro Thr Ala Tyr His Lys Ala Pro
                   355                 360                 365

Leu Thr Arg Leu Ala Leu Pro Tyr Thr Ala Pro His Arg Val Leu Ala
                   370                 375                 380

Thr Val Tyr Asn Gly Asn Cys Lys Tyr Gly Glu Val Ala Val Thr Asn
385                    390                 395                 400

Val Arg Gly Asp Leu Gln Val Leu Ala Gln Lys Ala Ala Arg Thr Leu
                   405                 410                 415

Pro Thr Ser Phe Asn Tyr Gly Ala Ile Lys Ala Thr Arg Val Thr Glu
                   420                 425                 430
```

Leu Leu Tyr Arg Met Lys Arg Ala Glu Thr Tyr Cys Pro Arg Pro Leu
            435                 440                 445

Leu Ala Ile His Pro Ser Glu Ala Arg His Lys Gln Lys Ile Val Ala
    450                 455                 460

Pro Val Lys Gln Leu Leu
465                 470

<210> SEQ ID NO 43
<211> LENGTH: 56
<212> TYPE: DNA
<213> ORGANISM: Artificial Sequence
<220> FEATURE:
<223> OTHER INFORMATION: IgE leader sequence

<400> SEQUENCE: 43
atggactgga cctggatcct gttcctggtc gccgctgcca ctagggtgca cagcac      56

<210> SEQ ID NO 44
<211> LENGTH: 18
<212> TYPE: PRT
<213> ORGANISM: Artificial Sequence
<220> FEATURE:
<223> OTHER INFORMATION: IgE amino acid sequence

<400> SEQUENCE: 44

Met Asp Trp Thr Trp Ile Leu Phe Leu Val Ala Ala Thr Arg Val
1               5                   10                  15

His Ser

<210> SEQ ID NO 45
<211> LENGTH: 7
<212> TYPE: PRT
<213> ORGANISM: Artificial Sequence
<220> FEATURE:
<223> OTHER INFORMATION: amino acid sequence 1

<400> SEQUENCE: 45

Arg Gly Arg Lys Arg Arg Ser
1               5

<210> SEQ ID NO 46
<211> LENGTH: 229
<212> TYPE: PRT
<213> ORGANISM: Artificial Sequence
<220> FEATURE:
<223> OTHER INFORMATION: amino acid sequence with Type Asia 1 VP1

<400> SEQUENCE: 46

Met Asp Trp Thr Trp Ile Leu Phe Leu Val Ala Ala Thr Arg Val
1               5                   10                  15

His Ser Thr Thr Thr Thr Gly Glu Ser Ala Asp Pro Val Thr Thr Thr
            20                  25                  30

Val Glu Asn Tyr Gly Gly Glu Thr Gln Thr Ala Arg Arg Leu His Thr
        35                  40                  45

Asp Val Ala Phe Val Leu Asp Arg Phe Val Lys Leu Thr Gln Pro Lys
    50                  55                  60

Ser Thr Gln Thr Leu Asp Leu Met Gln Ile Pro Ser His Thr Leu Val
65                  70                  75                  80

Gly Ala Leu Leu Arg Ser Ala Thr Tyr Tyr Phe Ser Asp Leu Glu Val
                85                  90                  95

Ala Leu Val His Thr Gly Pro Val Thr Trp Val Pro Asn Gly Ala Pro 100 105 110

Lys Thr Ala Leu Asn Asn His Thr Asn Pro Thr Ala Tyr Gln Lys Gln
115 120 125

Pro Ile Thr Arg Leu Ala Leu Pro Tyr Thr Ala Pro His Arg Val Leu
130 135 140

Ser Thr Val Tyr Asn Gly Lys Thr Thr Tyr Gly Glu Glu Ser Ser Arg
145 150 155 160

Arg Gly Asp Leu Ala Ala Leu Ala Arg Arg Val Asn Asn Arg Leu Pro
165 170 175

Thr Ser Phe Asn Tyr Gly Ala Val Lys Ala Asp Thr Ile Thr Glu Leu
180 185 190

Leu Ile Arg Met Lys Arg Ala Glu Thr Tyr Cys Pro Arg Pro Leu Leu
195 200 205

Ala Leu Asp Thr Thr Gln Asp Arg Arg Lys Gln Glu Ile Ile Ala Pro
210 215 220

Glu Lys Gln Thr Leu
225

<210> SEQ ID NO 47
<211> LENGTH: 232
<212> TYPE: PRT
<213> ORGANISM: Artificial Sequence
<220> FEATURE:
<223> OTHER INFORMATION: amino acid sequence with Type O VP1

<400> SEQUENCE: 47

Met Asp Trp Thr Trp Ile Leu Phe Leu Val Ala Ala Ala Thr Arg Val
1 5 10 15

His Ser Thr Thr Ser Thr Gly Glu Ser Ala Asp Pro Val Thr Ala Thr
20 25 30

Val Glu Asn Tyr Gly Gly Glu Thr Gln Val Gln Arg Arg Gln His Thr
35 40 45

Asp Val Ser Phe Ile Leu Asp Arg Phe Val Lys Val Thr Pro Lys Ala
50 55 60

Asp Gln Ile Asn Val Leu Asp Leu Met Gln Ile Pro Ala His Thr Leu
65 70 75 80

Val Gly Ala Leu Leu Arg Thr Ala Thr Tyr Tyr Phe Ala Asp Leu Glu
85 90 95

Val Ala Val Lys His Glu Gly Asn Leu Thr Trp Val Pro Asn Gly Ala
100 105 110

Pro Glu Ala Ala Leu Asp Asn Thr Thr Asn Pro Thr Ala Tyr His Lys
115 120 125

Ala Pro Leu Thr Arg Leu Ala Leu Pro Tyr Thr Ala Pro His Arg Val
130 135 140

Leu Ala Thr Val Tyr Asn Gly Asn Cys Lys Tyr Gly Glu Val Ala Val
145 150 155 160

Thr Asn Val Arg Gly Asp Leu Gln Val Leu Ala Gln Lys Ala Ala Arg
165 170 175

Thr Leu Pro Thr Ser Phe Asn Tyr Gly Ala Ile Lys Ala Thr Arg Val
180 185 190

Thr Glu Leu Leu Tyr Arg Met Lys Arg Ala Glu Thr Tyr Cys Pro Arg
195 200 205

Pro Leu Leu Ala Ile His Pro Ser Glu Ala Arg His Lys Gln Lys Ile
210 215 220

Val Ala Pro Val Lys Gln Leu Leu

<210> SEQ ID NO 48
<211> LENGTH: 231
<212> TYPE: PRT
<213> ORGANISM: Artificial Sequence
<220> FEATURE:
<223> OTHER INFORMATION: amino acid sequence with Type A VP1

<400> SEQUENCE: 48

Met Asp Trp Thr Trp Ile Leu Phe Leu

```
Asn Gln His Thr Leu Asp Val Met Gln Val His Lys Asp Ser Ile Val
 65              70                  75                  80

Gly Ala Leu Leu Arg Ala Ala Thr Tyr Tyr Phe Ser Asp Leu Glu Ile
             85                  90                  95

Ala Val Thr His Thr Gly Lys Leu Thr Trp Val Pro Asn Gly Ala Pro
            100                 105                 110

Val Ser Ala Leu Asp Asn Thr Thr Asn Pro Thr Ala Tyr His Lys Gly
        115                 120                 125

Pro Leu Thr Arg Leu Ala Leu Pro Tyr Thr Ala Pro His Arg Val Leu
        130                 135                 140

Ala Thr Ala Tyr Thr Gly Thr Thr Ala Tyr Ser Ala Ser Ala Arg Arg
145                 150                 155                 160

Gly Asp Leu Ala His Leu Ala Ala Ala His Ala Arg His Leu Pro Thr
                165                 170                 175

Ser Phe Asn Phe Gly Ala Val Lys Ala Glu Thr Ile Thr Glu Leu Leu
                180                 185                 190

Val Arg Met Lys Arg Ala Glu Leu Tyr Cys Pro Arg Pro Val Leu Pro
            195                 200                 205

Val Gln Pro Ser Gly Asp Arg His Lys Gln Pro Leu Ile Ala Pro Ala
        210                 215                 220

Lys Gln Leu Leu
225
```